(12) United States Patent
Cullen et al.

(10) Patent No.: US 12,090,323 B2
(45) Date of Patent: Sep. 17, 2024

(54) IMPLANTABLE LIVING ELECTRODES AND METHODS FOR USE THEREOF

(71) Applicants: The Trustees of the University of Pennsylvania, Philadelphia, PA (US); Thomas Jefferson University, Philadelphia, PA (US)

(72) Inventors: Daniel Kacy Cullen, Media, PA (US); James P. Harris, Philadelphia, PA (US); John A. Wolf, Philadelphia, PA (US); Han-Chiao Isaac Chen, Penn Valley, PA (US); Douglas H. Smith, Boothwyn, PA (US); Mijail Serruya, Philadelphia, PA (US)

(73) Assignees: The Trustees of the University of Pennsylvania, Philadelphia, PA (US); Thomas Jefferson University, Philadelphia, PA (US)

( * ) Notice: Subject to any disclaimer, the term of this patent is extended or adjusted under 35 U.S.C. 154(b) by 238 days.

(21) Appl. No.: 17/358,851

(22) Filed: Jun. 25, 2021

(65) Prior Publication Data
US 2021/0393960 A1    Dec. 23, 2021

Related U.S. Application Data

(63) Continuation of application No. 16/093,036, filed as application No. PCT/US2017/027705 on Apr. 14, 2017, now abandoned.
(Continued)

(51) Int. Cl.
*A61N 1/36* (2006.01)
*A61B 5/00* (2006.01)
(Continued)

(52) U.S. Cl.
CPC ............ *A61N 1/36067* (2013.01); *A61B 5/24* (2021.01); *A61B 5/291* (2021.01); *A61B 5/6868* (2013.01);
(Continued)

(58) Field of Classification Search
None
See application file for complete search history.

(56) References Cited

U.S. PATENT DOCUMENTS

| 5,061,281 A | 10/1991 | Mares |
| 5,358,475 A | 10/1994 | Mares |

(Continued)

FOREIGN PATENT DOCUMENTS

| JP | 2009506836 | 2/2009 |
| WO | 2011102991 A1 | 8/2011 |

(Continued)

OTHER PUBLICATIONS

Ren, et al., "Intracerebral neural stem cell transplantation improved the auditory of mice with presbycusis", Int J Clin Exp Pathol 6(2), 2013, 230-241.
(Continued)

*Primary Examiner* — Ankit D Tejani
(74) *Attorney, Agent, or Firm* — Saul Ewing LLP; Kathryn Doyle; Justin Crotty

(57) ABSTRACT

In one aspect, the invention comprises an implantable living electrode comprising a substantially cylindrical extracellular matrix core; one or more neurons implanted along or within the substantially cylindrical extracellular matrix core, the one or more neurons including one or more optogenetic or magnetogenetic neurons proximal to a first end of the implantable living electrode.

18 Claims, 37 Drawing Sheets

Related U.S. Application Data

(60) Provisional application No. 62/322,434, filed on Apr. 14, 2016.

(51) Int. Cl.
*A61B 5/24* (2021.01)
*A61B 5/291* (2021.01)
*A61N 1/05* (2006.01)
*A61N 5/06* (2006.01)
*A61B 5/01* (2006.01)

(52) U.S. Cl.
CPC .............. *A61N 1/05* (2013.01); *A61N 1/0536* (2013.01); *A61N 1/36182* (2013.01); *A61N 5/0601* (2013.01); *A61N 5/0622* (2013.01); *A61B 5/0059* (2013.01); *A61B 5/01* (2013.01); *A61B 5/4082* (2013.01); *A61B 5/4088* (2013.01); *A61B 5/4094* (2013.01); *A61N 1/0531* (2013.01)

(56) References Cited

U.S. PATENT DOCUMENTS

| | | |
|---|---|---|
| 6,171,610 B1 | 1/2001 | Vacanti |
| 6,264,944 B1 | 7/2001 | Smith |
| 6,365,153 B2 | 4/2002 | Smith |
| 6,461,629 B1 | 10/2002 | Tranquillo |
| 6,548,569 B1 | 4/2003 | Williams |
| 7,338,517 B2 | 3/2008 | Yost |
| 7,429,267 B2 | 9/2008 | Smith et al. |
| 8,401,635 B2 | 3/2013 | Smith |
| 8,497,017 B2 | 7/2013 | Ohrlander |
| 8,685,634 B2 | 4/2014 | Boruch |
| 8,747,880 B2 | 6/2014 | Forgacs |
| 9,139,935 B2 | 9/2015 | Chen |
| 9,386,990 B2 | 7/2016 | Muir |
| 9,556,415 B2 | 1/2017 | Forgacs |
| 9,572,909 B2 | 2/2017 | Simpson |
| 9,713,521 B2 | 7/2017 | Chen |
| 9,717,761 B2 | 8/2017 | Pitaru |
| 9,737,635 B2 | 8/2017 | Brown |
| 9,820,747 B2 | 11/2017 | Siemionow |
| 10,179,192 B2 | 1/2019 | Brown |
| 10,617,300 B2 | 4/2020 | Rogers |
| 10,772,989 B2 | 9/2020 | Brown |
| 11,060,066 B2 | 7/2021 | Thomson |
| 2001/0031974 A1 | 10/2001 | Hadlock |
| 2001/0038835 A1 | 11/2001 | Smith |
| 2002/0168338 A1 | 11/2002 | Baird |
| 2003/0049839 A1 | 3/2003 | Romero-Ortega |
| 2003/0059933 A1 | 3/2003 | Tresco |
| 2004/0101518 A1 | 5/2004 | Vacanti |
| 2006/0292187 A1 | 12/2006 | Smith |
| 2007/0010831 A1 | 1/2007 | Romero-Ortega |
| 2007/0060815 A1 | 3/2007 | Martin et al. |
| 2007/0067883 A1 | 3/2007 | Sretavan |
| 2007/0100358 A2 | 5/2007 | Romero-Ortega |
| 2007/0155010 A1 | 7/2007 | Farnsworth |
| 2008/0014631 A1* | 1/2008 | Muraguchi ...... G01N 33/54366 435/287.1 |
| 2008/0022660 A1 | 1/2008 | Reuter |
| 2008/0226609 A1 | 9/2008 | Proschel |
| 2008/0300691 A1 | 12/2008 | Romero-Ortega |
| 2009/0222067 A1 | 9/2009 | Toselli et al. |
| 2010/0028436 A1 | 2/2010 | Ohrlander |
| 2010/0226895 A1 | 9/2010 | Boruch |
| 2011/0087338 A1 | 4/2011 | Siemionow |
| 2011/0105998 A1 | 5/2011 | Zhang et al. |
| 2011/0212501 A1 | 9/2011 | Yoo |
| 2011/0263504 A1 | 10/2011 | Cerami |
| 2011/0264235 A1 | 10/2011 | Chen |
| 2011/0300598 A1 | 12/2011 | Smith |
| 2012/0128636 A1 | 5/2012 | Le |
| 2012/0184035 A1 | 7/2012 | Agarwal |
| 2012/0221025 A1 | 8/2012 | Simpson |
| 2013/0046134 A1 | 2/2013 | Parker |
| 2013/0110138 A1 | 5/2013 | Hurtado |
| 2013/0171116 A1 | 7/2013 | Shoham et al. |
| 2014/0024116 A1 | 1/2014 | Subramanian |
| 2014/0050704 A1 | 2/2014 | Kumar |
| 2014/0051168 A1 | 2/2014 | Vukasinovic |
| 2014/0308256 A1 | 10/2014 | Lu |
| 2014/0371564 A1 | 12/2014 | Anikeeva et al. |
| 2015/0024025 A1 | 1/2015 | Floyd |
| 2015/0202351 A1 | 7/2015 | Kaplan |
| 2015/0342719 A1 | 12/2015 | Chen |
| 2015/0352153 A1 | 12/2015 | Smith |
| 2016/0040961 A1 | 2/2016 | Kovalev |
| 2016/0245788 A1 | 8/2016 | Wang |
| 2016/0250385 A1 | 9/2016 | Cullen |
| 2017/0007824 A1* | 1/2017 | Gardner ............... A61N 1/0529 |
| 2017/0368180 A1 | 12/2017 | Cullen |
| 2018/0214492 A1 | 8/2018 | Smith |
| 2018/0256647 A1 | 9/2018 | Bitar |
| 2019/0126043 A1 | 5/2019 | Cullen |
| 2019/0269755 A1 | 9/2019 | Pruneau |
| 2020/0063099 A1 | 2/2020 | Feyeux |
| 2020/0208105 A1 | 7/2020 | Zimmermann |
| 2020/0237867 A1 | 7/2020 | Romero-Ortega |
| 2021/0393960 A1 | 12/2021 | Cullen |

FOREIGN PATENT DOCUMENTS

| | | |
|---|---|---|
| WO | 2013002953 A1 | 1/2013 |
| WO | 2015066627 A1 | 5/2015 |
| WO | 2016040961 A1 | 3/2016 |
| WO | 2016094850 A1 | 6/2016 |
| WO | 2016176333 A1 | 11/2016 |
| WO | 2017145163 A1 | 8/2017 |
| WO | 2017181068 A1 | 10/2017 |
| WO | 2019071106 | 4/2019 |
| WO | 2022182723 A1 | 9/2022 |

OTHER PUBLICATIONS

Shin, "Biomimetic materials for tissue engineering", Biomaterials 24, 2003, 4353-4364.

Sinclair, et al., "Dopamine cells in nigral grafts differentiate prior to implantation", Eur J Neurosci 11(12), 1999, 4341-4348.

Smith, et al., "High Tolerance and Delayed Elastic Response of Cultured Axons to Dynamic Stretch Injury", J NeurOsci 19(11), 1999, 4263-4269.

Sorribas, et al., "Photolithographic generation of protein micropatterns for neuron culture applications", Biomaterials, 23(3):, 2002, 893-900.

Tallantyre, et al., "Clinico-pathological evidence that axonal loss underlies disability in progressive multiple sclerosis", Mult Scler, 16(4), 2010, 406-411.

Tate, et al., "Fibronectin Promotes Survival and Migration of Primary Neural Stem Cells Transplanted Into the Traumatically Injured Mouse Brain", Cell Transplant 11 (3), 2002, 283-295 (abstract only).

Tate, et al., "Laminin and fibronectin scaffolds enhance neural stem cell transplantation into the injured brain", J Tissue Eng Regen Med 3(3), 2009, 208-217.

Thomas, et al., "Hypersensitive Glutamate Signaling Correlates with the Development of Late-Onset Behavioral Morbidity in Diffuse Brain-Injured Circuitry", J Neurotrauma, 29(2):, 2012, 187-200.

Wheeler, et al., "Patterning to influence in vitro neuronal interfaces", Conf Proc IEEE Eng Med Biol Soc 7,2004, 6337-5339.

Woerly, et al., "Cultured rat neuronal and glial cells entrapped within hydrogel polymer matrices: a potential tool for neural tissue replacement", Neurosci Lett, 205(3), 1996, 197-201.

Yoo, et al., "Simple and Novel Three Dimensional Neuronal Cell Culture Using a Micro Mesh Scaffold", Exp Neurobiol 20(2), 2011, 110-115.

Fedoroff and Richardson edited, Book: Protocols for neural cell culture, 2nd edition, 1997, Springer Science Business Media New York.

(56) References Cited

OTHER PUBLICATIONS

The catalog of surface area for corning cell culture vessels from the Corning website:www.corning.com/catalog/cls/documents/ application-notes/CLS-AN-209.pdf, retrieved on Aug. 31, 20, "Surface Areas and Guide for Recommended Medium Volumes for Corning Cell Culture Vessels".

Yang et al., "Optimized and efficient preparation of astrocyte cultures from rat spinal cord," Cytotechnology, 2006; 52:87-97.doi 10.1007/s 10616-006-9033-4.

Watson et al., "Bioengineered 3D Glial Cell Culture Systems and Applications for Neurodegeneration and Nuroinflammation," SLAS Discovery, 2017; 22:583-601.

Abbott, Chapter 8, the Bipolar Astrocyte: Polarized Features of Astrocytic Glia Underlying Physiology, with Particular Reference to the Blood-Brain Barrier. Book: Blood-Brain Interfaces: From Ontogeny to Artificial Barrier, Edited by Dermietzel et al., 2006, wiley-VCH Verlag Gmbh & Co. KGaA, Weinhem.

Peng et al., Chapter 13, Astrocyte Polarization and Wound Healing in Culture: Studying Cell Adhesion Molecules. Book: Astrocytes: Methods and Protocols, Methods in Molecular Biology, vol. 814, DOI 10.1007/978-1-61779-452-0_13, Springer Science+Business Media, LLC 2012.

Weightman et al., NanoMed Nanotechnol. Bio. Med. 2014; 10:291-295 published online on Oct. 1, 2013; doi. org/10.1016/j.nano .2013.09.001.

East et al., "Alignment of Astrocytes Increases Neuronal Growth in 3D Collagen Gels and is Maintained Following Plastic Compression to Form a Spinal Cord Repair Conduit," Tissue Eng. Part A, 2010; 16:3173-3184.

Cullen et al., "Microtissue Engineered Constructs with Living Axons for Targeted Nervous System Reconstruction," Tissue Eng. Part A, 2012; 18:2280-2289.

Balasubramanian et al., "Three-Dimensional Environment Sustains Morphological Heterogeneity and Promotes Phenotypic Progression During Astrocyte Development," Tissue Engineering: PartA, 2016; 22:885-898.

Brown et al., "Ultrarapid Engineering of Biomimetic Materials and Tissues: Fabrication of Nano- and Microstructures by Plastic Compression," Adv. Funct. Mat. 2005; 15:1762-1770.

Tibbitt et al., "Hydrogels as Extracellular Matrix Mimics for 3D Cell Culture," Biotechnol. Bioeng. 2009; 103:655-663.

Yucel et al., "Tissue Engineered, Guided Nerve Tube Consisting of Aligned Neural Stem Cells and Astrocytes," Biomacromolecules, 2010; 11:3584-3591.

International Search Report and Written Opinion for PCT International Application No. PCT/US2015/065353 issued Mar. 7, 2016.

Cullen, et al., "In vitro neural injury model for optimization of tissue-engineered constructs", J. Neurosci Res. 85 (16) ,2007 ,3642-3651 (Abstract Only).

Lau, et al.,"3D Electrospun scaffolds promote a cytotrophic phenotype of cultured primary astrocytes", J Neurochem. 130(2) ,2014,215-226.

McCarthy, et al., "Preparation of separate astroglial and oligodendroglial cell cultures from rat cerebral tissue", J Cell Biol. 85(3) , 1980 ,890-902.

Shimizu, et al., "Cell sheet engineering for myocardial tissue reconstruction", Biomaterials. 24(13) ,2003 ,2309-2316.

Struzyna, et al., "Living scaffolds for neuroregeneration", Curr Opin Solid State Mater Sci. 18(6) ,2014 ,308-318.

Zheng, et al., "Tensile regulation of axonal elongation and initiation", J Neurosci. 11(4), 1991 ,1117-1125.

International Search Report and Written Opinion, PCT/US2018/ 054576, dated Dec. 12, 2018.

Huang , et al., "Long-term survival and integration of transplanted engineered nervous tissue constructs promotes peripheral nerve regeneration", Tissue Eng Part A, 15(7), 1677-1685 (Jul. 2009) (Abstract only).

Loverde, Joseph R. , "Deciphering the biology of axon stretch-growth", New Jersey Institute of Technology, Digital Commons @ NJIT, Theses 297, submitted to the Faculty of New Jersey Institute of Technology, Jan. 2009, 63 pages.

Pfister , et al., "Extreme stretch growth of integrated axons", J Neurosci, 24(36), 7978-7983 (Sep. 2004).

Smith , et al., "A new strategy to produce sustained growth of central nervous system axons: continuous mechanical tension", Tissue Eng 7, 131-139 (2001) (Abstract only).

International Search Report and Written Opinion dated Apr. 14, 2020, PCT/US19/60585.

Czajka , et al., "Implanted scaffold-free prevascularized constructs promote tissue repair", Ann Plast Surg., Mar. 2015; 74(3): 371-375.

Graber , et al., "Purification and Culture of Spinal Motor Neurons from Rat Embryos", Downloaded from http://cshprotocols.cshlp. org/on Jul. 26, 2021—Published by Cold Spring Harbor Laboratory Press.

Katiyar , et al., "Stretch-Growth of Motor Axons in Custom Mechanobioreactors to Generate Long-Projecting Axonal and Axonal-Myocyte Constructs", bioRxiv, preprint doi: https://doi.Org/10.1101/ 598755; Apr. 4, 2019.

Kimura , et al., "Development, Maturation, and Transdifferentiation of Cardiac Sympathetic Nerves", Circ Res. Jan. 20, 2012;110(2):325-36, doi: 10.1161/CIRCRESAHA.111.257253. PMID: 22267838.

Kreipke , et al., "Innervating sympathetic neurons regulate heart size and the timing of cardiomyocyte cell cycle withdrawal", J Physiol 593.23 (Sep. 2015) pp. 5057-5073.

Ng , et al., "Three-dimensional fibrous scaffolds with microstructures and nano textures for tissue engineering", RSC Advances; Aug. 2012, 2, 10110-10124.

O'Donnell , et al., "A tissue-engineered rostral migratory stream for directed neuronal replacement", Neural Regeneration Research, Aug. 2018, vol. 13, No. 8, pp. 1327-1331.

Oh , et al., "Functional Coupling with Cardiac Muscle Promotes Maturation of hPSC-Derived Sympathetic Neurons", Cell Stem Cell, 19, 95-106, Jul. 7, 2016.

Potter , et al., "Synaptic Functions in Rat Sympathetic Neurons in Microcultures. II. Adrenergic/Cholinergic Dual Status and Plasticity", The Journal of Neuroscience, Apr. 1986, vol. 6, No. 4, pp. 1080-1098.

Rodell , et al., "Injectable and Cytocompatible Tough Double Network Hydrogels through Tandem Supramolecular and Covalent Crosslinking", Adv Mater., Oct. 2016; 28(38): 8419-8424. doi:10. 1002/adma.201602268.

Serruya , et al., "Cardiac myocyte microtissue aggregates broadcast local field potentials", bioRxiv, preprint doi: https://doi.org/10.1101/ 376418; Jul. 25, 2018.

Struzyna , et al., "Rebuilding Brain Circuitry with Living Micro-Tissue Engineered Neural Networks", Tissue Engineering: Part A, vol. 21, Nos. 21 and 22, 2015.

BRAIN Initiative Investigators Pre-Meeting: Large Scale Recording and Modulation, Dec. 9, 2015, Rockville, MD.

Extended European Search Report for European Patent Application No. 17783279.7 issued Oct. 11, 2019.

International Search Report and Written Opinion for PCT/US2017/ 027705 issued Sep. 1, 2017.

Abate, T. , "Stanford engineers create artificial skin that can send pressure sensation to brain cell", Stanford Report, Oct. 15, 2015, 4 pages.

Anikeeva, P. , "Flexible Optoelectronic Devices for Neural Recording and Stimulation", Flexible Electronics Session, NAE USFOE, 2013, 13 pages.

Aregueta-Robles , et al., "Organic electrode coatings for next-generation neural interfaces", Front Neuroeng. 7:15, May 2014, 15.

Chen, H. I., et al., "Neural Substrate Expansion for the Restoration of Brain Function", Frontiers in Systems Neuroscience, vol. 10(1), Jan. 2016, 9 pages.

Choi, M. , et al., "Light-guiding hydrogels for cell-based sensing and optogenetic synthesis in vivo", Nat Photonics, 7, 2013, 987-994.

Colapinto, J. , "Lighting the Brain", Profiles, May 18, 2015, 16 pags.

Cullen, D. K., et al., "Microtissue Engineered Constructs with Living Axons for Targeted Nervous System Reconstruction", Tissue Engineering: Part A, vol. 18(21,22), 2012, 2280-2289.

(56) References Cited

OTHER PUBLICATIONS

Deisseroth, K., et al., "Engineering Approaches to Illuminating Brain Structure and Dynamics", Neuron 80, Oct. 30, 2013, 568-577.
Jeong, J., et al., "Soft Materials in Neuroengineering for Hard Problems in Neuroscience", Neuron 86, Apr. 8, 2015, 175-186.
Long, X., et al., "Magnetogenetics: remote non-invasive magnetic activation of neuronal activity with a magnetoreceptor", Science Bulletin 60(24), Dec. 2015, 2107-2119.
NIH, "Biological 'Living Electrodes' using Tissue Engineered Axonal Tracts to Probe and Modulate the Nervous System", NIH Research Portfolio Online Reporting Tools (RePORT), Dec. 29, 2015, 1 page.
Smith, K., "Method Man—Karl Delsseroth is leaving his mark on brain science one technique at a time", Nature, vol. 497, May 30, 2013, 550-552.
Struzyna, L. A., et al., "Restoring nervous system structure and function using tissue engineered living scaffolds", Neural Regeneration Research, vol. 10(5), May 2015, 679-685.
Tang-Schomer, M. D., et al., "Bioengineered functional brain-like cortical tissue", PNAS, vol. 111(38), Sep. 23, 2014, 13811-13816.
International Search Report and Written Opinion issued in App. No. PCT/US2022/017470, mailing date Jun. 22, 2022, 13 pages.
International Search Report and Written Opinion issued in App. No. PCT/US22/32978, mailing date Oct. 27, 2022, 17 pages.
International Search Report and Written Opinion issued in App. No. PCT/US2022/029908, mailing date Oct. 27, 2022, 12 pages.
International Search Report and Written Opinion issued in App. No. PCT/US2022/032146, mailing date Sep. 14, 2022, 15 pages.
International Search Report and Written Opinion issued in App. No. PCT/US 2023/013385, mailing date May 2, 2023, 10 pages.
Adewole et al., "Development of optically controlled "living electrodes" with long-projecting axon tracts for a synaptic brain-machine interface", Science Advances, vol. 7, Jan. 22, 2021 [retrieved on Sep. 16, 2022]. Retrieved from the Internet: URL: https://www.science.org/doi/10.1126/sciadv.aay5347>. pp. 1-15.
Gordian-Velez et al., "Restoring lost nigrostriatal fibers in Parkinson's disease based on clinically-inspired design criteria", Brain Research Bulletin, vol. 175, Jul. 28, 2021, pp. 168-185.
Kim et al. "Gingiva-Derived Mesenchymal Stem Cells: Potential Application in Tissue Engineering and Regenerative Medicine—a Comprehensive Review", Frontiers in Immunology, Apr. 16, 2021, vol. 12, Article No. 667221, pp. 1-25.
Clark et al. "In Vivo Neural Tissue Engineering: Cylindrical Biocompatible Hydrogels That Create New Neural Tracts in the Adult Mammalian Brain", Stem Cells and Development, Jun. 2016, vol. 25, No. 15, pp. 1109-1118.
Purvis et al. "Tissue Engineering and Biomaterial Strategies to Elicit Endogenous Neuronal Replacement in the Brain", Frontiers in Neurology, Apr. 28, 2020, vol. 11, Article No. 344.
O'Donnell et al. "An Implantable Human Stem Cell-Derived Tissue-Engineered Rostral Migratory Stream for Directed Neuronal Replacement", Nature Communications Biology, Jul. 15, 2021, vol. 4, Article No. 879.
Barbour, et al., "Supercharged End-to-Side Anterior Interosseous to Ulnar Motor Nerve Transfer for Intrinsic Musculature Reinnervation", J Hand Surg. 37(10), 2012, 2150-2159.
Farber, et al., "Supercharge Nerve Transfer to Enhance Motor Recovery", J Hand Surg. 38(3), 2013, 466-477.
Gordon, et al., "Accelerating Axon Growth to Overcome Limitations in Functional Recovery after Peripheral Nerve Injury", Neurosurgery 65(4), 2009, A132-A144.
Gordon, et al., "Brief electrical stimulation accelerates axon regeneration in the peripheral nervous system and promotes sensory axon regeneration in the central nervous system", Motor Control 13(4), 2009, 412-441.
Gordon, et al., "The Basis for Diminished Functional Recovery after Delayed Peripheral Nerve Repair", J Neurosci. 31 (14), 2011, 5325-5334.
Gordon, "The physiology of neural injury and regeneration: The role of neurotrophic factors", J Commun Disord. 43(4), 2010, 265-273.
Ladak, et al., "Side-to-side nerve grafts sustain chronically denervated peripheral nerve pathways during axon regeneration and result in improved functional reinnervation", Neurosurgery 68(6), 2011, 1654-1666.
Midha, et al., "Regeneration into Protected and Chronically Denervated Peripheral Nerve Stumps", Neurosurgery 57 (6), 2005, 1289-1299.
Scholz, et al., "Peripheral nerve injuries: an international survey of current treatments and future perspectives", J Reconstructive Microsurgery 25(6), 2009, 339-344.
Smith, et al., "Stretch Growth of Integrated Axon Tracts: Extremes & Exploitations", Progress in Neurobiology 89 3), 2009, 231-239.
Sulaiman, et al., "Role of Chronic Schwann Cell Denervation in Poor Functional Recovery after Nerve Injuries and Experimental Strategies to Combat It", Neurosurgery 65(4), 2009, A105-A114.
Pfister, et al., "Development of transplantable nervous tissue constructs comprised of stretch-grown axons", J Neurosci Methods. 153(1), 2006, 95-103.
Jiang et al., "Stem Cell Transplantation for Peripheral Nerve Regeneration: Current Options and Opportunities," Int J Mol Sci. Jan. 5, 2017;18(1). pii: E94.
Cullen et al., "Collagen-Dependent Neurite Outgrowth and Response to Dynamic Deformation in 3D Neuronal Cultures," Ann. Biomed. Engin. 2007; 35:835-846.
Xu et al., "Electrophysiological characterization of embryonic hippocampal neurons cultured in a 3D collagen hydrogel," Biomaterials 2009; 30:4377-4383.
Struzyna et al., "Tissue Engineered Nigrostriatal Pathway for Treatment of Parkinson's Disease," J. Tissue Engin. & Regen. Med. 2018; 12:1702-1716.
Henstridge et al., "Beyond the neuron-cellular interactions early in Alzheimer disease pathogenesis," Nat. Rev. Neurosci. 2019; 20:94-107.
Anger, "Animal Test Systems to Study Behavioral Dysfunctions of Neurodegenerative Disorders," (p. 403, abstract, Neurotoxicology, 1991; 12:403-13.
Blight, "Miracles and molecules-progress in spinal cord repair," Nat. Neurosci. 2002. 5: 1051-4.
Schmidt et al., "Neural Tissue Engineering: Strategies for Repair and Regeneration," Annu. Rev. Biomed. Eng. 2003. 5: 293-347.
Hoke et al., "Mechanisms of Disease: what factors limit the success of peripheral nerve regeneration in humans?" Nat. Clin. Pract. Neurol. 2006: 448-454.
Belal, et al., "Pathology as it relates to ear surgery II. Labyrinthectomy", J Laryngol Otol, 97(1), 1983, 1-10.
Borisoff, et al., "Suppression of Rho-kinase activity promotes axonal growth on inhibitory CNS substrates", Mol Cell NeurOsci, 22(3), 2003, 405-416.
Cheng, et al., "Clinical progression in Parkinson disease and the neurobiology of axons", Ann Neurol, 67(6), 2010, 715-725.
Curinga, et al., "Molecular/genetic manipulation of extrinsic axon guidance factors for CNS repair and regeneration", Exp Neurol, 209(2), 2008, 333-342.
Denham, et al., "Neurons derived from human embryonic stem cells extend long-distance axonal projections through growth along host white matter tracts after intra-cerebral transplantation", Front Cell Neurosci 6, 2012,11.
Diamond, et al., "'Where' and 'what' in the whisker sensorimotor system", Nat Rev Neurosci, 9(8), 2008, 601-612.
Fawcett, "Dopaminergic neuronal survival and the effects of bFGF in explant, three dimensional and monolayer Cultures of embryonic rat ventral mesencephalon", Exp Brain Res, 106(2), 1995,275-282.
Filous, et al., "Immature astrocytes promote CNS axonal regeneration when combined with chondroitinase ABC", Dev Neurobiol, 70(12), 2010, 826-841.
Hennink, et al., "Novel crosslinking methods to design hydrogels", Adv. Drug Del. Rev. 54,2002, 13-36.
Hoffman, "Hydrogels for biomedical applications", Adv. Drug Del. Rev. 43,2002, 3-12.
Huebner, et al., "Axon regeneration in the peripheral and central nervous systems", Results Probl Cell Differ 48, 2009, 339-351.

(56) References Cited

OTHER PUBLICATIONS

Hwang, et al., "Chondrogenic Differentiation of Human Embryonic Stem Cell-Derived Cells in Arginine-Glycine-Aspartate-Modified Hydrogels", Tissue Eng. 12, 2006, 2695-706.
Ifkovits, et al., "Review: Photopolymerizable and Degradable Biomaterials for Tissue Engineering Applications", Tissue Eng. 13(10), 2007, 2369-85.
Kim, et al., "Association between sociability and diffusion tensor imaging in BALB/cJ mice", NMR in Biomedicine, 25 1), 2012, 104-112.
Kim, et al., "Enhanced delineation of white matter structures of the fixed mouse brain using Gd-DTPA in microscopic MRI", NMR in Biomedicine, 22(3), 2009, 303-309.
Kunze, et al., "Micropatterning neural cell cultures in 3D with a multi-layered scaffold", Biomaterials, 32(8), 2011, 2088-2098.
Lavallee, "Feedforward Inhibitory Control of Sensory Information in Higher-Order Thalamic Nuclei", J Neurosci, 25 33), 2005, 7489-7498.
Learoyd, et al., "Comparison of rat sensory behavioral tasks to detect somatosensory morbidity after diffuse brain-injury", Behav Brain Res, 226(1), 2012, 197-204.
Levin, et al., "A clinicopathologic study of optic neuropathies associated with intracranial mass lesions with quantification of remaining axons", Am J Ophthalmol, 95(3), 1983,295-306.
Marshall, et al., "Deep white matter infarction: correlation of MR imaging and histopathologic findings", Radiology, 167(2), 1988, 517-522.
Masri, et al., "Zona Incerta: a Role in Central Pain", J Neurophysiol, 102(1), 2009,181-191.
McNamara, et al., "The Whisker Nuisance Task Identifies a Late-Onset, Persistent Sensory Sensitivity in Diffuse Brain-Injured Rats", J Neurotrauma, 27(4), 2010, 695-706.
Melzer, et al., "Stimulus Frequency Processing in Awake Rat Barrel Cortex", J Neuorsci, 26(47), 2006,12198-12205.
Millet, et al., "Guiding neuron development with planar surface gradients of substrate cues deposited using miicrofluidic devices", Lab Chip, 10(12), 2010,1525-1535.
Mine, et al., "Grafted human neural stem cells enhance several steps of endogenous neurogenesis and improve behavioral recovery after middle cerebral artery occlusion in rats", Neurobiol Dis 52:, 2013,191-203.
Nam, et al., "Multichannel recording and stimulation of neuronal cultures grown on microstamped poly-D-lysine", Conf Proc IEEE Eng Med Biol Soc. 6:, 2004, 4049-52.
Nguyen, et al., "Photopolymehzable hydrogels for tissue engineering applications", Biomaterials 23(22), 2002, 4307-14.
O'Connor, et al., "Survival and neurite outgrowth of rat cortical neurons in three-dimensional agarose and collagen gel matrices", Neurosci Lett, 304(3), 2001,189-193.
Qiu, et al., "Photoreceptor differentiation and integration of retinal progenitor cells transplanted into transgenic rats", Exp Eye Res, 80(4), 2005, 515-525.
Das, Suradip, et al., "Innervation: the missing link for biofabricated tissues and organs", Regenerative Medicine (2020) 5:11 ; https://doi.org/10.1038/s41536-020-0096-1.
Das, Suradip, et al., "Pre-innervated tissue-engineered muscle promotes a pro-regenerative microenvironment following volumetric muscle loss", Communications Biology, (2020), 3:330, https://doi.org/10.1038/ s42003-020-1056-4, www.nature.com/commsbio.
Ungrin , et al., "Reproducible, Ultra High-Throughput Formation of Multicellular Organization from Single Cell Suspension-Derived Human Embryonic Stem Cell Aggregates", PLoS ONE, Feb. 2008, vol. 3, Issue 2, e1565.
Vegh , et al., "Part and Parcel of the Cardiac Autonomic Nerve System: Unravelling Its Cellular Building Blocks during Development", J. Cardiovasc. Dev. Dis., Sep. 2016, 3, 28.
Zareen , et al., "Protocol for Culturing Sympathetic Neurons from Rat Superior Cervical Ganglia (SCG)", J. Vis. Exp. (23), e988, doi: 10.3791/988 (Jan. 2009).

Extended European Search Report issued in App. No. EP23164337, dated Jun. 16, 2023, 9 pages.
A.: "BRAIN Initiative Investigators Pre-meeting: Large Scale Recording and Modulation", Dec. 9, 2015 (Dec. 9, 2015), XP055628498, Retrieved from the Internet: URL:https://web.math.princeton.eduhsswang/Electrodes_Presentations_BRAIN_Large_Scale_Recording_Modulation.pdf [retrieved on Oct. 3, 2019].
Pfister et al., "Development of transplantable nervous tissue constructs comprised of stretch-grown axons", Journal of Neuroscience Methods, vol. 153, (2006), pp. 95-103.
McGill, The McGill Physiology Virutal Lab, Accessed Aug. 22, 23, Available online at: www.medicine.cgill.ca/physio/vlab/other_exps CAP/nerve_anat.htm#:-:text=For%20example%2C%20the%20vagus%20nerve,ganglia%20%20for%20sensory%20fibres.
Popa-Wagner, A. et al., "Effects of Granulocyte-Colony Stimulating Factor After Stroke in Aged Rats", Stroke 41, 1027-1031 (2010).
Erlandsson, et al., "Immunosuppression promotes endogenous neural stem and progenitor cell migration and tissue regeneration after ischemic injury", Experimental Neurology 230, 48-57 (2011).
Yu, et al., "Local administration of AAV-BDNF to subventricular zone induces functional recovery in stroke rats", PloS one 8, e81750 (2013).
Gundelach, et al., "Redirection of neuroblast migration from the rostral migratory stream into a lesion in the prefrontal cortex of adult rats", Experimental brain research 236, 1181-1191 (2018).
Jinnou, H. et al., "Radial Glial Fibers Promote Neuronal Migration and Functional Recovery after Neonatal Brain injury", Cell stem cell 22, 128-137, (2018).
Adewole, et al., "Scaffolds for brain tissue reconstruction", in Handbook of Tissue Engineering Scaffolds: vol. Two 3-29 (Elsevier, 2019). doi:10.1016/B978-0-08-102561-1.00001-4.
Katiyar, et al., "Stretch growth of motor axons in custom mechanobioreactors to generate long-projecting axonal constructs", Journal of Tissue Engineering and Regenerative Medicine 13, 2040-2054 (2019).
Winter, C. C. et al., "Transplantable living scaffolds comprised of micro-tissue engineered aligned astrocyte networks to facilitate central nervous system regeneration", Acta biomaterialia 38, 44-58 (2016).
Katiyar, K. S. et al., "Three-dimensional Tissue Engineered Aligned Astrocyte Networks to Recapitulate Developmental Mechanisms and Facilitate Nervous System Regeneration", Journal of visualized experiments : JoVE (2018) doi:10.3791/55848.
Ganz, J. et al., "Astrocyte-like cells derived from human oral mucosa stem cells provide neuroprotection in vitro and in vivo", Stem cells translational medicine 3, 375-86 (2014).
Panzer, K. V. et al., "Tissue Engineered Bands of Büngner for Accelerated Motor and Sensory Axonal Outgrowth", Front. Bioeng. Biotechnol. 8, (2020).
Lois, et al., "Long-distance neuronal migration in the adult mammalian brain", Science 264, 1145-1148 (1994).
Mn, X. et al., "Neurons Derived from Human Induced Pluripotent Stem Cells Integrate into Rat Brain Circuits and Maintain Both Excitatory and Inhibitory Synaptic Activities", eNeuro 6, ENEURO.0148-19.2019 (2019).
Rolfe, et al., "Stem Cell Therapy in Brain Trauma: Implications for Repair and Regeneration of Injured Brain in Experimental TBI Models", in Brain Neurotrauma: Molecular, Neuropsychological, and Rehabilitation Aspects. (ed. Kobeissy, F. H.) (CRC Press/Taylor & Francis, 2015).
Yamashita, T. et al., "Novel Therapeutic Transplantation of Induced Neural Stem Cells for Stroke", Cell transplantation 26, 461-467 (2017).
Xiong, L. L. et al., "Neural Stem Cell Transplantation Promotes Functional Recovery from Traumatic Brain Injury via Brain Derived Neurotrophic Factor-Mediated Neuroplasticity", Molecular Neurobiology 55, 2696-2711 (2018).
Kim, K. et al., "Epigenetic memory in induced pluripotent stem cells", Nature 467, 285-90 (2010).
Hickey, et al., "Using biomaterials to modulate chemotactic signaling for central nervous system repair", Biomedical Materials 13, 044106 (2018).

(56) References Cited

OTHER PUBLICATIONS

Cotman, et al., "Exercise: a behavioral intervention to enhance brain health and plasticity", Trends in Neurosciences 25, 295-301 (2002).
Griesbach, et al., "Voluntary exercise following traumatic brain injury: brain-derived neurotrophic factor upregulation and recovery of function", Neuroscience 125, 129-139 (2004).
Fon, D. et al., "Nanofibrous scaffolds releasing a small molecule BDNF-mimetic for the re-direction of endogenous neuroblast migration in the brain", Biomaterials 35, 2692-712 (2014).
Motalleb, R. et al., "In vivo migration of endogenous brain progenitor cells guided by an injectable peptide amphiphile biomaterial", Journal of tissue engineering and regenerative medicine 12, e2123-e2133 (2018).
Ajioka, I. et al., "Enhancement of neuroblast migration into the injured cerebral cortex using laminin-containing porous sponge", Tissue engineering. Part A 21, 193-201 (2015).
Fujioka, T. et al., "β1 integrin signaling promotes neuronal migration along vascular scaffolds in the post-stroke brain", EBioMedicine 16, 195-203 (2017).
Gengatharan, et al., "The Role of Astrocytes in the Generation, Migration, and Integration of New Neurons in the Adult Olfactory Bulb", Frontiers in neuroscience 10, 149 (2016).
Mason, et al., "Extracellular signals that regulate the tangential migration of olfactory bulb neuronal precursors: inducers, inhibitors, and repellents", The Journal of neuroscience, 21, 7654-63 (2001).
García-Marqués, et al., "Different astroglia permissivity controls the migration of olfactory bulb interneuron precursors", Glia 58, 218-230 (2010).
Persson, et al., "Expression of ezrin radixin moesin proteins in the adult subventricular zone and the rostral migratory stream", Neuroscience 167, 312-22 (2010).
Kaneko, N. et al., "New neurons clear the path of astrocytic processes for their rapid migration in the adult brain", Neuron 67, 213-23 (2010).
Serruya, M. D. et al., "Engineered Axonal Tracts as "Living Electrodes" for Synaptic-Based Modulation of Neural Circuitry", Advanced Functional Materials 28, 1701183 (2018).
Li, L. et al., Human Embryonic Stem Cells Possess Immune-Privileged Properties, Stem Cells 22, 448-456 (2004).
Zhang, Q. et al., "Neural Crest Stem-Like Cells Non-genetically Induced from Human Gingiva-Derived Mesenchymal Stem Cells Promote Facial Nerve Regeneration in Rats", Molecular Neurobiology 55, 6965-6983 (2018).
Zhang, Q. et al., "3D bio-printed scaffold-free nerve constructs with human gingiva-derived mesenchymal stem cells promote rat facial nerve regeneration", Scientific Reports 8, 6634 (2018).
Schindelin, J. et al., "Fiji: an open-source platform for biological-image analysis", Nature Methods 9, 676-682 (2012).
Hou, et al., "Functional Integration of Newly Generated Neurons into Striatum after Cerebral Ischemia in the Adult Rat Brain", Stroke 2008, 39, 2837-2844. https://doi.org/10.1161/STROKEAHA.107.510982.
Oliveira, et al., "Biomaterials Developments for Brain Tissue Engineering", Adv. Exp. Med. Biol. 2018, 1078, 323-346. https://doi.org/10.1007/978-981-13-0950-2_17.
Pettikiriarachchi, et al., "Biomaterials for Brain Tissue Engineering", Aust. J. Chem. 2010, 63, 1143. https://doi.org/10.1071/CH10159.
Braet, et al., "Drying Cells for SEM, AFM and TEM by Hexamethyldisilazane: a Study on Hepatic Endothelial Cells", J. Microsc. 1997, 186, 84-87. https://doi.org/10.1046/j.1365-2818.1997.1940755.x.
Peretto, et al., "Glial Tubes in the Rostral Migratory Stream of the Adult Rat", Brain Res. Bull. 1997, 42, 9-21. https://doi.org/10.1016/S0361-9230(96)00116-5.
Moshayedi, et al., "Mechanosensitivity of Astrocytes on Optimized Polyacrylamide Gels Analyzed by Quantitative Morphometry", J. Phys. Condens. Matter 2010, 22, 194114. https://doi.org/10.1088/0953-8984/22/19/194114.

Turovsky, et al., "Mechanosensory Signaling in Astrocytes", J. Neurosci. 2020, 40, 9364-9371. https://doi.org/10.1523/JNEUROSCI.1249-20.2020.
Marina, et al., "Astrocytes Monitor Cerebral Perfusion and Control Systemic Circulation to Maintain Brain Blood Flow", Nat. Commun. 2020, 11, 131. https://doi.org/10.1038/s41467-019-13956-y.
Kirby, et al., "Emerging Views of the Nucleus as a Cellular Mechanosensor", Nat. Cell Biol. 2018, 20, 373-381. https://doi.org/10.1038/s41556-018-0038-y.
Graham, et al., "Mechanotransduction and Nuclear Function", Curr. Opin. Cell Biol. 2016, 40, 98-105. https://doi.org/10.1016/j.ceb.2016.03.006.
Zimmerli, et al., "Nuclear Pores Dilate and Constrict in Cellulo", Science 2021, 374, eabd9776. https://doi.org/10.1126/science.abd9776.
Dos Santos, et al., "Regulation of Nuclear Mechanics and the Impact on DNA Damage", Int. J. Mol. Sci. 2021, 22, 3178. https://doi.org/10.3390/ijms22063178.
Versaevel, M. et al., "Spatial Coordination between Cell and Nuclear Shape within Micropatterned Endothelial Cells", Nat. Commun. 2012, 3, 671. https://doi.org/10.1038/ncomms1668.
Rougerie, et al., "Topographical Curvature Is Sufficient to Control Epithelium Elongation", Sci. Rep. 2020, 10, 14784. https://doi.org/10.1038/s41598-020-70907-0.
Ling, et al., "Pressure-Induced Changes in Astrocyte GFAP, Actin, and Nuclear Morphology in Mouse Optic Nerve"; Investig. Opthalmol. Vis. Sci. 2020, 61, 14. https://doi.org/10.1167/iovs.61.11.14.
Kalinin, et al., "Valproic Acid-Induced Changes of 4D Nuclear Morphology in Astrocyte Cells", Mol. Biol. Cell 2021, 32, mbc.E20-08-0502. https://doi.org/10.1091/mbc.E20-08-0502.
Struzyna, et al., "Anatomically Inspired Three-dimensional Microtissue Engineered Neural Networks for Nervous System Reconstruction, Modulation, and Modeling," J Vis Exp Jove e55609 (2017) doi: 10.3791/55609.
Harris, et al., "Advanced biomaterial strategies to transplant preformed micro-tissue engineered neural networks into the brain," J Neural Eng. Feb. 2016; 13(1):016019. doi: 10.1088/1741-2560/13/1/016019. Epub Jan. 13, 2016. PMID: 26760138; PMCID: PMC5541671.
Australian Examination Report No. 1 issued in App. No. AU2022215231, dated Nov. 21, 2023, 4 pages.
Zhang, et al., "Mesenchymal Stem Cells Derived from Human Gingiva Are Capable of Immunomodulatory Functions and Ameliorate Inflammation-Related Tissue Destruction in Experimental Colitis", (2009) Journal of Immunology 183:7787-7798.
Xu X., et al., "Gingivae Contain Neural-crest and Mesoderm-derived Mesenchymal Stem Cells"; (2013) J. Dent Res 92 (9): 825-832.
Zhang et al., "Human Oral Mucosa and Gingiva: a Unique Reservoir for Mesenchymal Stem Cells", (2012) J Dent Res 91(11): 1011-1018.
Siracusa, et al., "Astrocytes: role and functions in brain pathologies." Frontiers in pharmacology 10 (2019): 1114.
Matias I., et al., Astrocyte Heterogeneity: Impact to Brain Aging and Disease, (2019) Front. Aging Neurosci. 11:59.
Zhao, C., et al., "Mechanisms and functional implications of adult neurogenesis", Cell 132, 645-60 (2008).
Ming, G., et al., "Adult neurogenesis in the mammalian brain: significant answers and significant questions", Neuron 70, 687-702 (2011).
Lim, et al., "The Adult Ventricular-Subventricular Zone (V-SVZ) and Olfactory Bulb (OB) Neurogenesis", Cold Spring Harbor perspectives in biology 8, (2016).
Lledo, et al., "Origin and function of olfactory bulb interneuron diversity", Trends in neurosciences 31, 392-400 (2008).
Brill, M.S., et al., "Adult generation of glutamatergic olfactory bulb interneurons", Nature neuroscience 12, 1524-33 (2009).
Lazarini, et al., "Is adult neurogenesis essential for olfaction?" Trends in neurosciences 34, 20-30 (2011).
Nam, S.C., et al., "Dynamic features of postnatal subventricular zone cell motility: a two-photon time-lapse study", The Journal of Comparative Neurology 505, 190-208 (2007).

(56) References Cited

OTHER PUBLICATIONS

Kojima, T., et al., "Subventricular Zone-Derived Neural Progenitor Cells Migrate Along a Blood Vessel Scaffold Toward the Post-Stroke Striatum", Stem Cells N/A-N/A (2010) doi: 10.1002/stem.306.
Grade, S., et al., "Brain-derived neurotrophic factor promotes vasculature-associated migration of neuronal precursors toward the ischemic striatum", PloS one 8, e55039 (2013).
Ota, H., et al., "Speed control for neuronal migration in the postnatal brain by Gmip-mediated local inactivation of RhoA", Nature Communications 5, 4532 (2014).
Kaneko, N., et al., "Mechanisms of neuronal migration in the adult brain", Journal of neurochemistry 141, 835-847 (2017).
Dillen, et al., "Adult Neurogenesis in the Subventricular Zone and Its Regulation After Ischemic Stroke: Implications for Therapeutic Approaches", Translational stroke research (2019) doi:10.1007/s12975-019-00717-8.
Fujioka, et al., "Blood vessels as a scaffold for neuronal migration", Neurochemistry international 126, 69-73 (2019).
Kaneko, N., et al., "New neurons use Slit-Robo signaling to migrate through the glial meshwork and approach a lesion for functional regeneration", Science advances 4, eaav0618 (2018).
Cleary, et al., "Expression of ezrin in glial tubes in the adult subventricular zone and rostral migratory stream", Neuroscience 143, 851-61 (2006).
Tang, H., et al., "Effect of neural precursor proliferation level on neurogenesis in rat brain during aging and after focal ischemia", Neurobiology of Aging 30, 299-308 (2009).
Lu, et al., "Targeting Adult Neurogenesis for Poststroke Therapy", Stem cells international 2017, 5868632 (2017).
Chang, E. H., et al., "Traumatic Brain Injury Activation of the Adult Subventricular Zone Neurogenic Niche", Frontiers in Neuroscience 10, 332 (2016).
Arvidsson, et al., "Neuronal replacement from endogenous precursors in the adult brain after stroke", Nature Medicine 8, 963-70 (2002).
Parent, et al., "Rat forebrain neurogenesis and striatal neuron replacement after focal stroke", Annals of Neurology 52, 802-13 (2002).
Jin, K., et al., "Directed migration of neuronal precursors into the ischemic cerebral cortex and striatum", Molecular and Cellular Neuroscience 24, 171-189 (2003).
Thored, P., et al., "Persistent Production of Neurons from Adult Brain Stem Cells During Recovery after Stroke", Stem Cells 24, 739-747 (2006).
Thored, P., et al., "Long-term neuroblast migration along blood vessels in an area with transient angiogenesis and increased vascularization after stroke", Stroke 38, 3032-9 (2007).
Yamashita, T., et al., "Subventricular zone-derived neuroblasts migrate and differentiate into mature neurons in the post-stroke adult striatum", The Journal of Neuroscience, 26(24), 6627-36 (2006).
Liu, X. S., et al., "Gene profiles and electrophysiology of doublecortin-expressing cells in the subventricular zone after ischemic stroke", Journal of cerebral blood flow and metabolism 29, 297-307 (2009).
Kernie, S. G., et al., "Forebrain neurogenesis after focal Ischemic and traumatic brain injury", Neurobiology of disease 37, 267-74 (2010).
Young, et al., Cellular and molecular determinants of stroke-induced changes in subventricular zone cell migration. Antioxidants & redox signaling 14, 1877-88 (2011).
Lindvall, O., et al., "Neurogenesis following Stroke Affecting the Adult Brain", Cold Spring Harbor perspectives in biology 7, (2015).
Ramaswamy, et al., "Cellular proliferation and migration following a controlled cortical impact in the mouse", Brain Research 1053, 38-53 (2005).
Acosta, S. A., et al., Long-term upregulation of inflammation and suppression of cell proliferation in the brain of adult rats exposed to traumatic brain injury using the controlled cortical impact model. PloS one 8, e53376 (2013).

Mierzwa, et al., "Comparison of cortical and white matter traumatic brain injury models reveals differential effects in the subventricular zone and divergent Sonic hedgehog signaling pathways in neuroblasts and oligodendrocyte progenitors", ASN neuro 6, (2014).
Chirumamilla, et al., ":Traumatic brain injury induced cell proliferation in the adult mammalian central nervous system", Journal of neurotrauma 19, 693-703 (2002).
Chen, et al., "Neurogenesis and Glial Proliferation Persist for at Least One Year in the Subventricular Zone Following Brain Trauma in Rats", Journal of Neurotrauma 20, 623-631 (2003).
Zhang, R. L., et al., "Reduction of the Cell Cycle Length by Decreasing G1 Phase and Cell Cycle Reentry Expand Neuronal Progenitor Cells in the Subventricular Zone of Adult Rat after Stroke", Journal of Cerebral Blood Flow & Metabolism 26, 857-863 (2006).
Addington, et al., "Endogenous Repair Signaling after Brain Injury and Complementary Bioengineering Approaches to Enhance Neural Regeneration", Biomarker Insights 10s1, BMI. S20062 (2015).
Hayashi, et al., "Adult neurogenesis and its role in brain injury and psychiatric diseases", Journal of neurochemistry 147, 584-594 (2018).
Ohab, et al., "A Neurovascular Niche for Neurogenesis after Stroke", Journal of Neuroscience 26, 13007-13016 (2006).
Wang, Z., et al., "Neurogenic Niche Conversion Strategy Induces Migration and Functional Neuronal Differentiation of Neural Precursor Cells Following Brain Injury", Stem Cells and Development scd.2019.0147 (2020) doi: 10.1089/scd.2019.0147.
Kolb, B., et al., "Growth factor-stimulated generation of new cortical tissue and functional recovery after stroke damage to the motor cortex of rats", Journal of cerebral blood flow and metabolism, 27, 983-97 (2007).
Schäbitz, W. R., et al., "Intravenous Brain-Derived Neurotrophic Factor Enhances Poststroke Sensorimotor Recovery and Stimulates Neurogenesis", Stroke 38, 2165-2172 (2007).
Ma, et al., "Intranasal delivery of transforming growth factor-beta1 in mice after stroke reduces infarct volume and increases neurogenesis in the subventricular zone", BMC neuroscience 9, 117 (2008).
Petraglia, et al., "Activated protein C is neuroprotective and mediates new blood vessel formation and neurogenesis after controlled cortical impact", Neurosurgery 66, 165-71; discussion 171-2 (2010).
Ushiki, T., "Collagen Fibers, Reticular Fibers and Elastic Fibers", A Comprehensive Understanding from a Morphological Viewpoint. Arch. Histol. Cytol. 2002, 65, 109-126. https://doi.org/10.1679/aohc.65.109.
Shoulders, et al., "Collagen Structure and Stability", Annu. Rev. Biochem. 2009, 78, 929-958. https://doi.org/10.1146/annurev.biochem.77.032207.120833.
Orellana, et al., "Gap Junction Channels and Hemichannels in the CNS: Regulation by Signaling Molecules", Neuropharmacology 2013, 75, 567-582. https://doi.org/10.1016/j.neuropharm.2013.02.020.
Finkbeiner, S., "Calcium Waves in Astrocytes-Filling in the Gaps", Neuron 1992, 8, 1101-1108. https://doi.org/10.1016/0896-6273(92)90131-V.
Petrany, et al., "Cell Fusion: Merging Membranes and Making Muscle", Trends Cell Biol. 2019, 29, 964-973, https://doi.org/10.1016/j.tcb.2019.09.002.
Esfahani, et al., "Cell Shape: Effects on Gene Expression and Signaling", Biophys. Rev. 2020, 12, 895-901, https://doi.org/10.1007/s12551-020-00722-4.
Seelbinder, et al., "Nuclear Deformation Guides Chromatin Reorganization in Cardiac Development and Disease", Nat. Biomed. Eng. 2021, 5, 1500-1516. https://doi.org/10.1038/s41551-021-00823-9.
Ramdas, et al., "Cytoskeletal Control of Nuclear Morphology and Chromatin Organization", J. Mol. Biol. 2015, 427, 695-706. https://doi.org/10.1016/j.jmb.2014.09.008.
Skinner, et al., "Nuclear Morphologies: Their Diversity and Functional Relevance", Chromosoma 2017, 126, 195-212. https://doi.org/10.1007/s00412-016-0614-5.

* cited by examiner

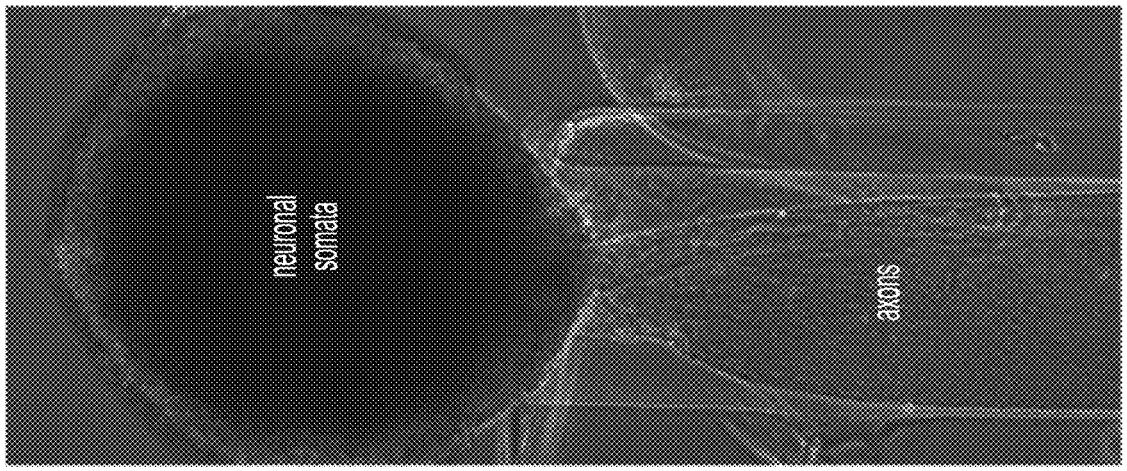
FIG. 5E
FIG. 5D
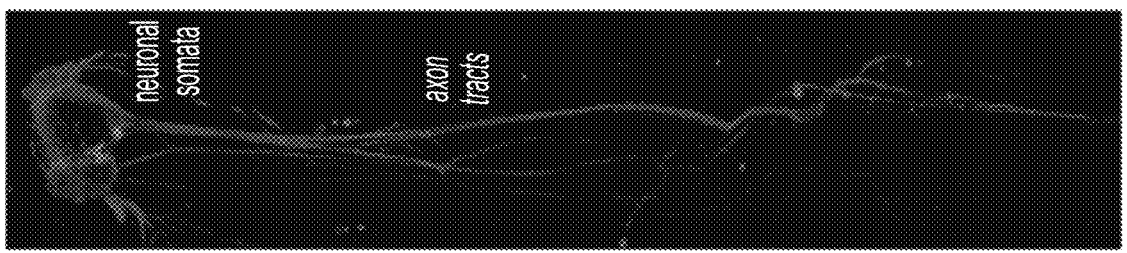
FIG. 5C
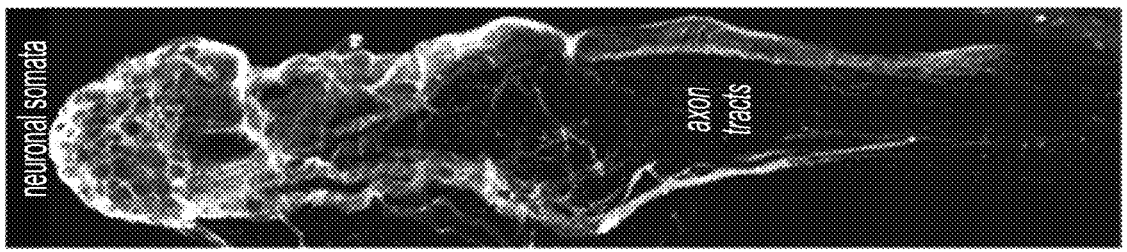
FIG. 5B
FIG. 5A
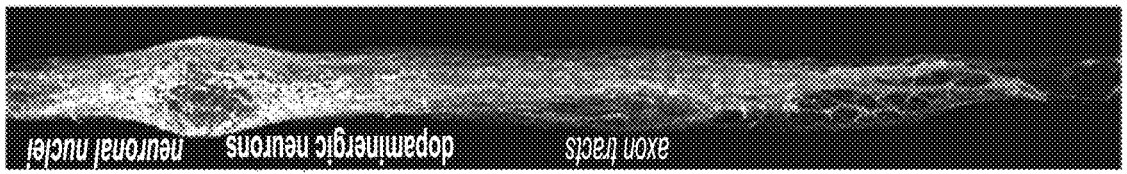

Example of bi-directional micro-TENN grown *in vitro* to 2cm in length
Neurons | Axonal Tracts

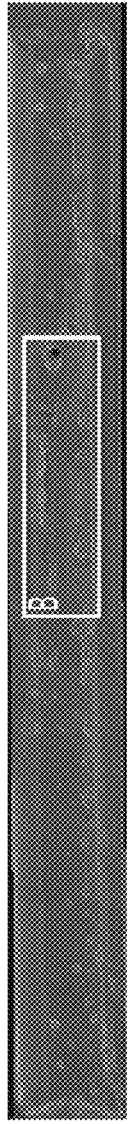
FIG. 16A
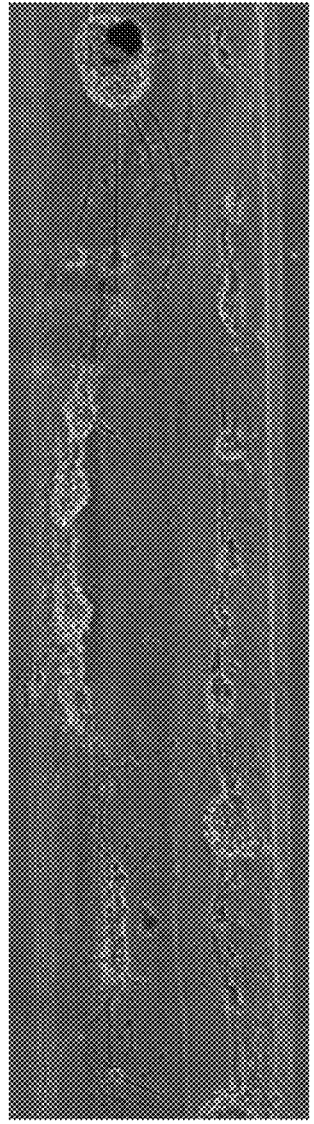
FIG. 16B
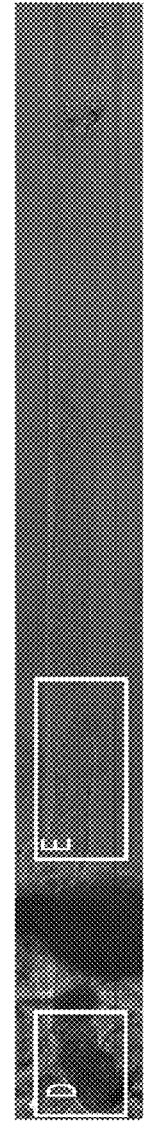
FIG. 16C
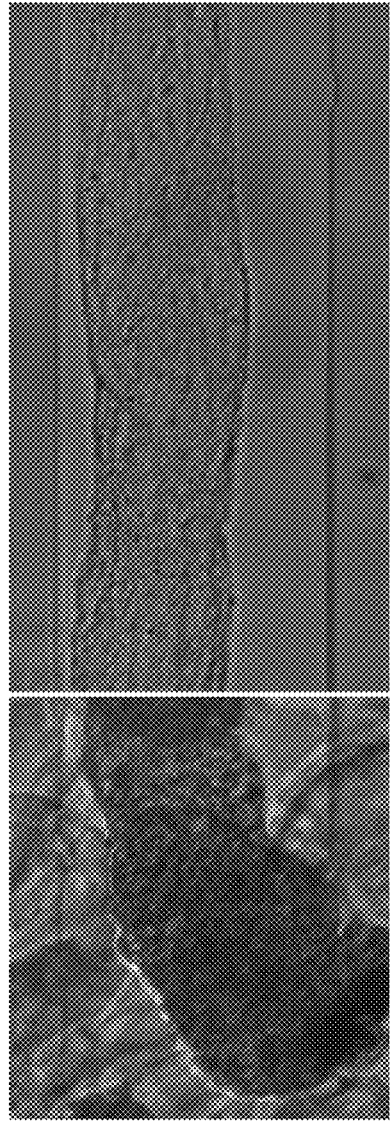
FIG. 16E
FIG. 16D

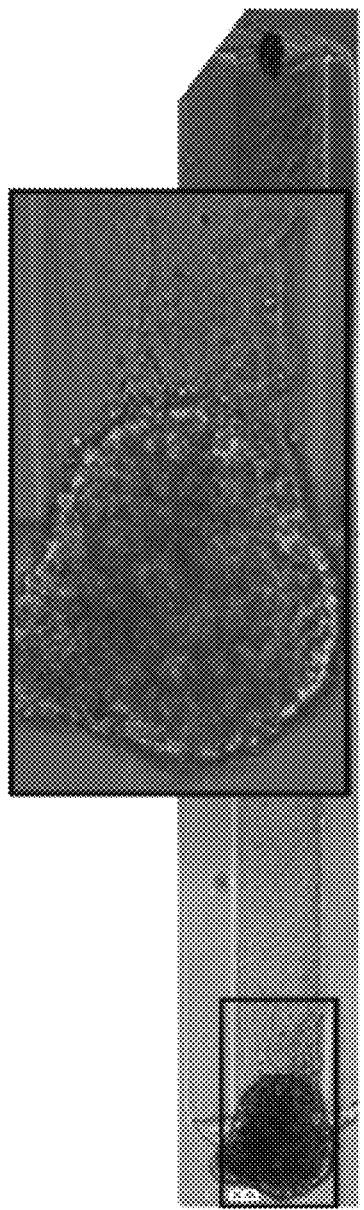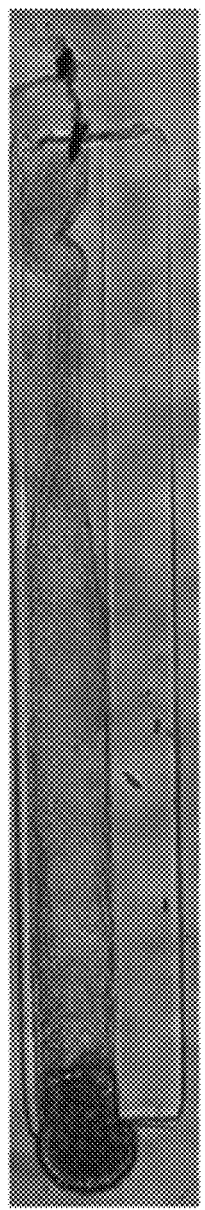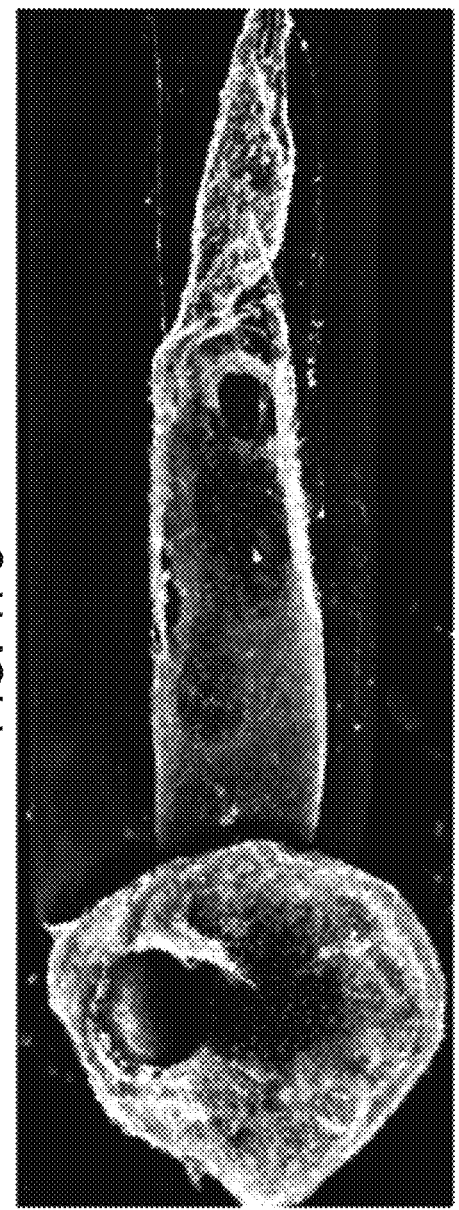

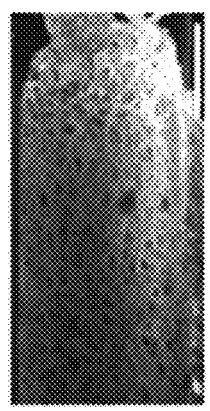
FIG. 19a'
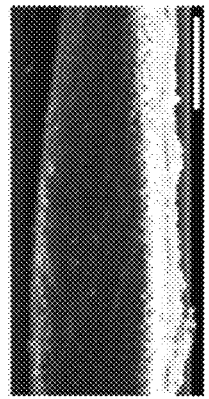
FIG. 19a"
FIG. 19A
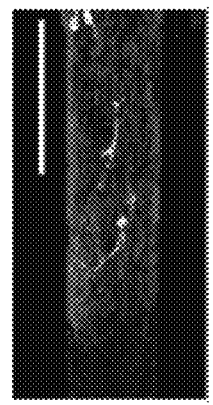
FIG. 19b'
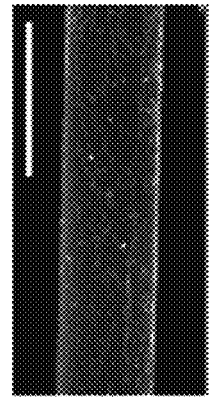
FIG. 19b"
FIG. 19B FIG. 23A1
FIG. 23A2
FIG. 23A3
FIG. 23B
FIG. 23C
   
FIG. 23D1   FIG. 23D2   FIG. 23D3   FIG. 23D4
FIG. 23E1
FIG. 23E2
FIG. 23E3
FIG. 23E4
FIG. 23F1   FIG. 23F2
FIG. 23F3   FIG. 23F4
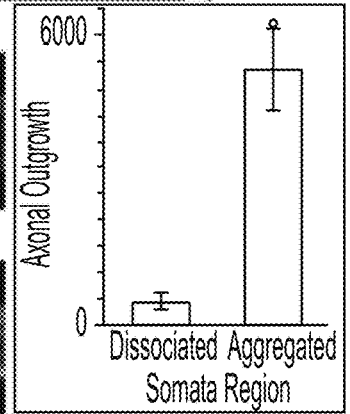
FIG. 23G

FIG. 24A1
FIG. 24A2
FIG. 24A3
FIG. 24B1
FIG. 24B2
FIG. 24B3
FIG. 24C1
FIG. 24C2
FIG. 24C3
FIG. 24D1
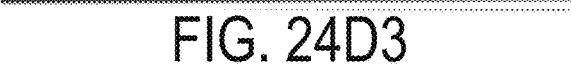
FIG. 24D2
FIG. 24D3

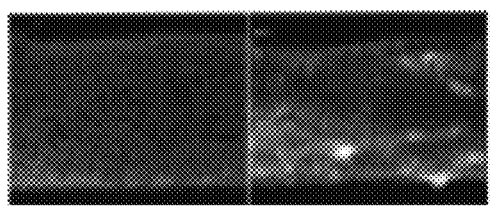
FIG. 24a1    FIG. 24a2
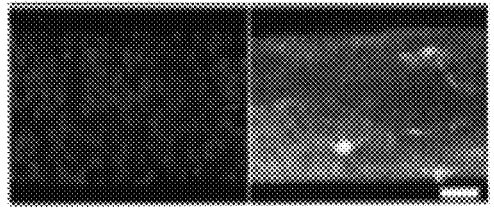
FIG. 24a3    FIG. 24a4
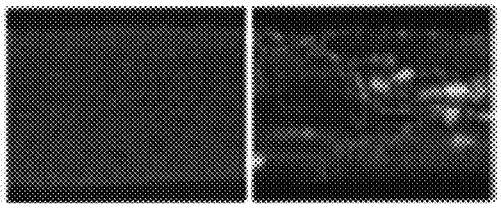
FIG. 24c1    FIG. 24c2
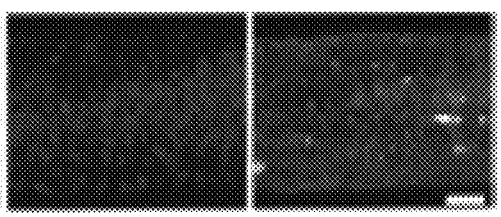
FIG. 24c3    FIG. 24c4
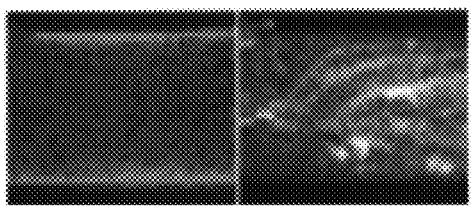
FIG. 24b1    FIG. 24b2
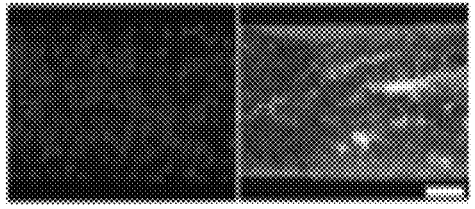
FIG. 24b3    FIG. 24b4
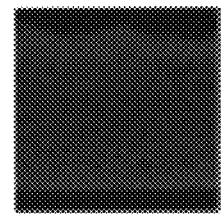 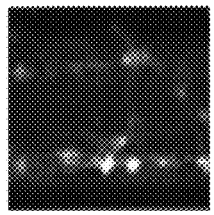
FIG. 24d1    FIG. 24d2
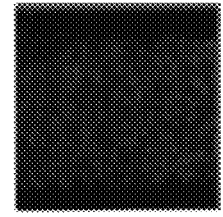 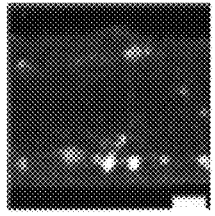
FIG. 24d3    FIG. 24d4
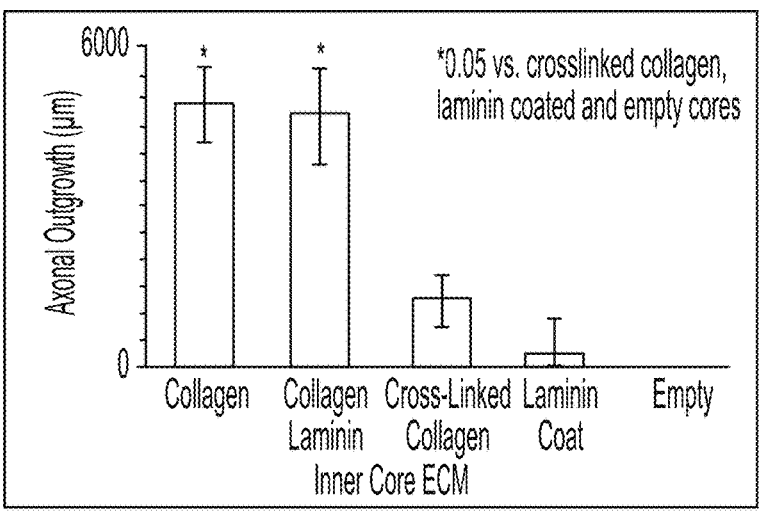
FIG. 24E
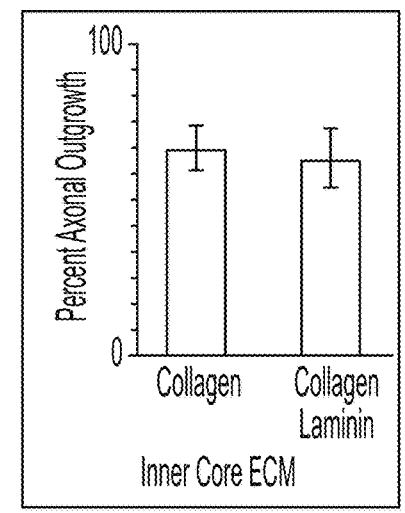
FIG. 24F FIG. 25A
FIG. 25B
FIG. 25C
FIG. 25D
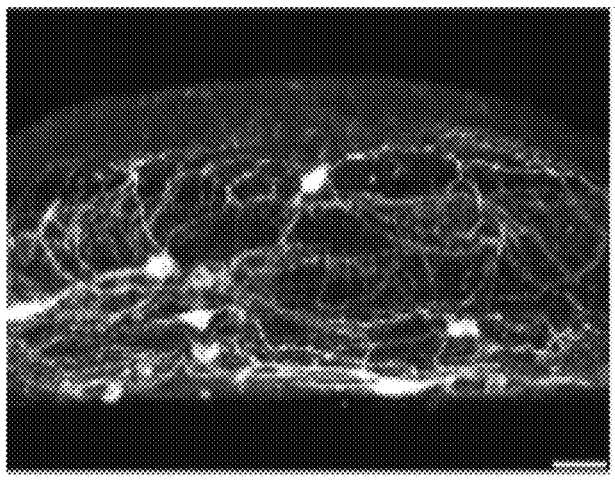
FIG. 25E
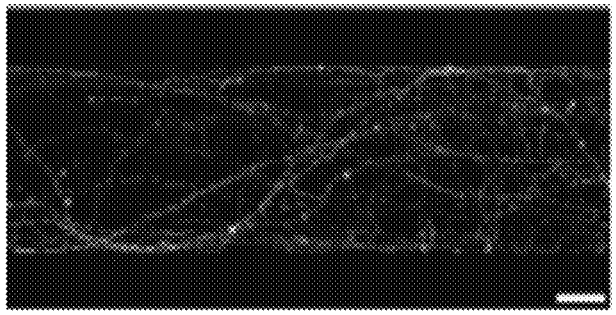
FIG. 25F
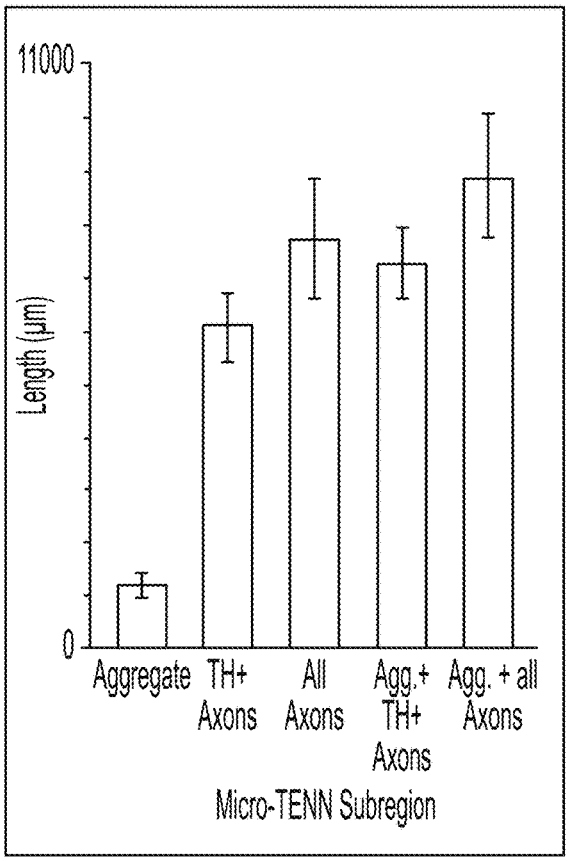
FIG. 25G

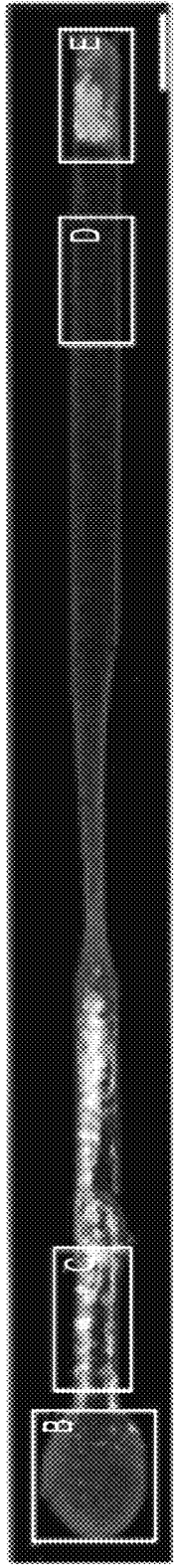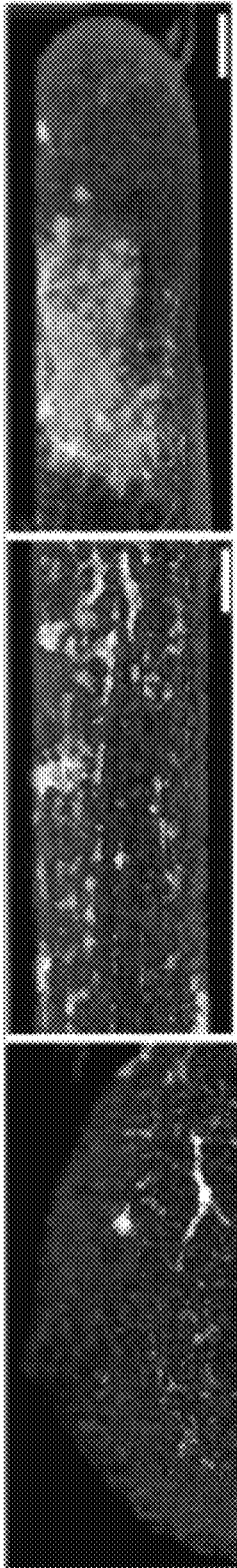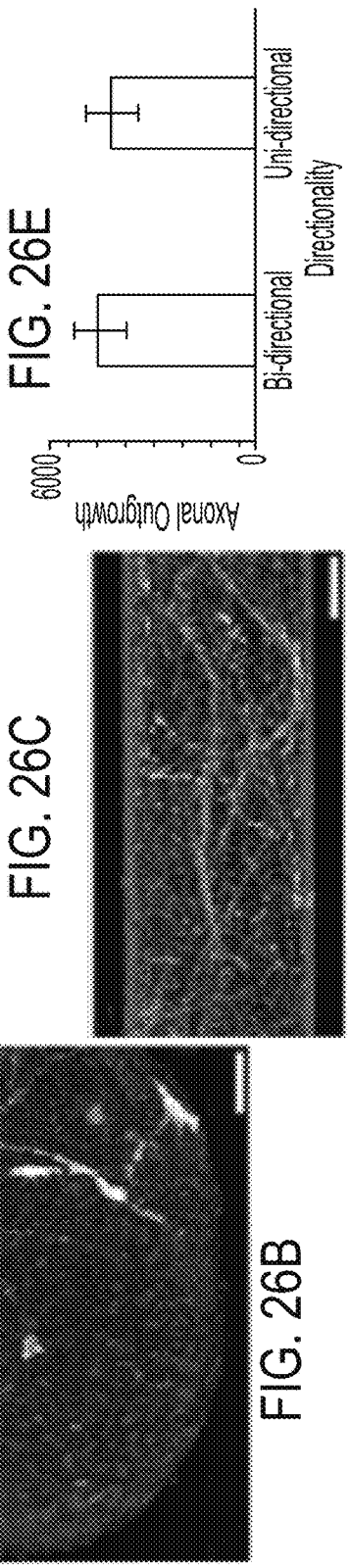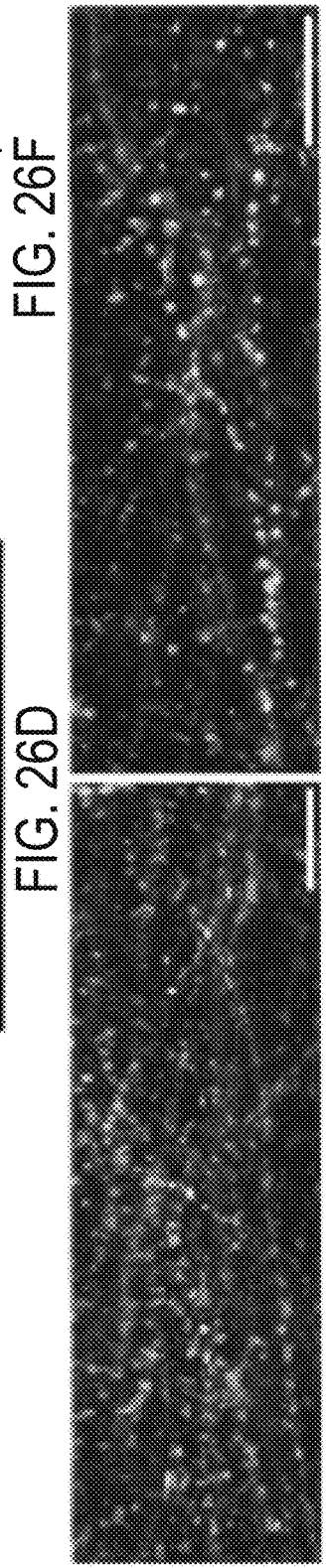
FIG. 26A FIG. 26B FIG. 26C FIG. 26D FIG. 26E FIG. 26F FIG. 26G FIG. 26H

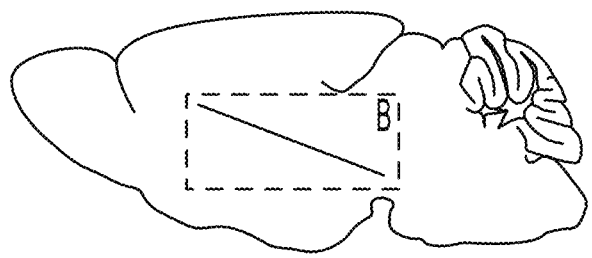
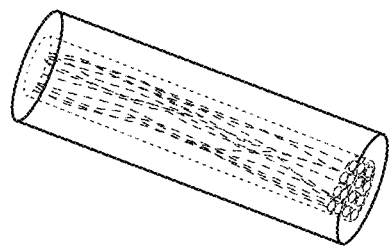
FIG. 27A　　　　FIG. 27B
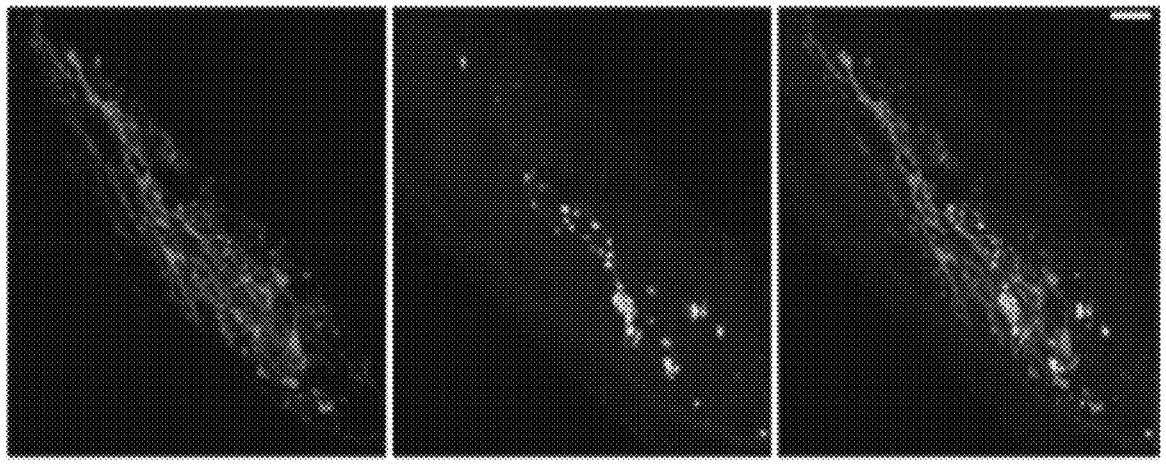
FIG. 27C
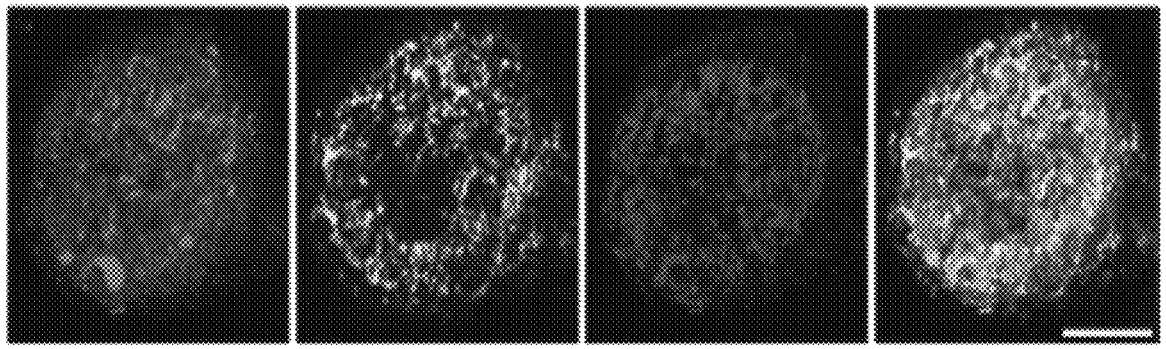
FIG. 27D

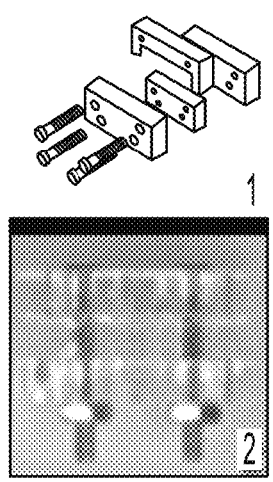
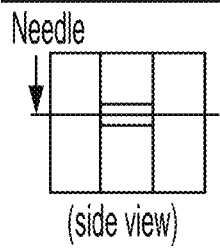
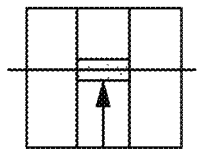
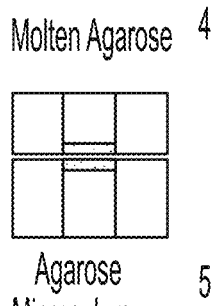
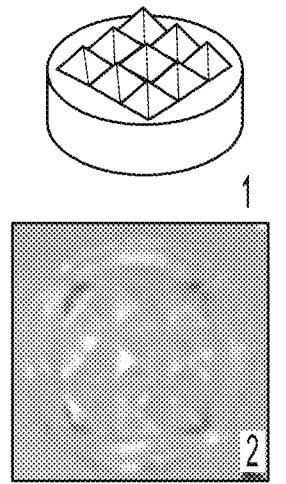
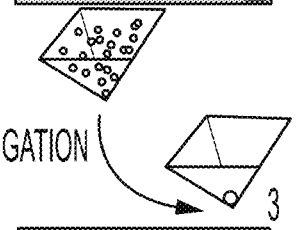
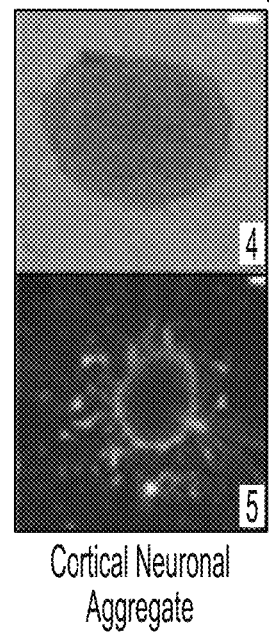
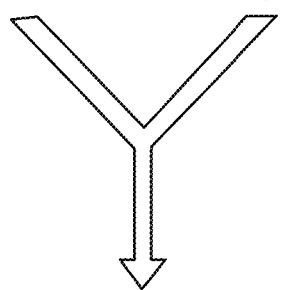
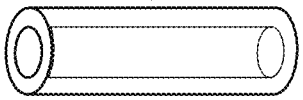
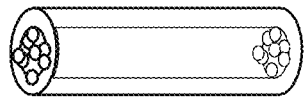
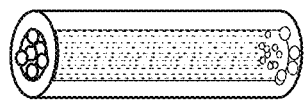
FIG. 29A     FIG. 29B     FIG. 29C

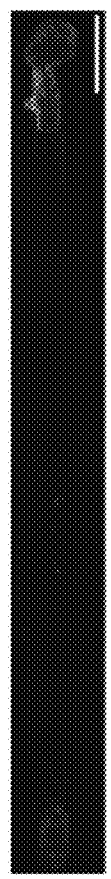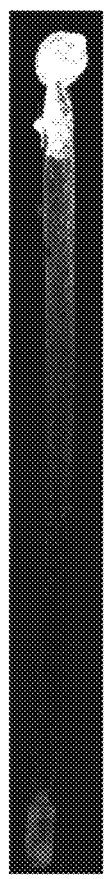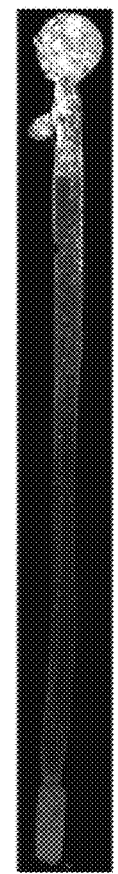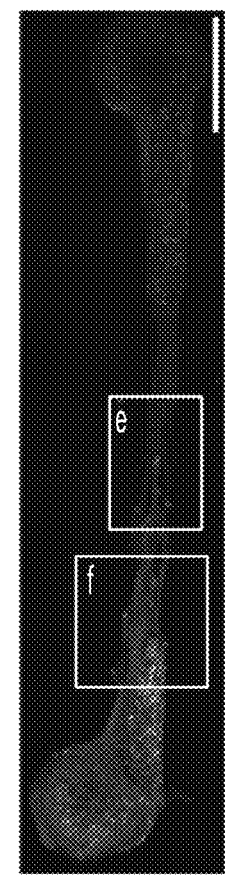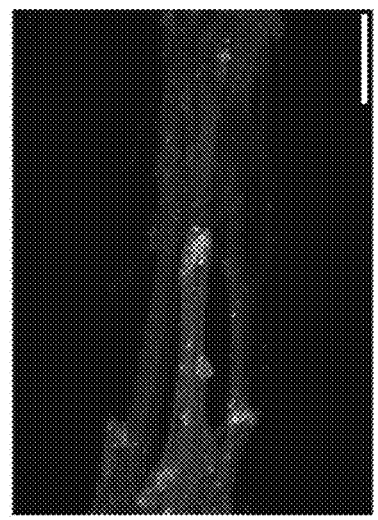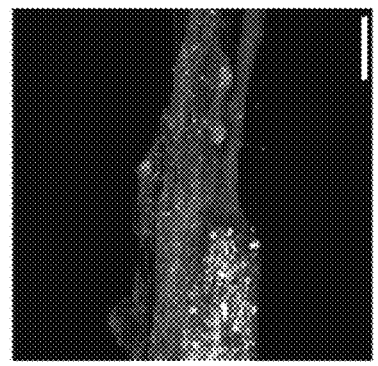
FIG. 31A  FIG. 31B  FIG. 31C  FIG. 31D  FIG. 31F

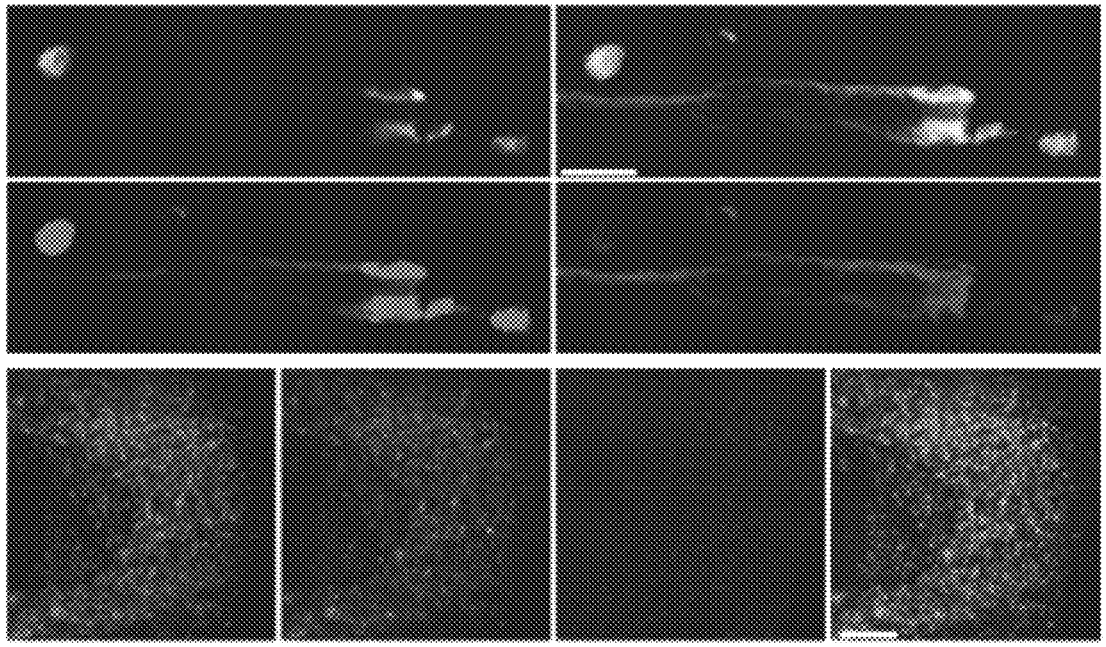
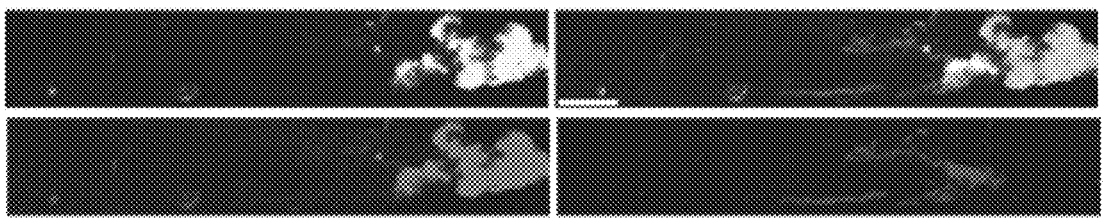
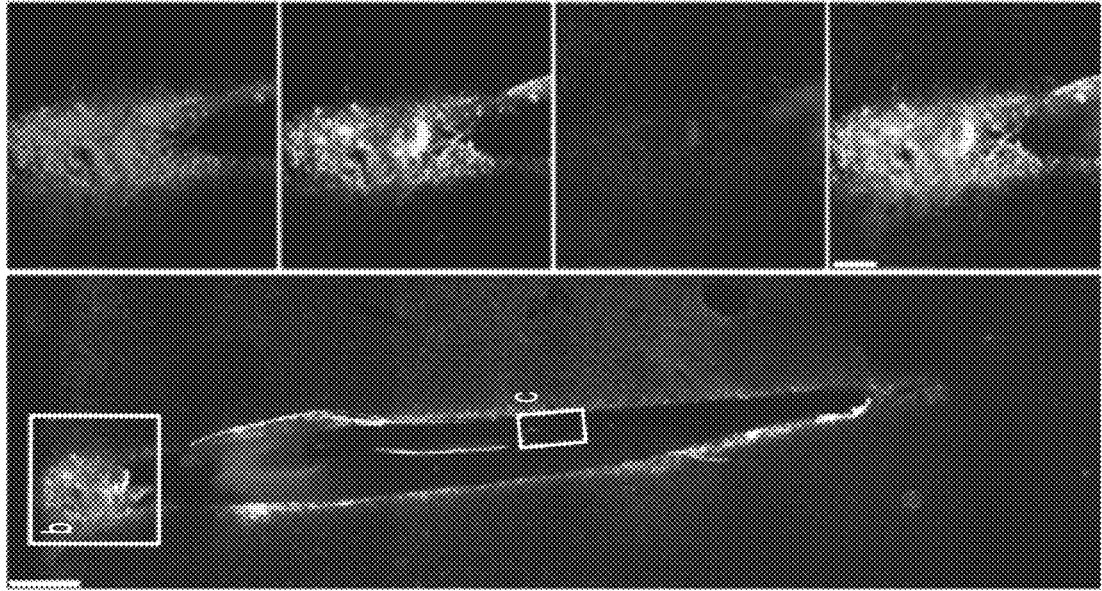
FIG. 34A  FIG. 34B  FIG. 34C  FIG. 34D  FIG. 34E

IMPLANTABLE LIVING ELECTRODES AND METHODS FOR USE THEREOF

CROSS-REFERENCE TO RELATED APPLICATION

This application is a continuation of U.S. patent application Ser. No. 16/093,036, filed Oct. 11, 2018, which is a national phase application under 35 U.S.C. 371 of International Application No. PCT/US2017/027705, filed Apr. 14, 2017, which claims priority to U.S. Provisional Application Ser. No. 62/322,434, filed Apr. 14, 2016, the contents of which is incorporated by reference herein in their entirety.

STATEMENT REGARDING FEDERALLY SPONSORED RESEARCH OR DEVELOPMENT

This invention was made with government support under grant number U01 NS094340 awarded by the National Institutes of Health. The government has certain rights in the invention.

BACKGROUND OF THE INVENTION

Brain Machine Interfaces (BMIs) allow the nervous system to directly communicate with external devices in order to mitigate deficits associated with neurodegeneration or to drive peripheral prosthetics. There has been substantial progress using penetrating microelectrode arrays and optogenetics strategies; however, these approaches are limited in that they generally rely on placing non-organic electrodes/optrodes into the brain, inevitably leading to an inflammatory foreign body response that ultimately diminishes the quality of the recording and stimulation. Current BMI strategies suffer from impermanence, non-specificity, and/or a significant foreign body response upon implantation.

BRIEF SUMMARY OF THE INVENTION

In one aspect, the invention comprises an implantable living electrode comprising a substantially cylindrical extracellular matrix core; one or more neurons implanted along or within the substantially cylindrical extracellular matrix core, the one or more neurons including one or more optogenetic or magnetogenetic neurons proximal to a first end of the implantable living electrode.

In various embodiments the implantable living electrode is capable of bidirectional stimulation and bidirectional recording.

In various embodiments the implantable living electrode is capable of unidirectional stimulation and unidirectional recording.

In various embodiments the implantable living electrode is capable of unidirectional stimulation and bidirectional recording.

In various embodiments the neurons are stimulated and recorded using different wavelengths of light.

In various embodiments the substantially cylindrical extracellular matrix core has a largest cross-sectional dimension selected from the group consisting of: between about 10 µm and about 20 µm, between about 25 µm and about 50 µm, between about 50 µm and about 100 µm, between about 100 µm and about 150 µm, between about 150 µm and about 200 µm, between about 200 µm and about 250 µm, between about 250 µm and about 300 µm, between about 300 µm and about 400 µm, between about 400 µm and about 500 µm, and between about 500 µm and about 700 µm, and between about 700 µm and about 1000 µm.

In various embodiments the implantable living electrode further comprises a hydrogel sheath coaxially surrounding the substantially cylindrical extracellular matrix core.

In various embodiments the hydrogel sheath has a largest cross-sectional dimension selected from the group consisting of: between about 20 µm and about 50 µm, between about 50 µm and about 100 µm, between about 100 µm and about 200 µm, between about 200 µm and about 250 µm, between about 250 µm and about 300 µm, between about 300 µm and about 350 µm, between about 350 µm and about 400 µm, between about 400 µm and about 450 µm, between about 450 µm and about 500 µm, between about 500 µm and about 600 µm, between about 600 µm and about 800 µm, and between about 800 µm and about 1200 µm.

In various embodiments the implantable living electrode has a length of about 100 µm to 10 cm or greater.

In various embodiments the one or more neurons include a plurality different phenotypes that target a plurality of targets and a plurality of different optogenetic or magnetogenetic phenotypes for responding to or emitting distinct wavelengths of light.

In various embodiments the one or more neurons include one or more selected from the group consisting of: primary cerebral cortical neurons, dorsal root ganglion neurons, glutamatergic neurons, GABAergic neurons, cholinergic neurons, dopaminergic neurons, serotonergic neurons, peptidergic neurons, neurons from the thalamus, neurons from the striatum, neurons from the hippocampus, neurons from the substantia nigra, neurons from the peripheral nervous system, and spinal motor neurons.

In various embodiments the primary cerebral cortical neurons include one or more selected from the group consisting of: neurons from layer I of the cortex, neurons from layer II of the cortex, neurons from layer III of the cortex, neurons from layer IV of the cortex, neurons from layer V of the cortex, neurons from layer VI of the cortex, neurons from the visual cortex, neurons from the motor cortex, neurons from the sensory cortex, and neurons from the entorhinal cortex.

In various embodiments the implantable living electrode further comprises one or more non-neuronal cells selected from the group consisting of: endothelial cells, myocytes, myoblasts, astrocytes, olfactory ensheathing cells, oligodendrocytes, or Schwann cells.

In various embodiments the neurons are derived from stem cells.

In various embodiments the neurons are derived from neuronal progenitor cells.

In various embodiments the hydrogel sheath comprises agarose.

In various embodiments the one or more neurons implanted along or within the substantially cylindrical extracellular matrix core are formed via forced cell aggregation.

In various embodiments the invention comprises a method comprising implanting one or more implantable living electrodes in a subject's brain; and placing a compatible stimulator in proximity to at least one of the one or more implantable living electrodes.

In various embodiments method further comprises controlling the compatible stimulator to actuate at least one of the implantable living electrodes to activate or excite brain activity.

In various embodiments the method further comprises controlling the compatible stimulator to actuate at least one of the implantable living electrodes to activate or excite host synaptic activity.

In various embodiments the method further comprises controlling the compatible stimulator to actuate at least one of the implantable living electrodes to activate or excite neuronal activity.

In various embodiments the method further comprises controlling the compatible stimulator to actuate at least one of the implantable living electrodes to activate or excite neural network activity.

In various embodiments the method further comprises controlling the compatible stimulator to actuate at least one of the implantable living electrodes to inhibit brain activity.

In various embodiments the method further comprises controlling the compatible stimulator to actuate at least one of the implantable living electrodes to inhibit host synaptic activity.

In various embodiments the method further comprises controlling the compatible stimulator to actuate at least one of the implantable living electrodes to inhibit neuronal activity.

In various embodiments the method further comprises controlling the compatible stimulator to actuate at least one of the implantable living electrodes to inhibit neural network activity.

In various embodiments the method further comprises controlling the compatible stimulator to actuate at least one of the implantable living electrodes to modulate host synaptic activity.

In various embodiments the method further comprises controlling the compatible stimulator to actuate at least one of the implantable living electrodes to modulate neuronal activity.

In various embodiments the method further comprises controlling the compatible stimulator to actuate at least one of the implantable living electrodes to modulate neural network activity.

In various embodiments at least one of the one or more implantable living electrodes are implanted in the subject's central nervous system, peripheral nervous system, cerebral cortex, striatum, hippocampus, spinal cord, and/or peripheral nerves.

In various embodiments the method further comprises selectively exciting or inhibiting cerebral cortical neurons.

In various embodiments the method further comprises selectively exciting or inhibiting dopaminergic neurons.

In various embodiments the method further comprises selectively exciting or inhibiting dorsal root ganglion neurons.

In various embodiments the invention comprises a method comprising implanting one or more implantable living electrodes in a subject's brain; and placing a compatible sensor in proximity to at least one of the one or more implantable living electrodes.

In various embodiments the method further comprises reporting activity of excitatory neurons.

In various embodiments the method further comprises reporting activity of inhibitory neurons.

In various embodiments the method further comprises simultaneously reporting activity of excitatory and inhibitory neurons.

In various embodiments the invention comprises a method comprising implanting one or more implantable living electrodes of in a subject's brain; and applying stimulus to the implantable living electrode to selectively excite or inhibit one or more selected from the group consisting of: glutamatergic neurons, GABAergic neurons, cholinergic neurons, serotonergic neurons, peptidergic neurons, neurons from the thalamus, neurons from the striatum, neurons from the hippocampus, neurons from the substantia nigra, neurons from the peripheral nervous system, spinal motor neurons, cerebral cortical neurons, dopaminergic neurons, and dorsal root ganglion neurons.

In various embodiments the method further comprises controlling the quantity of synaptic inputs.

In another aspect the invention comprises an implantable living electrode comprising a substantially cylindrical extracellular matrix core; a hydrogel sheath coaxially surrounding the substantially cylindrical extracellular matrix core; one or more selected from the group consisting of: electrodes, optrodes, magnetic actuators, heating probes, cooling probes, or chemical applicators positioned between the substantially cylindrical extracellular matrix core and the hydrogel sheath; and one or more neurons implanted along or within the substantially cylindrical extracellular matrix core.

In another aspect the invention comprises an implantable living electrode comprising: a substantially cylindrical extracellular matrix core; and a plurality of aggregated neurons implanted along or within the substantially cylindrical extracellular matrix core.

In various embodiments the plurality of aggregated neurons comprise dopaminergic neurons.

In various embodiments the extracellular matrix core comprises collagen-laminin.

In various embodiments the aggregated neurons are formed by centrifugation in pyramidal wells.

In various embodiments the implantable living electrode comprises a distinct neuronal body section and a distinct axonal section.

In various embodiments the implantable living electrode is a unidirectional or bidirectional implantable living electrode.

In various embodiments the extracellular matrix core comprises collagen-laminin.

In various embodiments the invention comprises a method of treating Parkinson's disease in a patient, comprising implanting a living electrode according to any one of claims into the substantia nigra of the patient.

In another aspect, the invention comprises a method of manufacturing an implantable living electrode comprising providing an extracellular matrix core; and contacting at least one end of the extracellular matrix core with a plurality of aggregated neurons.

In various embodiments the method further comprises maintaining the implantable living electrode under conditions that promote axon growth within or along the extracellular matrix core.

In various embodiments the method further comprises preforming the plurality of aggregated neurons prior to contacting the at least one extracellular matrix core.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIG. 4A illustrates a unidirectional micro-TENN: a single neuron (MAP-2+) population spanned by tau+ axonal tracts. FIG. 4B illustrates a bidirectional micro-TENN showing two neuron populations spanned by beta-tubulin-III+(Tuj-1+) axon tracts. FIG. 4C illustrates optical stimulation and recording (via genetically encoded opsins and/or fluorescent $Ca^{2+}$ reporters) and traditional electrophysiology paradigms in vitro. Micro-TENN activity was assessed by stimulating one population of neurons and recording the resulting action potentials in the other population electrophysiologically as well as optically based on $Ca^{2+}$-sensitive reporters.

FIGS. 5A-5E demonstrate micro-TENN structure, phenotype, and maturation for multiple architectures varying based on neuronal somatic distribution and axonal penetration. FIG. 5A shows a confocal reconstruction of a unidirectional dopaminergic micro-TENN at 2 weeks in vitro (green: all axons (beta-tubulin-III+); red: dopaminergic neurons (tyrosine hydroxylase+); blue: all nuclei). FIG. 5B depicts a phase contrast micrograph of a bidirectional cerebral cortical neuron micro-TENN. FIGS. 5C and 5D depict dorsal root ganglia neuron unidirectional micro-TENNs. FIG. 5E depicts a dense unidirectional cortical neuron micro-TENN with the somatic region externalized relative to the hydrogel micro-column. Control of structure, phenotype, maturation/plasticity, and function of micro-TENN living electrodes has been demonstrated in vitro.

FIG. 7A illustrates the finding that at 3 days after delivery into the rat brain, micro-TENN neurons survived and maintained their axonal architecture within the hydrogel tube. FIG. 7B-FIG. 7D illustrate the finding that at 28 days post-implant, micro-TENN neurons survived and integrated with the brain. FIG. 7B illustrates transplanted neurons extended neurites into host tissue. FIG. 7C-7D illustrate a magnification of a region from FIG. 7B showing putative dendritic spines along ingrowing neurites with (FIG. 7D) synapsin-positive puncta in immediate proximity (circles) to neurites, suggesting synaptic integration. Scale bars are as follows: FIG. 7A=50 µm, FIG. 7B=40 µm, FIG. 7C and FIG. 7D=20 µm.

FIG. 14A-FIG. 14C provide confocal slices along planes illustrated in FIG. 14D. FIG. 14A is a bottom-most confocal slice showing cell nuclei resting at bottom of macro-TENN construct. FIG. 14B is a confocal slice just above the slice shown in FIG. 14A, showing axons (green) growing along the inner edge of the macro-TENN construct. FIG. 14C is a confocal slice just above the slice shown in FIG. 14B, showing axons (green) growing only at the edges of the interface only at the north or south side of the tube. FIG. 14D is a schematic looking down length of macro-TENN to diagrammatically describe confocal slices shown in FIG. 14A-FIG. 14C. FIG. 14E depicts a reconstruction of confocal images in FIG. 14A-FIG. 14C as shown in cross section, similar to the viewpoint of FIG. 14D.

FIG. 15A provides a view looking down a nerve. FIG. 15B provides a view looking along a length of a nerve. FIG. 15C depicts a tapered device where ends match nerve size, but interior of construct is larger to increase surface area and fascicular separation. (Electrodes are not shown in FIG. 15C for clarity).

FIG. 16A-FIG. 16E provide phase contrast micrographs of micro-TENNs built using (FIG. 16-FIG. 16B) neuronal suspension delivery versus (FIG. 16C-FIG. 16E) forced neuronal aggregate delivery. FIG. 16A-FIG. 16B show an example of a micro-TENN with neuronal somata infiltration throughout the micro-column interior, a consequence of imperfect extracellular-matrix (ECM) continuity in the core. In cases where this occurs, this results in a deviation from the ideal micro-TENN cytoarchitecture. In FIG. 16C-FIG. 16E, in contrast, when precisely formed neuronal aggregates are used to seed the micro-columns, the idealized distribution of somatic (FIG. 16D) and axonal (FIG. 16E) zones is consistently maintained.

FIG. 17A-FIG. 17D show phase contrast and confocal micrographs of neuronal somatic and axonal distribution in forced neuronal aggregate micro-TENNs. As seen in FIG. 17A-FIG. 17B, neuronal aggregates can be precisely seeded at an end of the micro-column. In FIG. 17C, over several days in vitro, dense axonal outgrowth can be observed projecting from the neurons in the aggregate. FIG. 17D provides a confocal micrograph following immunocytochemistry to label these aggregate micro-TENNs using antibodies recognizing all axons (beta-tubulin III; red) and all cell nuclei (Hoechst; blue), and synapses (synapsin; green). The hydrogel comprising the micro-column is non-specifically labeled as purple. This demonstrates defined, distinct somatic (Hoechst+) and axonal (beta-tubulin III+) regions, whereas the synapsin+ puncta demonstrates functional maturation and electrochemical activity in the micro-TENNs. The neuronal aggregate seeding methodology consistently resulted in the formation of uni- or bi-directional micro-TENNs of the idealized cytoarchitecture consisting of a defined zone with neuronal somata as aggregates at one or both ends of the micro-column and a defined zone with axonal projections running longitudinally to span the central portion of the micro-column.

FIG. 19A-FIG. 19B depict long-projecting unidirectional axonal-based living electrodes for neuromodulation: FIG. 19A depicts confocal reconstruction of a cerebral cortical neuron living electrode at 28 DIV, immunolabeled for axons (β-tubulin-III; red) and neuronal somata/dendrites (MAP-2; green), with nuclear counterstain (Hoechst; blue). Insets of the aggregate (FIG. 19a') and axonal (FIG. 19a") regions are outlined and shown to the right. Scale bars: 100 Panel B depicts confocal reconstruction of a ventral mesencephalic (dopaminergic) living electrode at 28 DIV, immunolabeled for axons (β-tubulin-III; green) and tyrosine hydroxylase (dopaminergic neurons/axons; red), with nuclear counterstain (Hoechst; blue). Insets of the aggregate (FIG. 19b') and axonal (FIG. 19b") regions are outlined and shown to the left. Scale bars: 250 μm.

In FIG. 20A, axons projecting from dopaminergic living electrodes will form synapses within local striatal architecture, and, due to in vitro functionalization with channelorhodopsins, may release dopamine upon optical stimulation of the perikaryal segment at the brain surface. This mimics the substantia nigra pars compacta input to the striatum in a manner that can be externally controlled. In FIG. 20B, axons from glutamatergic living electrodes may preferentially synapse on to layer IV neurons within primary sensory cortex to convey illusory haptic feedback via surface optical stimulation to achieve closed-loop control of neuromotor prosthetics in patients with paralysis. In FIG. 20C, axons from GABAergic living electrodes could be implanted to appose seizure foci such that optical stimulation would cause net suppression of seizure activity in patients with lesional epilepsy.

FIG. 21A shows that, in the simplest form, "channel select" bundles of axons can transmit signals to select which other bundles transmit signals into the brain, and which are silenced. In FIG. 21B, multiple channels that converge on to one final common output can likewise be toggled by the "channel select" in a biological instantiation that most resembles the kind of multiplexing used in telecommunications. In FIG. 21C likewise, a single input channel can be selected or diverted to one or more parallel outputs to "demultiplex" that signal.

FIG. 23A1-FIG. 23G depict improved micro-TENN cytoarchitecture using forced aggregation method as applied in compositions and methods that employ these embodiments. Phase contrast and confocal reconstructions of micro-TENNs plated with primary dopaminergic neurons at 14 DIV. FIG. 23A1-FIG. 23A3 depict representative micro-TENN plated with dissociated neurons labeled via immunocytochemistry to denote neurons/axons (β-tubulin III) and cell nuclei (Hoechst). Dissociated micro-TENNs did not demonstrate the desired cytoarchitecture as they showed cell infiltration throughout the entire length of the inner core. FIG. 23B-FIG. 23C present phase contrast images depicting micro-TENNs plated with engineered dopaminergic neuron aggregates. Based upon plating technique, aggregates either (FIG. 23B) attached directly outside the agarose microcolumn, or (FIG. 23C) inside the inner core. Higher magnification images from demonstrative regions in (FIG. 23B, FIG. 23C) show that while the (FIG. 23D1, FIG. 23D3) cell body regions differed between the two aggregate plating techniques, their (FIG. 23D2, FIG. 23D4) axonal regions were similar. FIG. 23E1-FIG. 23E4 present representative aggregate micro-TENN labeled via immunocytochemistry to denote all neurons/axons (β-tubulin III) and dopaminergic neurons/axons (TH), with cell nuclei counterstain (Hoechst). Aggregate micro-TENNs demonstrated the ideal cytoarchitecture, with (FIG. 23E1) discrete cell body regions and (FIG. 23E2, FIG. 23E3) axonal regions. FIG. 23F1-FIG. 23F4 presents a higher magnification reconstruction from a demonstrative region in (FIG. 23E1_FIG. 23E4) that depicts the aggregated cell bodies. FIG. 23G demonstrates that micro-TENNs generated using aggregates demonstrated a greater extent of axonal outgrowth than micro-TENNs plated with dissociated neurons (n=13 micro-TENNs each group; Mann-Whitney test, p<0.0001). Data are presented as mean±standard deviation. Scale bar (FIG. 23A3)=250 μm. Scale bar (FIG. 23B, FIG. 23C)=500 μm. Scale bar (FIG. 23D1)=200 μm. Scale bar (FIG. 32D2-FIG. 23D4)=100 μm. Scale bar (FIG. 23E4)=250 μm. Scale bar (FIG. 23F4)=50 μm.

FIG. 24A1-FIG. 24F depict the effect of extracellular matrix on axonal outgrowth within micro-TENNs. Representative confocal reconstructions of dopaminergic micro-TENNs plated with different ECM cores. At 14 DIV, all micro-TENNs were labeled via immunocytochemistry to denote all neurons/axons (β-tubulin III) and dopaminergic neurons/axons (TH), with nuclear counterstain (Hoechst). The type of ECM strongly influenced axonal outgrowth, with (FIG. 24A1-FIG. 24A3) collagen I (n=12 micro-TENNs) and a (FIG. 24C1-FIG. 24C3) collagen I and laminin cocktail (n=12) supporting the longest axonal outgrowth. Micro-TENNs with (FIG. 24B1-FIG. 24B3) empty cores (n=9) or (FIG. 24D1-FIG. 24D3) crosslinked collagen cores (n=11) demonstrated significantly less outgrowth. (FIG. 24a1-24d4) Higher magnification reconstructions from demonstrative regions in (FIG. 24A1-FIG. 24D3) show similar expression of TH across groups. FIG. 24E is a graph showing that a one way ANOVA (p<0.0001) followed by a post-hoc Tukey's test determined that collagen I and collagen I-laminin cocktail cores were statistically equal (p=0.8590), and that they each supported axonal outgrowth that was statistically longer then outgrowth in empty (p<0.0001), laminin-coated (p<0.0001), or crosslinked collagen (p<0.0001) cores (* denotes significance). FIG. 24F is a graph showing that, as determined by a Mann-Whitney test, the lengths of TH+ axons as a percentage of total axonal length were statistically equivalent between the collagen I (n=12) and collagen I and laminin (n=12) inner cores (p=0.9723). Data are presented as mean±standard deviation. Scale bar (FIG. 24A3, FIG. 24BC3, FIG. 24D3)=500 μm. Scale Bar (FIG. 24B3)=250 μm. Scale bar (FIG. 24a4, FIG. 23b4, FIG. 24c4, FIG. 24d4)=50 μm.

FIG. 25A-FIG. 25G depict long-projecting dopaminergic micro-TENNs. FIG. 25A-FIG. 25F are confocal reconstructions of a representative micro-TENN plated with a dopaminergic aggregate and collagen I inner core at 28 DIV. Micro-TENN labeled via immunocytochemistry to denote all neurons/axons (β-tubulin III) and dopaminergic neurons/axons (TH), with nuclear counterstain (Hoechst). In FIG. 25A-FIG. 25D, long-term dopaminergic micro-TENNs showed robust survival and axonal extension over 28 DIV. FIG. 25E-FIG. 25F are higher magnification reconstructions from demonstrative regions in FIG. 25C and show healthy TH+ neurons and axons, with apparent axonal varicosities suggesting sites of dopamine release. FIG. 25G shows micro-TENN length measurements taken at 28 DIV (n=7 micro-TENNs) demonstrated TH+ axons measuring 6046±670 μm, and a total TH+ length of 7264±672 μm with the inclusion of the dopaminergic aggregate. Importantly, these lengths are more than sufficient to span the nigrostriatal pathway in rats. Data are presented as mean±standard deviation. Scale bar (FIG. 25A-FIG. 25D)=250 μm. Scale bar (FIG. 25E-FIG. 25F)=50 μm.

FIG. 26A-FIG. 26H depict synapse formation between micro-TENN dopaminergic axons and striatal neurons in vitro. FIG. 26A depicts representative confocal reconstruction at 14 DIV of a dopaminergic micro-TENN plated with an aggregated striatal end target. The micro-TENN was labeled via immunocytochemistry to denote dopaminergic neurons/axons (TH), striatal (medium spiny) neurons (DARPP-32), and synapses (synapsin), with nuclear counterstain (Hoechst). FIG. 26B-FIG. 26E show higher magnification reconstructions from demonstrative regions in (FIG. 26A) depict the (FIG. 26B) dopaminergic neuron aggregate, (FIG. 26C) robust, aligned TH+ axons, and (FIG. 26D) neurite outgrowth from the striatal neuron population. (FIG. 26E) A high degree of synapsin labeling along the trajectory of TH+ axons suggests that dopaminergic axons formed synapses with the striatal neurons. FIG. 26F is a graph showing that micro-TENNs containing striatal end targets did not result in statistically longer axonal outgrowth when compared to unidirectional dopaminergic micro-TENNs with no end target (n=9) micro-TENNs each group; Mann-Whitney test, p=0.9182). Data are presented as mean±standard deviation. In FIG. 26G-FIG. 26H synapsin+ puncta can be seen decorating putative dendrites projecting from striatal neurons shown with dopaminergic axonal varicosities, further suggesting synaptic integration. Scale bar (FIG. 26A)=250 μm. Scale bar (FIG. 26B-FIG. 26E)=50 μm. Scale bar (FIG. 26G-FIG. 26H)=20 μm.

FIG. 27A-FIG. 27D depict micro-TENN neuronal survival and maintenance of axonal cytoarchitecture in vivo. FIG. 27A depicts micro-TENN implant trajectory and dimensions drawn to scale (adapted from Gardoni F, Bellone C. 2015, Modulation of the glutamatergic transmission by Dopamine: a focus on Parkinson, Huntington and Addiction diseases, Frontiers in cellular neuroscience, 9: 25.). FIG. 27B depicts micro-TENN orientation (not to scale). FIG. 27C depicts a representative sagittal section at 1 week post-implant, showing a longitudinal view of a dopaminergic micro-TENN with all neurons expressing GFP on the synapsin promoter and labeled via immunohistochemistry to denote dopaminergic neurons/axons (TH). This demonstrates that micro-TENN neurons survived and the longitudinally aligned cytoarchitecture was maintained. FIG. 27D depicts, at 1 month post-implant, a representative oblique section providing a cross-sectional view of a GFP+ dopaminergic micro-TENN labeled via immunohistochemistry to denote dopaminergic neurons/axons (TH) and all neurons/axons (β-tubulin III). This demonstrates healthy transplanted neurons/axons with robust dopaminergic axonal projections at 1 month in vivo. Scale bar (FIG. 27C)=20 μm. Scale bar (FIG. 27D)=50 μm.

FIG. 28A is a conceptual schematic of micro-TENNs. FIG. 28A depicts a micro-TENN three-dimensional construct up to several millimeters in length consisting of hydrogel cylinder encasing an extracellular matrix core of collagen and laminin. Current micro-TENNs have a 300-400 micron outer diameter with a 180 micron inner diameter, but may be made at any size. Neuronal populations are placed at one or both ends of the cylinder, with axonal tracts penetrating the ECM and spanning the cylinder length. FIG. 28B depicts that neurons from unidirectional micro-TENN neurons may synapse with host neurons, allowing for the transmission of signal inputs to targeted cortical regions. FIG. 28C further depicts that host neurons may synapse and integrate with bidirectional micro-TENNs, allowing for the transmission of signal outputs from targeted cortical regions to the dorsal neuronal population. FIG. 28B further depicts the delivery and integration of micro-TENNs in vivo as "living electrodes". Micro-TENNs are preformed in vitro; upon implantation in the brain, these living microconduits may serve as input/output channels for sensorimotor information. Further referring to FIG. 28B, for inputs, an LED array (1) optically stimulates a unidirectional micro-TENN with channelrhodopsin-positive neurons (2), which synapse with host Layer IV neurons (3). For outputs, host neurons from Layer V (4) synapse with the neurons of a bidirectional micro-TENN (5); neuronal activity is recorded by a microelectrode array (6).

FIG. 29A-FIG. 29H depict aggregate fabrication of micro-TENNs, comparing Traditional vs. Aggregate Cortical Micro-TENNs. Living electrodes are fabricated in two steps: formation of the agarose microcolumn, and cortical neuronal aggregation. FIG. 29A depicts agarose microcolumn formation. 1: A custom-designed, reusable acrylic mold is used to generate agarose microcolumns with a specified inner and outer diameter. 2: Top view of the assembled mold. Dashed lines indicate the outer (middle) and inner diameters (top; bottom). 3: Needles of the specified inner diameter are inserted into the mold. 4: Molten agarose is introduced into the mold and allowed to cool. 5: The needles are removed, the mold disassembled and the microcolumns removed. FIG. 29B depicts cortical neuronal aggregation. 1: Square pyramidal wells are cast in PDMS from a 3D-printed positive mold. 2: Image of the PDMS pyramidal wells. 3: Single-cell suspensions of rodent embryonic neurons are introduced into the wells and centrifuged into neuronal aggregates. 4: Phase image of an aggregate 24 hours after plating. 5: Confocal reconstruction of aggregate at 72 hours, stained for live and dead neurons. FIG. 29C depicts agarose microcolumns being filled with an extracellular matrix (1 mg/ml laminin and collagen; pH 7.2-7.4). Neuronal aggregates are then placed at one or both ends of the microcolumn, and allowed to grow in vitro. All scale bars: 100 (FIG. 29D-FIG. 29E) Micro-TENNs in prior work were fabricated with dissociated neurons. Dissociated micro-TENNs exhibited axonal growth and network formation over several days in vitro, but control and reproducibility of micro-TENN architecture was inherently limited. (FIG. 29F, FIG. 29G, FIG. 29H) With the aggregate method, one or two neuronal aggregates (for unidirectional or bidirectional micro-TENNs, respectively) are used to seed the microcolumns. Shown is a representative bidirectional micro-TENN after 3 days in vitro. Aggregate micro-TENNs exhibit robust axonal growth and more controllable architecture. Specifically, aggregation results in reliably discrete regions populated either by cell bodies (FIG. 29G) or neuritic projections (FIG. 29H).

(FIG. 30C) Longer bidirectional micro-TENNs (5 mm) took longer to develop, but still showed robust growth. Representative micro-TENN shown at 1, 3, and 5 DIV. (FIG. 30D) Quantified growth rates for 2 mm unidirectional, 2 mm bidirectional, 5 mm bidirectional, and 2 mm dissociated/traditional micro-TENNs at 1, 3, 5, 8, and 10 DIV. Growth rates were quantified by identifying the longest neurite from an aggregate in phase microscopy images (10× magnification) at the listed timepoints. Sample sizes: n=6 (Unidirectional—2 mm), 9 (Bidirectional—2 mm), 7 (Bidirectional—5 mm), and 7 (Dissociated—2 mm). Error bars denote s.e.m. Scale bars: 100 μm.

FIG. 31A-FIG. 31F depict aggregate-specific growth with fluorescent labeling. Confocal reconstructions of bidirectional micro-TENNs labeled with GFP and mCherry to observe axonal growth from each aggregate in vitro. (FIG. 31A, FIG. 31B, FIG. 31C) A micro-TENN at 1 (FIG. 31A), 3 (FIG. 31B), and 7 (FIG. 31C) DIV. By 3 DIV there is putative axon-axon contact from each aggregate, followed by more robust outgrowth by 5 DIV. (FIG. 31D) Another micro-TENN at 6 DIV, with insets showing axons from each aggregate growing along each other (FIG. 31E) and axons from one aggregate making contact with the opposite population (FIG. 31F). Scale bars: 500 μm (FIG. 31A, FIG. 31D); 100 μm (FIG. 31E, FIG. 31F).

(FIG. 32A, FIG. 32B, FIG. 32C) Representative confocal live-dead images showing live cells, dead cells, and an overlay of a unidirectional micro-TENN at 10 DIV, with outlined insets below. (FIG. 32D, FIG. 32E, FIG. 32F) Representative confocal live-dead image of a bidirectional micro-TENN at 28 DIV, with outlined insets below.

All scale bars: 100 µm. (FIG. 32G) Graph denotes the average proportion of live cell body area to total (live+dead) cell area for each experimental group and timepoint. Two-way ANOVA and post-hoc analysis revealed several statistically relevant pairwise differences (*=p<0.05; =p<0.01; *=p<0.001). Error bars denote s.e.m. Sample sizes: n=4 and 4 (unidirectional); 7 and 4 (bidirectional); 9 and 5 (controls) for 10 and 28 DIV, respectively. (FIG. 32H) A live-dead confocal image of a micro-TENN stained at 40 DIV. Scale bar: 100 µm.

(FIG. 33F) Confocal reconstruction of a representative unidirectional micro-TENN at 28 DIV. Scale bars: 200 µm.

FIG. 34A-FIG. 34E depict corticothalamic micro-TENN implantation. Cross-sections of brain one month following GFP-positive micro-TENN implantation. Implantation here mimics the "living electrode" application (FIG. 28A-FIG. 28B), with a large dorsal population of neurons extending axons ventrally into the brain. Brains were sectioned and stained to identify micro-TENN neurons (GFP), dendrites and somata (MAP-2), and axons (Tuj-1). FIG. 34A Dorsal view of micro-TENN, with insets referring to callout boxes showing the aggregate (b) and lumen of the micro-TENN, containing axons (c). Similarly, cross-sections of another micro-TENN implantation reveal the aggregate (FIG. 34D) and axons within the lumen FIG. 34E of the micro-column. Scale bars: 200 µm FIG. 34A; 100 µm (FIG. 34B); 50 µm (FIG. 34D); 25 µm (FIG. 34C, FIG. 34E).

DEFINITIONS

Figure 1:
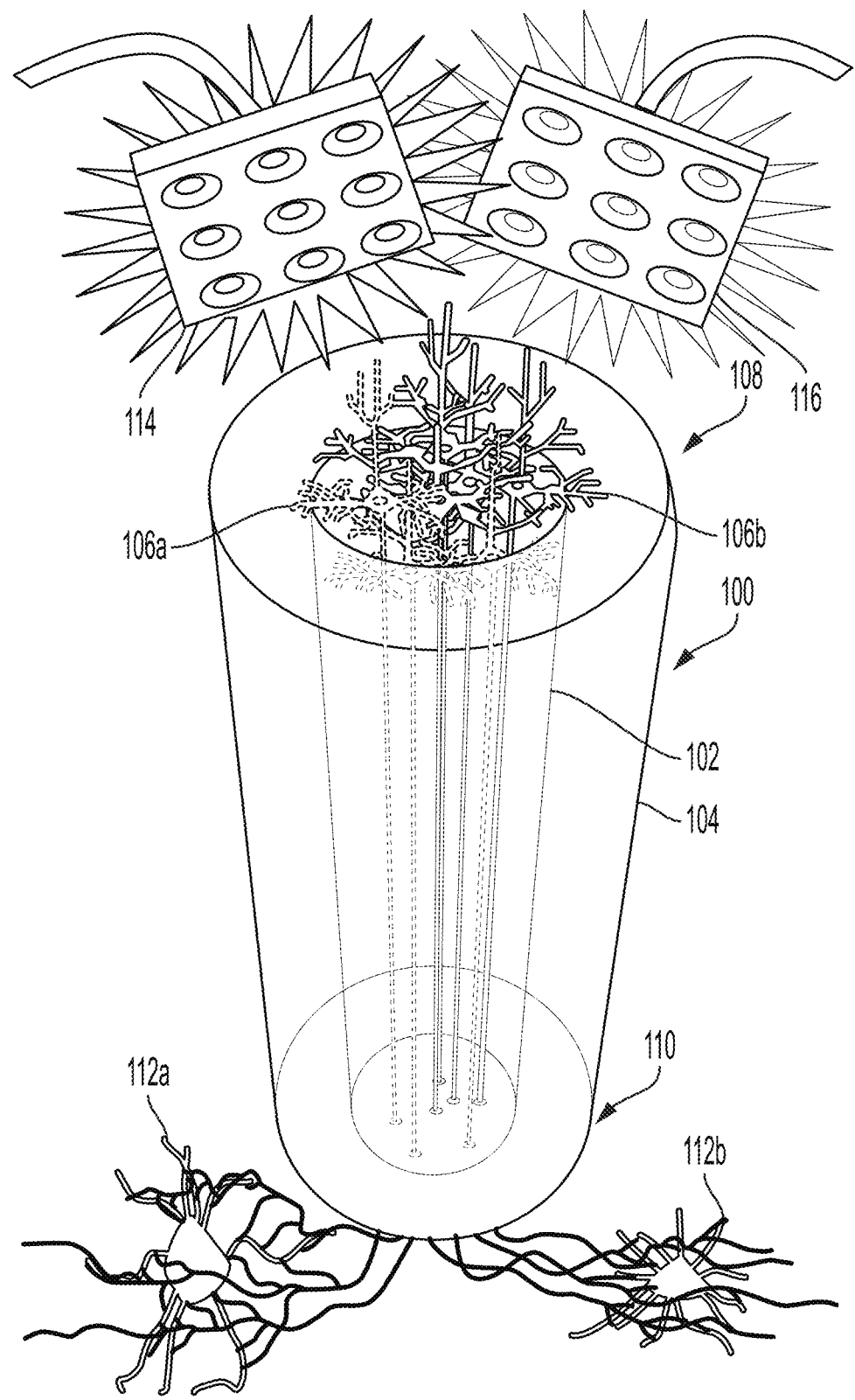
FIG. 1 is a picture illustrating an implantable living electrode (designated by arrow number 100), comprising a cylindrical extracellular matrix core (102) coaxially surrounded by a hydrogel sheath (104) and implanted with neurons (106a, 106b) according to an embodiment of the invention. In one embodiment, certain populations of neural cells (112a) can be excited by one wavelength of light (114), while application of another wavelength of light (116) inhibits another population of neural cells (112b). In another embodiment, two different populations of neural cells can be excited by two different wavelengths of light. In yet another embodiment, two different populations of neural cells can be inhibited by different wavelengths of light.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

As used herein, the term "cylinder" or "cylindrical" includes a surface consisting of each of the straight lines that are parallel to a given straight line and pass through a given curve. In some embodiments, cylinders have an annular profile. In other embodiments, the cylinder has a cross-section selected from the group consisting of: a square, a rectangle, a triangle, an oval, a polygon, a parallelogram, a rhombus, an annulus, a crescent, a semicircle, an ellipse, a super ellipse, a deltoid, and the like. In other embodiments, the cylinder is the starting point of a more complex three-dimensional structure that can include, for example, complex involutions, spirals, branching patterns, multiple tubular conduits, and any number of geometries that can be implemented in computer-aided design, 3-D printing, and/or in directed evolutionary approaches of secretory organisms (e.g., coral), including of various fractal orders.

As used herein, the term "living scaffolds" refers to biological scaffolds comprised of living neural cells in a preformed, often anisotropic, three-dimensional (3-D) architecture. Living scaffolds can physically integrate with existing host tissue. Living scaffolds may facilitate targeted neural cell migration and axonal pathfinding by mimicking key developmental mechanisms. Living scaffolds can act based on the simultaneous presentation of structural and soluble cues, and/or electrophysiological, ionic, or neurotransmitter based signaling.

As used herein, the term "living electrode" refers to a living construct including neural cells, generally but not exclusively neurons, with a defined architecture generally comprised of discrete somatic region(s) with protruding neurite tracts (axonal or dendritic) designed to probe or modulate the nervous system.

Unless specifically stated or obvious from context, the term "or," as used herein, is understood to be inclusive.

As used herein, "synapse" refers to a junction between a neuron and another cell, across which chemical communication flows.

As used herein, "synapsed" refers to a neuron that has formed one or more synapses with one or more cells, such as another neuron or a muscle cell.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Aspects of the invention utilize advanced micro-tissue engineering techniques to create the first biological living electrodes for chronic BMI and/or neuromodulation. Novel micro-Tissue Engineered Neural Networks (micro-TENNs) serve as the living electrodes, which are composed of discrete population(s) of neurons connected by long axonal tracts, generally contained within miniature tubular hydrogels. These living micron-scale constructs are able to penetrate the brain to a prescribed depth for integration with local neurons/axons, with the latter portion remaining externalized on the brain surface where functional information is inputted/controlled and/or outputted/gathered using a next-generation optical and electrical interface.

Micro-TENN neurons survive, integrate with local host neurons, and maintain their axonal architecture. These features are exploited to advance living electrodes as a functional relay to and from deep regions of the brain. In this radical paradigm, only the biological component of these constructs penetrates the brain, thus attenuating a chronic foreign body response. Moreover, through custom cell and tissue engineering techniques, the specific host neuronal subtypes with which the micro-TENN neurons form synapses may be influenced, thereby adding a level of specificity in local stimulation and recoding not currently attainable with conventional microelectrodes.

Electrophysiological, optogenetic, and advanced microscopy techniques reveal evidence of micro-TENN synaptic integration with brain neural networks and cross-communication with micro-TENN neurons on the cortical surface in rats. This versatile platform technology will read out local brain activity and provide input to affect neural activity and function, thereby providing the first demonstration of tissue engineered living electrodes to functionally integrate into native neural networks and to serve as a conduit for bidirectional stimulation and recording. This potentially transformative technology at the interface of neuroscience and engineering lays the foundation for preformed implantable neural networks as a viable alternative to conventional electrodes.

Referring now to FIG. 1, one embodiment of the invention provides an implantable living electrode (100). The electrode can include a substantially cylindrical extracellular matrix core (102) and a hydrogel sheath (104) coaxially surrounding the substantially cylindrical extracellular matrix core (102). One or more neurons (106a, 106b) can be implanted along or within the substantially cylindrical extracellular matrix core (102). The one or more neurons (106a, 106b) can include one or more optogenetic or magnetogenetic neurons proximal to a first end (108) of the implantable living electrode.

The extracellular matrix core (102) can comprise proteins, nucleic acids, small molecules, hormones, growth factors, and the like that enhance axonal growth, promote survival, reduce host inflammation, or promote integration of the composition into host tissue. Exemplary proteins include collagen, laminin, fibrin, and fibronectin. The extracellular matrix core (102) can additionally or alternatively include hyaluronic acid. The extracellular matrix core can be unilayer (a single material cured around living axons), bilayer (as depicted herein), or tri-layer.

The hydrogel sheath (104) can provide mechanical support for the extracellular matrix core (102) sufficient to protect the extracellular matrix core (102) from bending, buckling, collapsing, and the like before, during, and/or after implantation. For example, the hydrogel sheath (104) can have sufficient mechanical rigidity to allow for loading within a needle and advancement from the needle within a subject's tissue. The hydrogel sheath (104) can, in some embodiments, be impermeable or substantially impermeable to axonal projections in order to guide and confine axonal growth within and/or substantially parallel to a central axis of the hydrogel sheath (104). In some embodiments, the hydrogel sheath (104) dissolves, degrades, and/or is absorbed after a period of time (e.g., one month).

In some embodiments, both the extracellular matrix core 102 and the hydrogel sheath (104) are fabricated from hydrogels, although the hydrogels can have different mechanical and/or chemical properties.

Additionally, the sheath (104) can be omitted and the core (102) can be fabricated from a hydrogel and/or an extracellular matrix embedded with cells and axons and having sufficient strength to resist bending, buckling, collapsing, and the like before, during, and/or after implantation.

The one or more neurons (106a, 106b) can be implanted in various locations within the implantable living electrode (100). In one embodiment, the neurons (106) are implanted at one end (e.g., first end 108 or second end 110) and grow to the other end of the electrode after implantation. In another embodiment, the neurons are implanted in the center of the implantable living electrode (100) and grow axially in both directions. In still other embodiments, the neurons are placed on an end surface of the electrode (100) and grow into and through the extracellular matrix core (102). In still other embodiments, the neurons (106) are mixed or placed throughout the extracellular matrix core (102) prior to implantation and form axonal projections that connect with adjacent neurons to facilitate communication across the electrode (100). In one embodiment, the neurons lie at an interface between the extracellular matrix core (102) and the hydrogel sheath (104). In other embodiments, glial cells, or other neural or non-neural phenotypes, are implanted to facilitate growth and phenotypic differentiation of neurons.

The neurons useful for the compositions and methods provided herein include all neuronal subtypes, including but not limited to PNS motor or sensory, CNS, and stem cells (e.g., induced pluripotent stem cells, embryonic stem cells, and the like) differentiated into a neuronal phenotype. In one embodiment of the present invention, neurons are derived from any cell that is a neuronal cell (e.g., cortical neurons, dorsal root ganglion neurons or sympathetic ganglion neurons) or is capable of differentiating into a neuronal cell (e.g., stem cell). The neurons may be autologous, allogenic, or xenogenic with reference to the subject.

In certain embodiments, the neurons are peripheral or spinal cord neurons including dorsal root ganglion neurons or motor neurons. In certain embodiments, the neurons are from brain, including but not limited to, neurons from the cerebral cortex, thalamus, hippocampus, striatum, substantia nigra and cerebellum. In certain embodiments, primary cerebral cortical neurons include but are not limited to neurons from layers I, II, III, IV, V, and/or VI of the cortex (separately or in any combination thereof), neurons from the visual cortex, neurons from the motor cortex, neurons from the sensory cortex, and neurons from the entorhinal cortex. The neurons may be excitatory or inhibitory neurons. The neurons may be glutamatergic, dopaminergic, GABAergic, serotonergic, cholinergic, or any other type of neuron as classified based upon its primary neurotransmitter.

Neurons useful in the invention may be derived from cell lines or other mammalian sources, such as donors or volunteers. In one embodiment, the neurons are human neurons. In one embodiment, the neurons are non-human mammalian neurons, including neurons obtained from a mouse, rat, dog, cat, pig, sheep, horse, or non-human primate. In one embodiment, the neurons are cortical neurons, hippocampal, neurons, dorsal root ganglion neurons or sympathetic ganglion neurons. In another embodiment, neurons are derived from immortalized cell lines that are induced to become neuron-like (e.g., NT2, PC12). In one embodiment, the neurons are neurons derived from a cadaver. In another embodiment, the neurons are neurons derived from patients who have undergone ganglionectomies, olfactory epithelium biopsy, temporal lobectomy, tumor margin resection, peripheral nerve biopsy, brain biopsy, ventricular shunt implantation with biopsy, or other clinical procedure. Furthermore, the neurons may be singular, integrated neurons or a plurality of integrated neurons (i.e., an integrated nerve bundle).

In certain embodiments, the glial cells (e.g., astrocytes that may extend processes to modulate host synaptic, axonal, dendritic, somatic, and/or host network activity) are incorporated in addition or as an alternative to neurons 106. These can be brain or spinal cord derived astrocytes. In certain embodiments, the cells are olfactory ensheathing cells, oligodendrocytes, Schwann cells, endothelial cells, or myocytes/myoblasts.

The number or density of the cells positioned at either end of the construct is dependent upon the type of neuron being used and the eventual use of the construct. For example, in certain embodiments, 1, 100, 1,000, 10,000, 1,000,000, 100,000,000, or more cells are positioned at an end of the construct.

In certain embodiments, the neurons are cultured in vitro or ex vivo. Culture of the neurons can be performed under suitable conditions to promote the growth of axons through the core of the construct. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. For example, the cells may require a nutritional supplement (e.g., nutrients and/or a carbon source such as glucose), exogenous hormones or growth factors, differentiation factors, and/or a particular pH. Exemplary cell culture media that can support the growth and survival of the neuron includes, but is not limited to, NEUROBASAL® media, NEUROBASAL® A media, Dulbecco's Modified Eagle Medium (DMEM), and Minimum Essential Medium (MEM). In certain embodiments, the culture medium is supplemented with B-27® supplements. In certain embodiments, the culture medium may contain fetal bovine serum or serum from another species at a concentration of at least 1% to about 30%, or about 5% to about 15%, or about 10%. In one embodiment, the culture medium comprises NEUROBASAL® supplemented with about 2% B-27 and about 500 µM L-glutamine.

As depicted in FIG. 1, a single electrode 100 can support multiplexing of a plurality of different types of neurons (106a, 106b). For example, the neurons (106a, 106b) can have different phenotypes that are designed to target distinct structures (112a, 112b) and/or facilitate communication along different channels. In one embodiment, the neurons respond to or emit different wavelengths of energy for optogenetic control and/or monitoring of nerves. For example, the electrode (100) can support bidirectional stimulation and recording, e.g., by applying a first wavelength of light from a light source (114) and detecting a second, different wavelength using a detector (116).

Dimensions

Figure 2A:
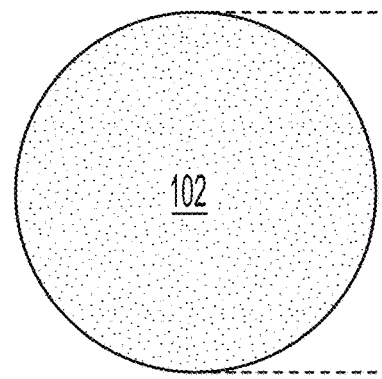
FIGS. 2A-2C depict cross-sections of electrodes comprising an extracellular matrix core (102) surrounded by a hydrogel sheath according to an embodiment of the invention.
Figure 2B:
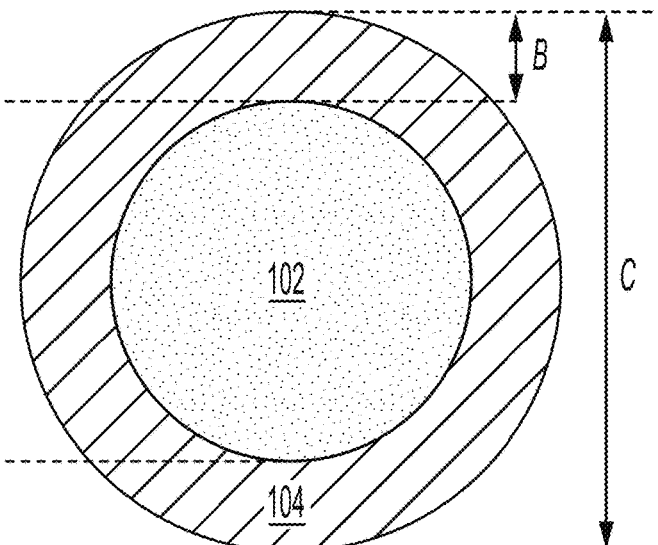
Figure 2C:
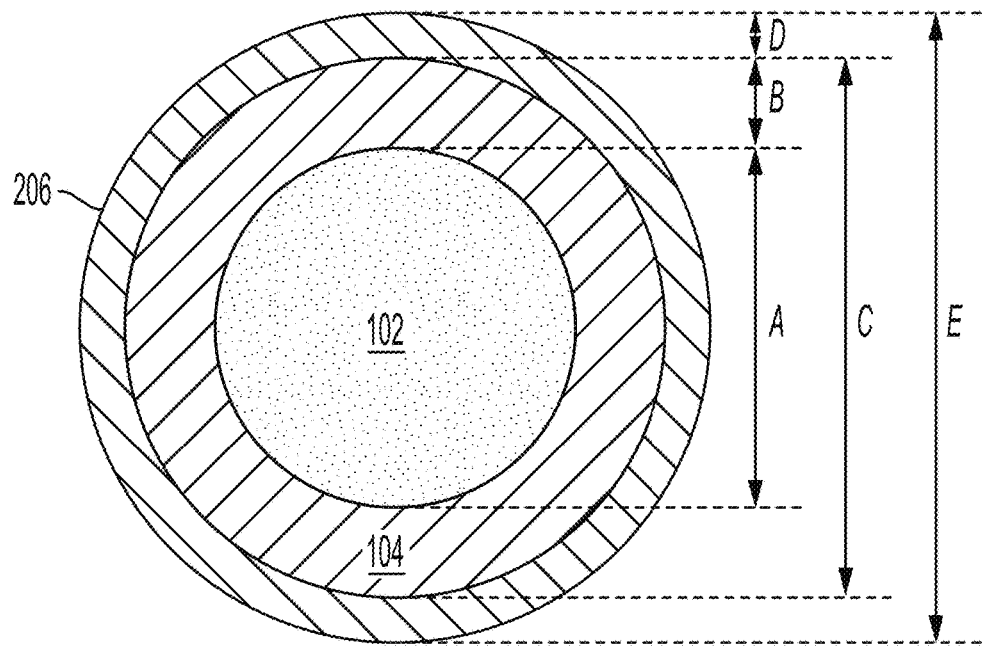

Referring now to FIGS. 2A-2C, electrodes (100) can include a plurality of layers (102, 104, 206) that can have varying diameters and/or thicknesses.

The extracellular matrix core (102) can have a largest-cross-sectional dimension between about 10 µm and about 1,000 µm. For example, the largest cross-sectional dimension can be selected from the group consisting of: between about 10 µm and about 20 µm, between about 25 µm and about 50 µm, between about 50 µm and about 100 µm, between about 100 µm and about 150 µm, between about 150 µm and about 200 µm, between about 200 µm and about 250 µm, between about 250 µm and about 300 µm, between about 300 µm and about 350 µm, between about 350 µm and about 400 µm, between about 400 µm and about 500 µm, between about 500 µm and about 700 µm, and between about 700 µm and about 1,000 µm.

The hydrogel sheath (104) can have a largest-cross-sectional dimension between about 20 µm and about 1,200 µm. For example, the largest cross-sectional dimension can be selected from the group consisting of: between about 20 µm and about 50 µm, between about 50 µm and about 100 µm, between about 100 µm and about 200 µm, between about 200 µm and about 250 µm, between about 250 µm and about 300 µm, between about 300 µm and about 350 µm, between about 350 µm and about 400 µm, between about 400 µm and about 450 µm, between about 450 µm and about 500 µm, between about 500 µm and about 600 µm, between about 600 µm and about 800 µm, and between about 800 µm and about 1,200 µm. Stated another way, the thickness of the hydrogel sheath (104) can be about between about 5 µm and about 400 µm.

The hydrogel sheath (104) can be further surrounded by a layer of carboxymethyl cellulose (CMC). CMC is a cellulose derivative with carboxymethyl groups bound to hydroxyl groups. The functional properties depend on degree of substitution of cellulose structure and degree of polymerization. CMC possesses unique properties in that it is stiff in a dehydrated state and gel-like hydrated state, with a short transition period between states at micro-dimensions. Also, CMC is nontoxic to humans and animals, inexpensive, and widely available. A CMC layer 206 having a thickness of about 15 µm provides sufficient initial rigidity to enable needleless insertion into a subject's brain.

In some embodiments, the hydrogel sheath (104) is replaced entirely by a CMC sheath as depicted and described in International Publication No. WO 2015/066627.

Living electrodes (100) can have varying depths to reflect clinical and anatomical needs. For example, the living electrodes (100) can be sized for insertion to sufficient depth such that second end (110) lies adjacent to a neuronal population/nuclei/layer while first end (108) lies adjacent to (e.g., flush with, slightly below, or slightly proud of) an outer surface of the subject's brain (e.g., for manipulation by light and/or magnetic fields). For example, the electrodes (100) can have a length of about 100 µm to about 2 cm or greater. In some embodiments, the living electrodes can be implanted to a desired depth (e.g., based on imaging and/or feedback) before being trimmed in situ to a desired length relative to the outer surface of the subject's brain.

Neurons

Embodiments of the invention can include optogenetic neurons that enable the use of light to control cells in living tissue that have been genetically modified to express light-sensitive ion channels. For example, the neurons can express one or more optogenetic actuators such as channelrhodopsin, halorhodopsin, and archaerhodopsin and/or one or more optogenetic sensors for calcium (e.g., Aequorin, Cameleon, GCaMP), chloride (e.g., Clomeleon) or membrane voltage (e.g., Mermaid).

Embodiments of the invention can include magnetogenetic neurons which can be controlled in living tissue through the application of an alternating magnetic field. Magnetogenetic techniques are described in Xiaoyyang Long et al., "Magnetogenetics: remote non-invasive magnetic activation of neuronal activity with a magnetoreceptor," 60(24) *Sci. Bull.* 2107-19 (2015).

In certain embodiments, the neurons are genetically modified to secrete factors to modulate disease pathophysiology, to allow transplant cells to be resistant to underlying disease pathophysiology, or to express novel ion channels and receptors to allow for nuanced biological control. For example, genes can be added/modified that allow the neurons to better process/degrade protein accumulations such as pathological alpha-synuclein, tau, or amyloid-beta.

Embodiments of the invention can additionally or alternatively include primary cerebral cortical neurons and/or dorsal root ganglion neurons.

Biocompatibility

The structures described herein can be biocompatible. For example, the structures, when implanted, should not generate an adverse chronic immunogenic or inflammatory response in the subject. In certain embodiments, the one or more elements of the structures degrade over time, thereby leaving the encapsulated axon tracts within the subject. In one embodiment, the living electrodes are generated using allogeneic neurons. Allogeneic neurons should not elicit an overt immunogenic or inflammatory response. In one embodiment, the living electrodes are generated using autologous neurons derived from a patient's own stem cells (e.g., induced pluripotent stem cells) or endogenous stem cell populations such as those found in olfactory epithelium, lingual, ventricular ependymal, or dentate gyrus).

Hydrogels

Hydrogels can generally absorb a great deal of fluid and, at equilibrium, typically are composed more than about 60% fluid and less than about 40% polymer. In a preferred embodiment, the water content of hydrogel is about 80-99.9%. Hydrogels are particularly useful due to the inherent biocompatibility of the cross-linked polymeric network (Hill-West, et al., 1994, Proc. Natl. Acad. Sci. USA 91:5967-5971). Hydrogel biocompatibility can be attributed to hydrophilicity and ability to imbibe large amounts of biological fluids (Preparation and Characterization of Cross-linked Hydrophilic Networks in Absorbent Polymer Technology, Brannon-Peppas and Harland, Eds. 1990, Elsevier: Amsterdam, pp 45-66; Preparation Methods and Structure of Hydrogels in Hydrogels in Medicine and Pharmacy, Peppas, Ed. 1986, CRC Press: Boca Raton, Fla., pp 1-27).

Hydrogels can be prepared by crosslinking hydrophilic biopolymers or synthetic polymers. Examples of the hydrogels formed from physical or chemical crosslinking of hydrophilic biopolymers, include, but are not limited to, hyaluronans, chitosans, alginates, collagen, dextran, pectin, carrageenan, polylysine, gelatin, hyaluronic acid, or agarose. (Hennink and van Nostrum, 2002, Adv. Drug Del. Rev. 54, 13-36 and Hoffman, 2002, Adv. Drug Del. Rev. 43, 3-12). These materials consist of high-molecular-weight-backbone chains made of linear or branched polysaccharides or polypeptides. Examples of hydrogels based on chemical or physical crosslinking synthetic polymers include, but are not limited to, (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (Hoffman, 2002, Adv. Drug Del. Rev, 43, 3-12). In some embodiments, the hydrogel comprises poly(ethylene glycol) diacrylate (PEGDA).

In one embodiment, the hydrogel comprises at least one biopolymer. In other embodiments, the hydrogel scaffold further comprises at least two biopolymers. In yet other embodiments, the hydrogel scaffold further comprises at least one biopolymer and at least one synthetic polymer.

In one embodiment, the hydrogel comprises agarose. The concentration of agarose may, in certain instances, be dependent upon the type of neuron ultimately being cultured, the mechanical properties, desired, or the like. For example, increasing concentrations of agarose enhances neuronal survival and neurite outgrowth. In one embodiment, the concentration of agarose is about 0.1% to about 10%. In one embodiment, the concentration of agarose is about 0.5% to about 5%. In one embodiment, the concentration of agarose is about 4%.

Hydrogels closely resemble the natural living extracellular matrix (Ratner and Hoffman. Synthetic Hydrogels for Biomedical Applications in Hydrogels for Medical and Related Applications, Andrade, Ed. 1976, American Chemical Society: Washington, D.C., pp 1-36). Hydrogels can also be made degradable in vivo by incorporating PLA, PLGA or PGA polymers. Moreover, hydrogels can be modified with fibronectin, laminin, vitronectin, or, for example, RGD for surface modification, which can promote cell adhesion and proliferation (Heungsoo Shin, 2003, Biomaterials 24:4353-4364; Hwang et al., 2006 Tissue Eng. 12:2695-706). Indeed, altering molecular weights, block structures, degradable linkages, and cross-linking modes can influence strength, elasticity, and degradation properties of the instant hydrogels (Nguyen and West, 2002, Biomaterials 23(22):4307-14; Ifkovits and Burkick, 2007, Tissue Eng. 13(10):2369-85).

Molecules that can be incorporated into the hydrogel matrix, for example via covalent linkage, encapsulation, or the like, include, but are not limited to, vitamins and other nutritional supplements; glycoproteins (e.g., collagen); fibronectin; peptides and proteins; neurotransmitters; growth or neurotrophic factors; differentiation factors; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents. Hydrogels may be modified with functional groups for covalently attaching a variety of proteins (e.g., collagen) or compounds such as therapeutic agents. Therapeutic agents which can be incorporated to the matrix include, but are not limited to, analgesics, anesthetics, antifungals, antibiotics, anti-inflammatories, anthelmintics, antidotes, antihistamines, antihypertensives, antimalarials, antimicrobials, antipsychotics, antipyretics, antiseptics, antiarthritics, antituberculotics, antivirals, chemotherapeutic agents, a colored or fluorescent imaging agent, corticoids (such as steroids), antidepressants, depressants, diagnostic aids, enzymes, hormones, hypnotics, minerals, nutritional supplements, parasympathomimetics, potassium supplements, radiation sensitizers, a radioisotope, an imaging contrast agent, sedatives, sulfonamides, stimulants, sympathomimetics, tranquilizers, vasoconstrictors, vasodilators, vitamins, xanthine derivatives, and the like. The therapeutic agent may also be other small organic molecules, naturally isolated entities or their analogs, organometallic agents, chelated metals or metal salts, peptide-based drugs, or peptidic or non-peptidic receptor targeting or binding agents. It is contemplated that in certain embodiments, linkage of the therapeutic agent to the matrix may be via a protease sensitive linker or other biodegradable linkage.

Other suitable hydrogel components are described in International Publication No. WO 2015/066627.

Methods of Implantation

Figure 3:
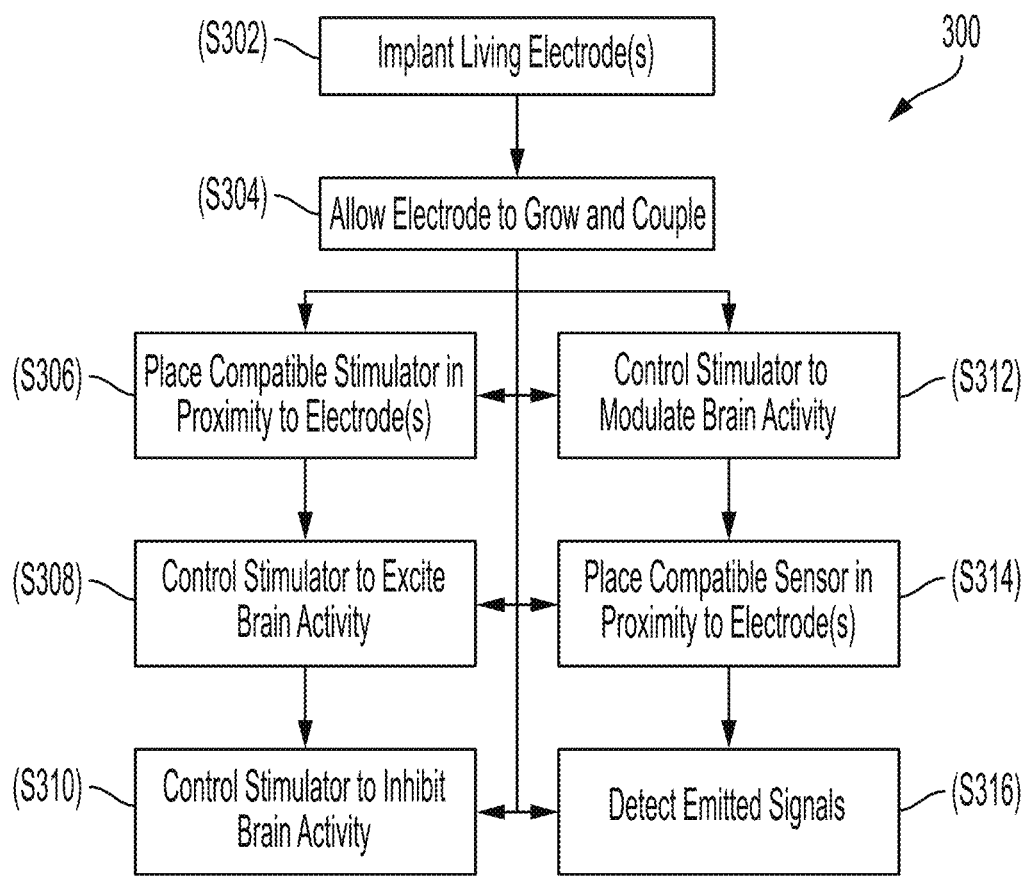
FIG. 3 depicts methods for use of implantable living electrodes according to an embodiment of the invention.

Referring now to FIG. 3, another aspect of the invention provides a method (300).

In step S302, one or more implantable living electrodes are implanted within a subject. Suitable implantation regions include the subject's brain, spinal cord, peripheral nervous system (e.g., peripheral neurons, peripheral axons, axonal pathways, ganglia, dorsal root ganglia, autonomic ganglia, and the like), and muscles. The electrodes can be implanted with or without the aid of imaging and with or without the aid of stereotactic manual or stereotactic automated delivery systems. In some embodiments, multiple electrodes are implanted in a region of interest.

In step S304, the implantable living electrode is allowed to grow and couple with one or more deep adjacent host structures (e.g., host neurons or neural networks), over hours, days, weeks, months, years, or decades. Although initial integration will take place on the order of hours to days, living electrodes can form a stable interface for weeks, months, years, decades, and/or over the lifetime of the implanted individual in contrast to conventional electrodes that that lose effectiveness over time due to chronic foreign body response, mechanical separation issues, reduced neuronal density in electrode vicinity, and glial scarring. Additionally, because the living electrode includes living neurons and axons, synapses formed between construct neurons and host neurons can be permanent and/or experience a natural turnover/plasticity consistent with similar synapses in the subject's body. Other cellular communication points can be formed between the living electrode and host, including but not limited to gap junctions, electrical synapses, and ephaptic links.

In step S306, a compatible stimulator is placed in proximity to at least one of the one or more implantable living electrodes. For example, a light source producing a compatible wavelength of light can be placed at the surface of the subject's brain adjacent to the implanted electrode or outside of the subject's skull, or through the skull across a custom-fit transparent skull-replacement piece. Likewise, compatible magnetic sources can be placed at the surface of the subject's brain or outside of the subject's skull, or through the skull across a custom-fit skull-replacement piece. Likewise, an acoustic source such as ultrasound can be placed at the surface of the subject's brain or outside of the subject's skull.

In steps S308 and S310, the compatible stimulator can be controlled to actuate at least one of the implanted electrodes to excite (S308), inhibit (S310), and/or otherwise modulate (S312) brain activity.

In step S314, a compatible sensor is placed in proximity to at least one of the one or more implantable living electrodes. For example, a light sensor can be placed at the surface of the subject's brain adjacent to the implanted electrode. Likewise, a compatible magnetic sensor can be placed at the surface of the subject's brain or outside of the subject's skull.

In step S316, one or more signals emitted by the implanted electrode(s) are detected by the sensor(s).

In certain embodiments, implantable living electrodes are used to interface with the brain to record or stimulate neurons. Stimulation of neurons can be used for treatment, or as a diagnostic of a particular function or dysfunction of the nervous system. Examples of nervous system dysfunctions can include, but are not limited to Parkinson's disease, Alzheimer's disease, dementia with Lewy bodies, frontotemporal dementia, Huntington's disease, prion disease, motor neurone diseases, spinocerebellar ataxia, spinal muscular atrophy, amyotrophic lateral sclerosis (ALS), encephalitis, epilepsy, head and brain malformations, hydrocephalus, seizures, chronic pain, traumatic brain injury, spinal cord injury, stroke, anoxic brain injury, cerebral palsy, obesity, depression, multiple sclerosis, inflammation, migraines, diabetic neuropathy, locked-in syndrome, glioblastoma, oligodendroglioma, metastases, and the like.

Macro-TENNs

Another embodiment of the invention provides peripheral nerve interface (PNI) electrodes and techniques that provide greater access to different fascicles/axons. A macro-tissue engineered neural network (macro-TENN) is larger and modified specifically for PNS applications. Embodiments of the invention guide axonal regeneration to allow the fascicles of a nerve to spread out circumferentially around the inner surface of the macro-TENN. The separation has the functional utility of being able to separate fascicles and/or axons to gain a level of neural selectivity unavailable with previous technologies.

In addition to use in the peripheral nervous system, macro-TENNs can be used to interface with cranial nerves.

The macro-TENN employs similar techniques to the micro-TENN technology described herein, but a larger hydrogel column results in a tubular construct where the axons only grow along the periphery of the tube. In this manner, the embodiment facilitates the defasciculization of the nerve and/or the spreading out of the axons so that the axons could interface more intimately with a multitude of electrodes in the interior or exterior of the tubular column (arranged circumferentially). Leveraging this method of growth into the tubular construct to spread out the host axons to bring them closer to contacting circumferential surface electrodes would allow for highly selective interfacing (recording or stimulation) with peripheral host axons.

Figure 15A:
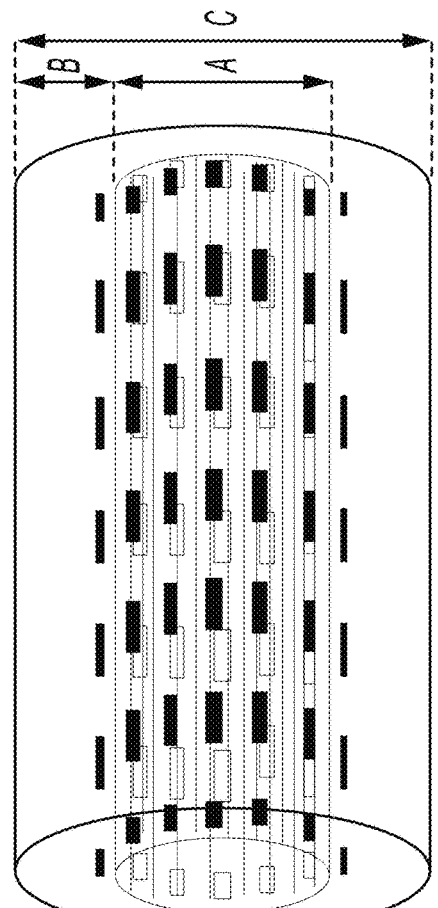
FIGS. 15A-15C depict deployment of electrodes in a defascicularization device according to an embodiment of the invention.
Figure 15B:
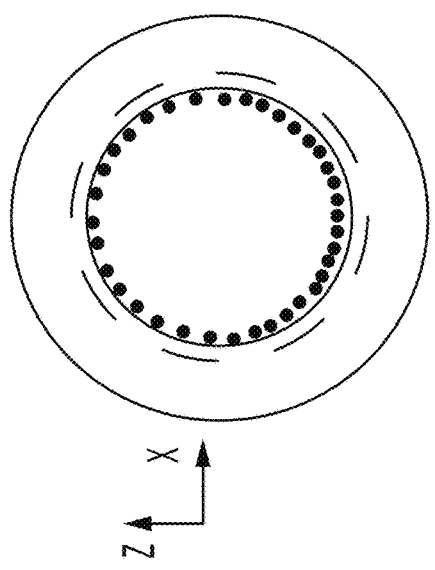
Figure 15C:
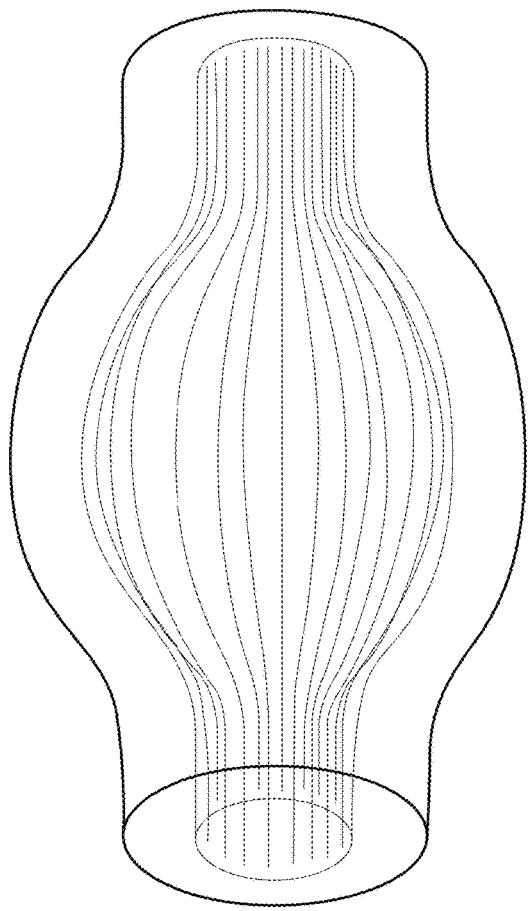

Similar to the micro-TENNs described herein, the macro-TENN can have a bipartite construction of a tubular hydrogel shell (as described above) with an extracellular matrix (ECM) core as depicted in FIGS. 15A-15C. The ECM core can consist of several different components, including, but not limited to laminin and/or collagen (as described above). The axons can grow into the core while the hydrogel allows for transmission of soluble factors into and out of the core channel.

Exemplary dimensions include an extracellular matrix core diameter A of between about 1 mm and about 5 mm (e.g., between about 1 mm and about 2 mm, between about 2 mm and about 3 mm, between about 3 mm and about 4 mm, between about 4 mm and about 5 mm, and the like). Other exemplary dimensions include hydrogel sheath diameter C of between about 2 mm and about 7 mm (e.g., between about 2 mm and about 3 mm, between about 3 mm and about 4 mm, between about 4 mm and about 5 mm, between about 5 mm and about 6 mm, between about 6 mm and about 7 mm, and the like). In some embodiments, the thickness of hydrogel sheath B is between about 1 mm and about 2 mm.

Aggregate TENNs

Another aspect of the invention provides aggregate-TENNs including a substantially cylindrical extracellular matrix core and a plurality of aggregated neurons implanted along or within the substantially cylindrical extracellular matrix core.

Another aspect, of the invention includes a method of manufacturing an implantable living electrode including providing an extracellular matrix core; and contacting at least one end of the extracellular matrix core with a plurality of aggregated neurons.

In various embodiments, aggregate TENNs exhibit higher axonal growth rates than their dissociated counterparts. The term aggregate TENN may encompass TENNS wherein the neurons have been concentrated to form an aggregate prior the construction of the TENN. The term may encompass any method of forming the aggregate. Centrifugation of neurons in a pyramidal well is one method of forming such aggregates. TENNS manufactured using this technique may be referred to as centrifuged TENNs and the terms are used interchangeably herein although a person of skill in the art will appreciate that they are not necessarily coextensive. The observed growth rates for dissociated neurons were similar to those reported in literature; however, axonal growth rates from aggregates greatly exceeded previous reports. Generally, cortical axons reach lengths of 100 to 1000 μm over 3 days in planar culture. The exact causes for this increased growth from aggregates are still under investigation; however, without wishing to be bound by theory, the absence of additional growth factors in the medium and relatively slower growth of dissociated micro-TENNs implicate features of the aggregation method, such as more controlled, in vivo-like neuronal microenvironment and self-reinforcing, more directed axonal extension occurring via growing axon "bundles".

In various embodiments, the extracellular matrix core is a collagen-laminin extracellular matrix core. Laminin is an adhesion molecule, and as such may support rather than accelerate axonal growth. Multiple studies have investigated the relationship between growth cone behavior and axonal growth rate in the mammalian CNS. Notably, axonal branching tends to occur in areas where the growth cone temporarily ceases forward movement, transiently slowing the outgrowth rate. Again, without wishing to be limited by theory, upon emerging from an aggregate, a growth cone within a bidirectional micro-TENN is presented with two classes of targets—neurons within either its own or the opposing aggregate. The combined support/growth promotion of the ECM and limited selection of targets may reduce growth cone pausing/axonal branching, accelerating growth within the zone between the aggregates until the appropriate target is reached. In various embodiments, the distance between axons and their targets may also influence the speed at which they grow, as micro-TENNs within the $LE_{BI,5mm}$ group exhibited faster growth compared to the $LE_{BI,2mm}$ group at 5 DIV. The continued growth up to 10 DIV (albeit at lower rates) of the dissociated micro-TENNs may be attributed to the random distribution of neurons throughout the construct—rather than grow en masse towards an aggregate (a large target for axonal growth and synaptogenesis), neurons continued to grow individually towards their closest neighbors.

In addition to rapid axonal growth, structural evidence of synapses was visualized as early as 4 DIV. Measuring synaptogenesis is often used to determine the functional maturity of neuronal cultures, since synapses are the primary points of contact and communication between neurons. Synapsinpositive puncta were observed between 4 DIV and 28 DIV, suggesting that neurons within micro-TENNs begin to form functional connections soon after plating which greatly increased over time (FIG. 33A-FIG. 33F). Indeed, micro-TENNs at later timepoints qualitatively expressed higher levels of synapsin, consistent with literature for planar cortical cultures where synapse formation tends to increase as a function of time. The presence of synapsin as early as 4 DIV may indicate that micro-TENN neurons are forming functional connections earlier—as may be expected from the high growth rates. Alternatively, many of these synapses may be forming within the aggregates themselves—as the experiments that provided the data for FIG. 33A-FIG. 33F were performed, no distinctions were made between intra-aggregate and inter-aggregate synapses. Intra-aggregate synapses being made before inter-aggregate synapses may explain the high synapsin expression at earlier DIV. Overall, micro-TENN neurons are capable of quickly and consistently forming the desired living electrode architecture in vitro. This allows for the rapid, reproducible production and characterization of aggregate-based micro-TENNs. In various embodiments comprising the aggregate TENN forming method, controlling the aggregate sizes (and, concomitantly, the number of neurons per construct) permits more repeatable studies and standardized production methods than when working with single-cell suspensions. Experimental details regarding aggregate TENNs and methods for their manufacture are presented in FIGS. 16A-16E, 17A-17D, 19A-19B, 23A-23G, 25A-25G, 26A-26H, 29A-31F and 34A-34E as well as in the Examples.

Integral Sensors

Embodiments of the invention can integrate sensory receptors within living electrodes, described herein, to provide integral sensors that can both detect stimulus and transmit a corresponding signal to the subject's nervous system or an external system. For example, a living electrode can include sensory dorsal root ganglion cells and/or cells with specialized sensors such as baroreceptors, chemoreceptors (e.g., type I/glomus cells and type II glial-like cells), electromagnetic receptors (e.g., infrared receptors, photoreceptors, ultraviolet receptors), electroreceptors, hydroreceptors, magnetoreceptors, mechanoreceptors, nociceptors, odor receptors, osmoreceptors, proprioceptors, taste receptors, thermoceptors, and the like. Living electrodes can also include cochlear and/or vestibular hair cells.

Integration with External Sensors

Embodiments of the invention can also be utilized to transmit signals from external sensors to a subject's nervous system or to an external system. For example, a man-made sensor can generate electrical, optical, and/or magnetic signals indicative of conditions such as pressure, temperature, position, force, sound, smell, light, and the like. Embodiments of living electrode structures described herein can receive these signals and transmit/transduce the signals to the subject's nerves.

Integration of Electromechanical Devices within Living Electrodes

Although some embodiments of the invention are described in the context of external electromechanical devices such as surface optrodes that may be adjacent to, but distinct from the living electrodes described herein, other embodiments of the invention can incorporate such devices within the living electrode. For example, electrical contacts can be grown or inserted within the living electrode. Likewise, optrodes, electromagnetic devices, thermoelectric (Joule-Thomson resistive) heaters, thermoelectric (Peltier) coolers, and/or chemical applicators can be grown or inserted within the living electrode. For example, chemical applicators can be adapted and configured to release neural transmitters, ligands to which neurons respond, and/or ions in response to an electrical signal.

Biological Multiplexing

Figures 21A, 21B, 21C:
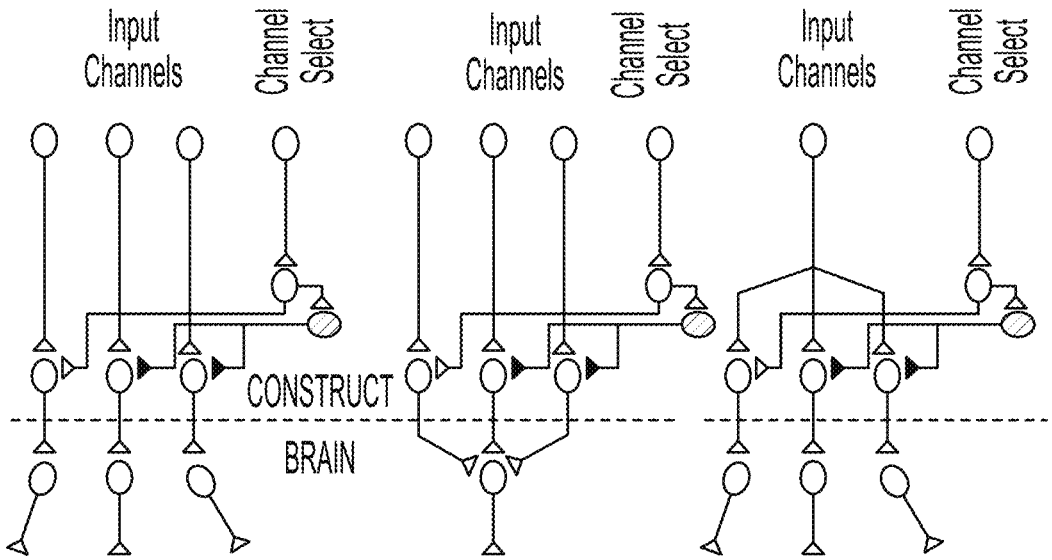
FIG. 21A-FIG. 21C diagram possibilities for exploiting "biological multiplexing" in living electrodes. More sophisticated living electrodes may be developed to further exploit so-called biological multiplexing. By fabricating the constructs in vitro using microprinting and micropatterning techniques, specific synaptic architectures can be achieved to yield certain fine-grained signal manipulations linking the construct to the brain.
Figure 21D:
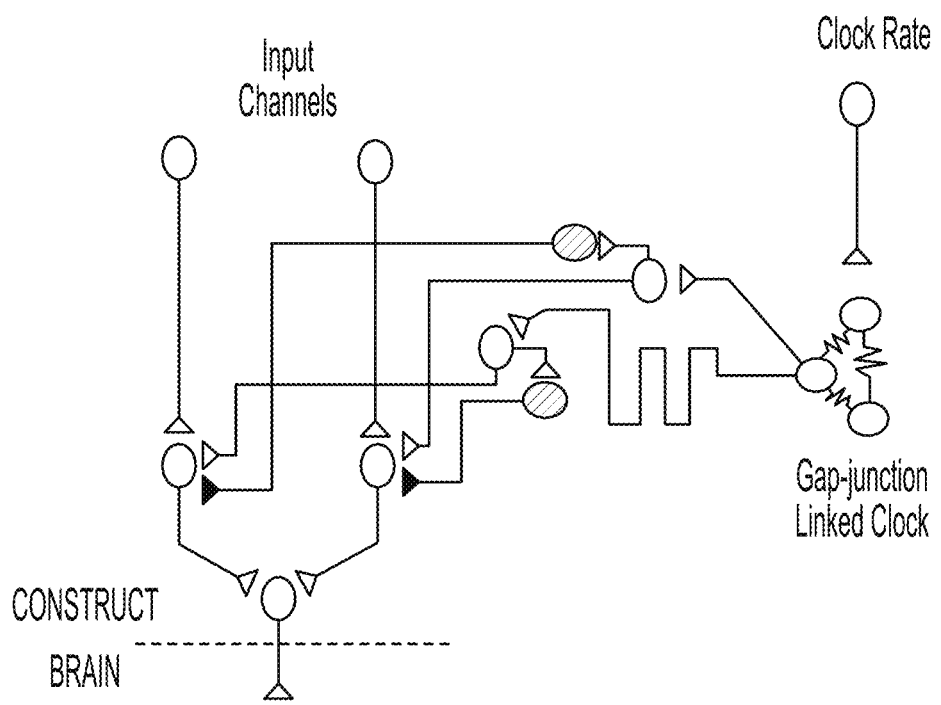
FIG. 21D shows the potential for time-division "biological multiplexing" in living electrodes. Living electrodes may exploit delay lines emanating from a single "clock" circuit formed by a cluster of neurons linked by gap junctions (coupled damped oscillators) and micropatterned inhibitory and excitatory connections. Thus, multiple parallel input channels can be multiplexed serially with each clock cycle to a single target output neuron that in turn links to the brain. The rate of the clock (and hence the multiplexing sampling duration) can be altered by driving the clock circuit directly.
Figure 22:
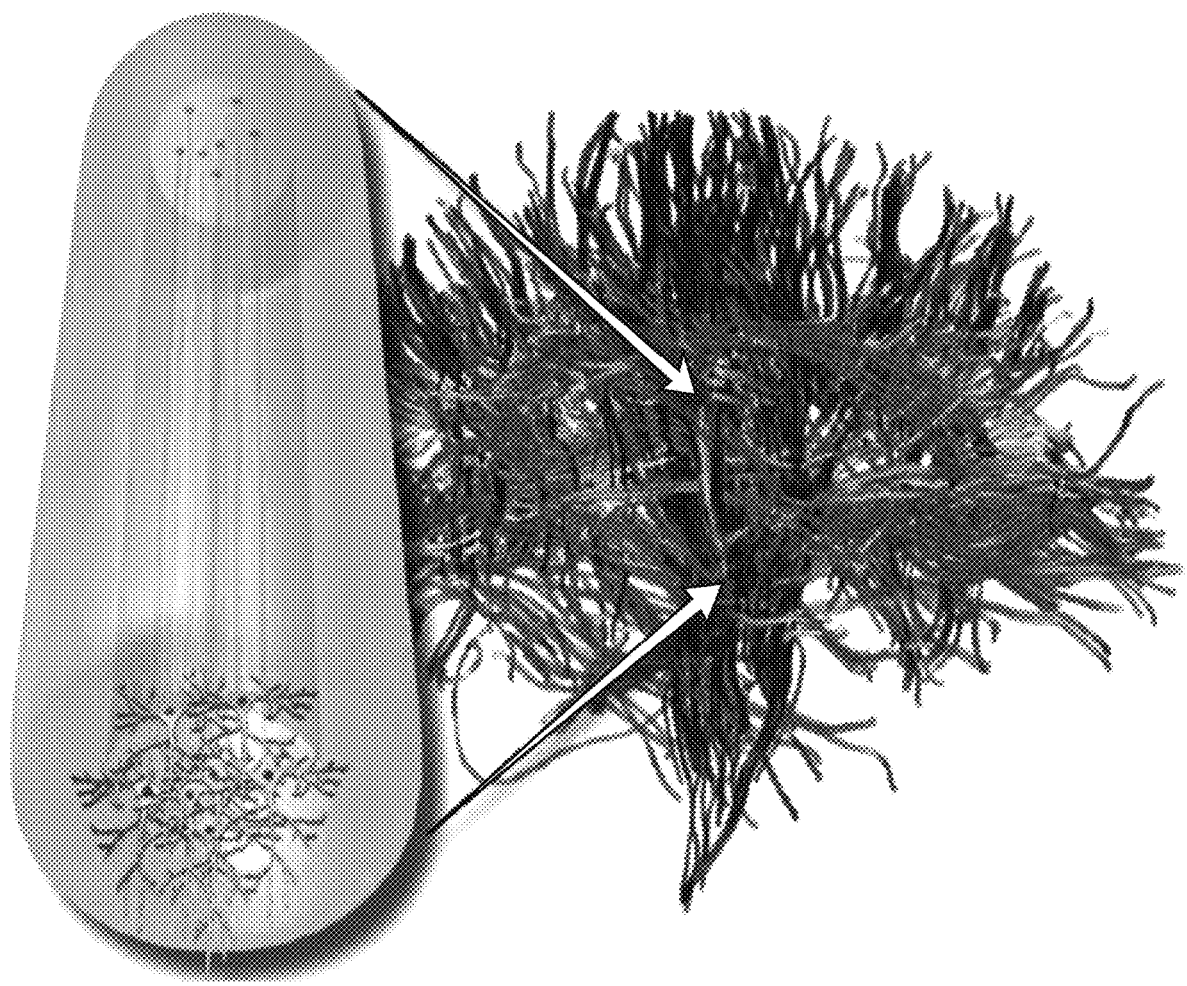
FIG. 22 depicts a diffusion tensor imaging representation of the long-distance axonal tracts that connect discrete populations of neurons in the human brain. This conceptual rendition shows how a unidirectional micro-TENN—consisting of a population of dopaminergic neurons extending long, aligned processes—can be used to recreate the nigrostriatal pathway that degenerates in Parkinson's disease. Axons in the substantia nigra are expected to functionally integrate with the transplanted dopaminergic neurons in the micro-TENN, while the transplanted dopaminergic axons are expected to functionally integrate with neurons in the striatum. After receiving appropriate inputs from the substantia nigra, the transplanted neurons will release dopamine in the striatum, thereby recreating the circuitry lost in Parkinson's disease.
Figure 28A:
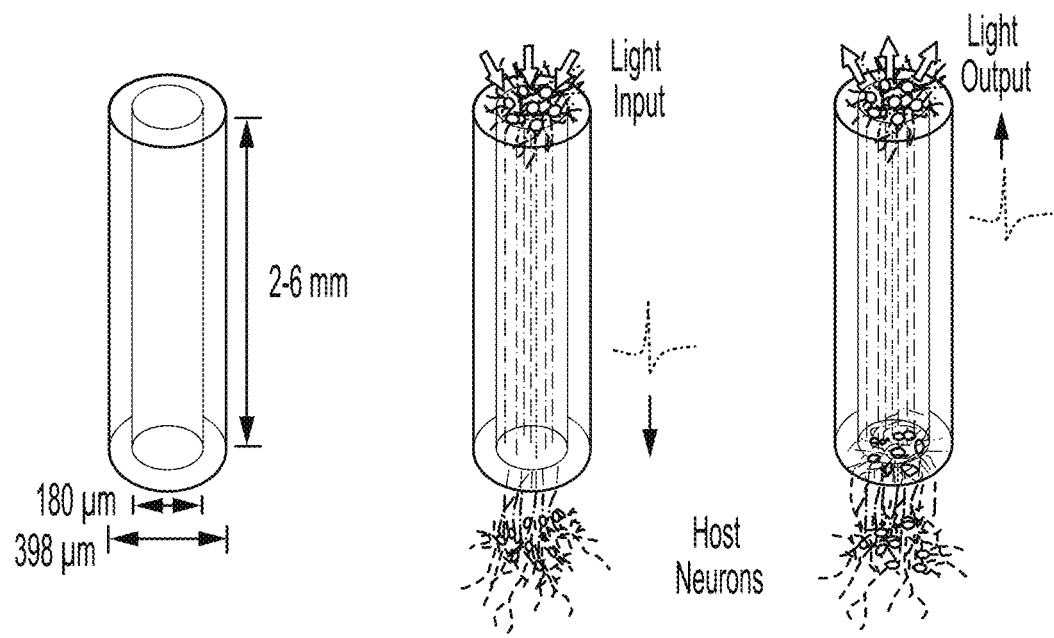
FIG. 28A-FIG. 28B depict micro-TENNs as living electrodes for a Neuroprosthetic Interface.
Figure 28B:
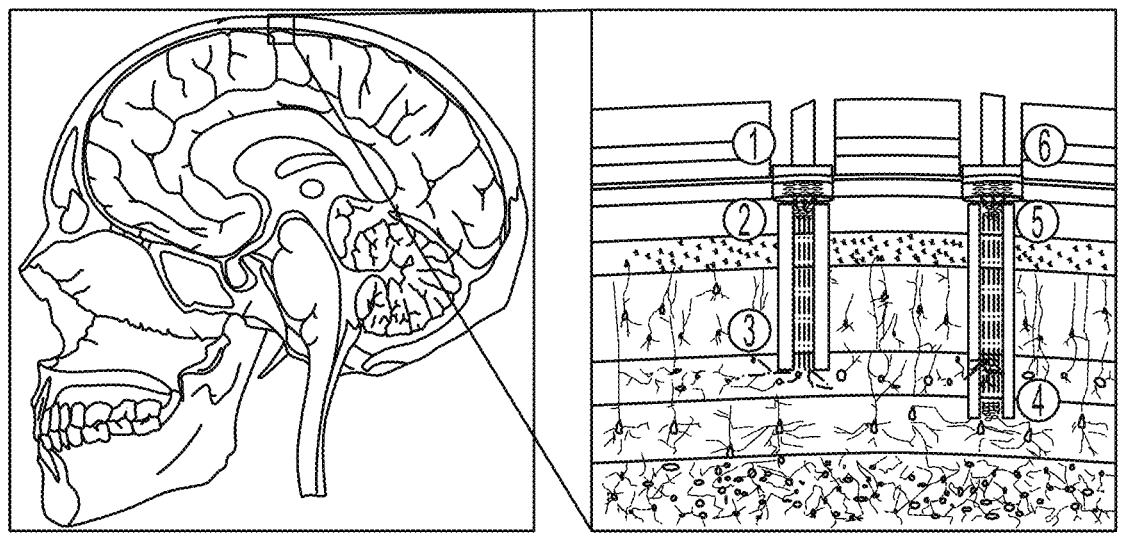

Biological multiplexing can be defined broadly to encompass biological versions of the types of channel selection, multiplexing and demultiplexing used in telecommunications. In some embodiments, biological multiplexing comprises both convergent and divergent signaling: signal processing within many neurons of the construct can converge on to single host parenchyma targets, and one construct neuron can have axons divergently branching to target many host parenchyma neurons (FIG. 21A-FIG. 21C). Likewise, because neurons in the host brain are themselves embedded in endogenous neural networks, the ability of the living construct to send axonal outputs to one of these host neurons allows a specific, stable, activation of that endogenous neural network. Because one axon can in principle synapse onto thousands of target neurons, a relatively small population of neurons within the construct could achieve a widespread effect. By deploying micropatterning techniques, living electrodes can be forged in vitro to enable fine-grained time-division multiplexing when implanted in vivo (FIG. 21D).

Living Electrodes Formed from Stem Cells

In its various aspects and embodiments, the compositions of the invention may be generated from stem cells. In various embodiments, deleterious immune response may be mitigated through the use of autologous cells from patients. Neurons, oligodendrocytes, astrocytes, and Schwann cells can be differentiated from human embryonic stem cells, induced pluripotent stem cells, and adipose-derived stem cells. Although direct in vivo delivery of stem cells may replace lost cells and encourage neural regeneration through the release of trophic factors, the mechanism by which they stimulate the nervous system remains unclear, and they have the potential to differentiate into undesirable phenotypes and/or result in tumorigenesis. In comparison, there are notable advantages to the use of differentiated neurons within living electrodes. Existing protocols to differentiate stem cells into specific neuronal sub-types—such as cortical projection neurons, interneurons, dopaminergic A9 neurons, spinal motor neurons—can be used to engineer living electrodes with specific neuronal compositions. Because neurons are both terminally differentiated and physically constrained by the 3D architecture of the engineered construct, this approach likely carries less risk for tumorigenesis. In various embodiments, differentiated neurons can be genetically modified to enhance regenerative responses. Prior studies suggest that the low survival of transplanted cells can be due to delivery into a degenerating or "hostile" injured environment. In various embodiments, by using transfection techniques or viral transduction, the durability and regenerative potential of differentiated neurons may be augmented through the overexpression of trophic factors. This approach may make engineered tissue resistant to the underlying pathophysiology of neurodegenerative disease.

Controlled Programmed Cell Death Living Electrodes

In various embodiments, the living electrodes herein described may be engineered to contain a controlled "kill switch" driving programmed cell death of living electrode neurons and hence axons. Indeed, the ability to employ different strategies to induce programmed cell death in transplanted constructs is a potentially important method to enhance the safety of living electrodes. There are multiple suicide-gene technologies in development that can be embedded into living electrode constructs. These suicide genes are biologically inert until activated by the introduction of a prodrug, and two clinically validated constructs, iCasp9 and HSV-TK, are well-suited for different situations based on rapid versus gradual apoptosis, respectively as may be appropriate in various embodiments.

Potential Applications for Axon-Based Living Electrodes

In various embodiments, living electrodes may be deployed to augment or replace traditional forms of neuromodulation, or may be applied for more far-reaching drug delivery applications. For instance, living electrodes may be precisely delivered to key locations to influence the strength of specific connections. In various embodiments, inhibitory (e.g., GABAergic) living electrodes may be designed to form synapses to modulate pathways that are exerting too much influence and causing detrimental functional effects, for example to dampen hypersynchronous activity in a circuitry exhibiting epileptiform activity (described in more detail below). Conversely, in some embodiments, excitatory (e.g., glutamatergic) living electrodes may form synapses to augment weak pathways, for example with axons from the construct releasing glutamate at the target of a degenerating pathway. In various embodiments, living electrodes may also act by bulk release of neurotransmitters at the axonal terminal, either via tonic (self-pacing/continuous) activity, by responding to inputs from the host to the living electrode neuronal somata/dendrites, or controlled from externalized hardware or computer.

This type of biological neuromodulation can provide direct (i.e. synaptically-mediated) excitatory or inhibitory inputs—or both simultaneously—or can provide controlled release of diffuse modulatory neurotransmitters (e.g., dopamine) to augment circuit function. Axon-based living electrodes can uniquely fulfill this role—over more common neuronal transplants for instance—by acting based on network feedback relayed and processed reciprocally between the construct and the surrounding brain with the potential for computer-controlled regulation/feedback. A sample of applications for the compositions and methods of the invention is detailed below:

Friedrich's Ataxia

In most cases of Friedrich's ataxia, the expansion of the trinucleotide (GAA) repeat in intron 1 of both alleles of the frataxin gene on chromosome 9q13 leads to reduced transcription of the gene (ie, silencing), decreased expression of the gene product frataxin, and ultimate destruction of the dorsal column pathways. Patients consequently develop severe motor impairments in the absence of proprioceptive and epicritic signals from the periphery. In various embodiments, living electrodes could provide an artificial sensory arc: by tapping into signals from periphery (such as strain gauges, accelerometers and gyroscopes worn at joints in all four limbs, or from implanted cuff recordings of peripheral nerves), living electrodes implanted into primary sensory cortices could provide sensory feedback and allow improved voluntary movement and functional independence. Grown with glutamatergic neurons, these living electrodes could be implanted to terminate in layer IV of the post-central gyms; because living electrodes are themselves quite small, in various embodiments multiple constructs could be implanted corresponding to different joints (e.g., gyros from the left knee driving a living electrode implanted in the right medial sensory cortex, left elbow and shoulder to right lateral sensory cortex, and vice versa for the right extremities and left hemisphere).

Severe Motor Impairment and Sensory Feedback.

In brainstem stroke, spinal cord injury, muscular dystrophy and amyotrophic lateral sclerosis, people are rendered paralyzed because the substrate of voluntary motor control (primary motor cortex) is functionally disconnected from the skeletal muscles (and in certain cases bulbar-pharyngeal muscles also). Neuromotor prosthetics comprise a class of brain-computer or brain-machine interfaces that seek to overcome this paralysis by recording directly from the brain and decoding this recorded activity to control devices in the environment, trigger robotic actuators, or drive implanted neuromuscular stimulators. While several human trials have shown the safety and efficacy of this approach, patients achieve control purely by visual feedback. While the sensory arc may be retained in certain patients with motor neuron or muscular disease, it is lost in complete spinal cord transection and is unavailable in all patients when using external robotics. Several groups have attempted to provide haptic feedback by linking tactile signals to electrical stimulation provided by macro- and micro-electrodes implanted into primary sensory cortex. This type of artificial haptic feedback appears to be effective in non-human primates and has not yet been tested in humans. As with children and adults with Friedrich's ataxia, living electrodes offer the promise of recapitulating and expanding the sensory arc by being implanted directly into the sensory cortex (see FIG. 20B). In addition to embodiments driven by externally worn sensors, in other embodiments, living electrode activity could be triggered by sensors mounted on robotic arms, powered robotic exoskeletal braces, wheelchair components and other assistive devices. In this way, a paralyzed patient could literally "feel" their own limbs and the "limbs" of these devices to facilitate enhanced voluntary control. Additionally, by providing a bidirectional interface to both motor and sensory cortex that is routed through internally implanted microprocessors, in various embodiments the living electrodes could modulate inter-cortical communication in a real-time closed-loop to restore motor function and sensory/proprioceptive feedback.

Chronic Pain

In various embodiments, tailored living electrodes may be useful to modulate inputs to a pain-dampening circuit. In various embodiments, living electrodes could be created using peptidergic neurons secreting endorphins or enkephalins and then implanted in the substantia gelatinosa of the spinal cord, the periaqueductal gray, ventroposterior thalamus or the anterior cingulate cortex. In various embodiments, this would replace the non-specific approaches of spinal and brain electrical stimulators. In various embodiments, control of this neuromodulation could be user-dependent (e.g., analogous to a systemic pharmaceutical pump) and, unlike microfluidics that would directly inject opiates or other peptides, and unlike electrodes that would non-specifically modulate a target volume, living electrodes comprised of neurons would themselves undergo up- and down-regulation hence providing additional prophylaxis against the development of tolerance, abuse or withdrawal.

Alzheimer's Disease and Dementia with Lewy Bodies

A hallmark of both Alzheimer's disease (an amyloid-tauopathy) and dementia with Lewy bodies (an alpha-synucleinopathy), is loss of cholinergic neurons in the basal forebrain. These neurons are reciprocally linked to medial temporal lobe structures, including the hippocampal formation, and are necessary to form episodic memories. In various embodiments, living electrodes built using cholinergic neurons could be implanted into the septal nuclei or other adjacent basal forebrain nuclei such as the nucleus basalis of Meynert or the diagonal band of Broca. In various embodiments, a living electrode stereotactically implanted in the basal forebrain and semi-externalized to the brain service (following the path of the columns of the fornix) could allow closed-loop control with external computers: different subpopulations of neurons within the living electrode (cholinergic, GABAergic, glutamatergic) could be triggered differentially via optogenetics and intraosseous anchored waveguides, depending on detection of memory interference local field potential signatures decoded from the activity of separate living electrodes implanted into the temporal lobe to enhance episodic encoding. Likewise, in other embodiments, external cues (e.g., reminders on a smart phone, and user-triggered push button flagging) could be used to modulate basal forebrain activity to enhance storage and recall. In various embodiments, a second living electrode could be implanted into entorhinal cortex and the hippocampus and then linked, via external computers, to the living electrode implanted into the basal forebrain to functionally re-instantiate the bidirectional fornix septohippocampal pathway.

Frontotemporal Dementia and Autism Spectrum Disorder

In another aspect, for agrammatic primary progressive aphasia, a frontotemporal dementia tauopathy affecting the dominant inferior frontal gyrus, living electrodes could be implanted both to link Broca's area to premotor and primary motor cortices (to compensate for aphemia and allow motor substitution gestures) and to link Broca's area to Wernicke's area as an artificial arcuate fasciculus. In embodiments directed to behavioral variant frontotemporal dementia (a TDP-43opathy and sometimes tauopathy), constructs linking degenerating orbitofrontal cortices to intact dorsolateral prefrontal, frontopolar, and anterior cingulate cortices could reinstantiate behavioral inhibition and self-regulation. In embodiments directed to the semantic dementia variant of FTD (TDP-43 or tau), degeneration of the fronto-ventral aspects of the temporal lobe may occur leading to loss of semantic knowledge stores and a variety of reading and perceptual disturbances. In various embodiments, an excitatory glutamatergic living electrode implanted into the visual word form area of the fusiform gyrus may boost residual function in this area, and the living electrode could be crafted as an auxiliary axonal bundle linking primary and secondary visual cortical areas to the ventral temporal lobe to recreate the lost "ventral-what" pathway and restore semantic processing. In both autism-spectrum disorder and behavioral variant frontotemporal dementia, social perception and interaction are compromised. In various embodiments, a living electrode built with glutamatergic neurons at the surface and within left dorsolateral prefrontal cortex and oxytocinergic neurons apposed to supraoptic and paraventricular nuclei in the hypothalamus could quench behavioral disinhibition and recover social behavior; the surface cortical population could be triggered by external computers tracking social cues decoded from microphones and micro-cameras mounted unobtrusively in the frames of glasses, hearing aids, bracelets or other apparel.

Stroke and Cerebral Palsy

Both ischemic and hemorrhagic stroke result in focal brain tissue destruction and varying degrees of inflammation. In ischemic stroke, a surrounding penumbra of tissue may remain functional and simultaneously metabolically vulnerable to further insult (such as from decreased blood pressure or hypoxia). When occurring in utero or in the perinatal period, stroke (e.g., germinal matrix hemorrhage) can lead to a static insult around which the rest of the brain attempts to develop normally, in certain cases leading to cerebral palsy with varying degrees of motor and cognitive impairment. When an area of the brain is damaged, two aspects of function are lost: the local gray matter "computation" and also the axonal (both focal intrinsic and also crossing fibers of passage) "connectivity." In various embodiments, micro-TENNs could directly restore both computation and connectivity and serve as "replacement parts" for the irreversibly damaged piece of the brain and to metabolically, electrically and functionally revive and support the surrounding penumbra. In an animal model of stroke with middle cerebral artery occlusion, optogenetic grafts were shown to restore functional mobility. Whereas this graft was "driven" by an external laser, a functionalized living electrode could allow both intact areas of the brain, and external modulation triggered by body sensors or computer-driven rehabilitation, to do the "driving" to restore activity within the penumbra and restore functional mobility and behavior following stroke.

Refractory Depression

Severe clinical depression that is refractory to pharmacotherapy, psychotherapy and electroconvulsive therapy, is characterized by neurometabolic derangements including disrupted glucose uptake in limbic structures including the cingulate gyrus. In various embodiments, micro-TENNs could be implanted to enhance connectivity between frontopolar cortex and the anterior cingulate, or to link supragenual to subgenual anterior cingulate cortices so that the former modulates the latter to restore normal metabolic activity and relieve symptoms. Likewise, in various embodiments, if seeded with dopaminergic neurons, living electrodes implanted into the nucleus accumbens could be deployed to provide dynamic, phasic alteration of catecholamine tone and hence alter mood salience labeling of thoughts and perception to relieve depressive symptoms without causing rebound dysphoria or tolerance post-synaptic upregulation.

Epilepsy

The application for epilepsy exhibits two ways in which the advanced functionality of living electrodes could achieve treatment goals in a manner impossible with existing approaches. In the first, living electrodes could be forged such that the population of neurons closest to the target area secreted the inhibitory neurotransmitter GABA diffusely to the target region, either constitutively or evoked from the brain surface based on measurements of early epileptiform activity (as described below). In this approach, the living electrode effectively serves as a GABA reservoir and delivery system (see FIG. 20C). In various embodiments, the living electrode could be seeded with excitatory glutamatergic neurons in an extracellular matrix decorated with neuroligins to coax synaptogenesis with local endogenous GABAergic neurons. Either approach may achieve disruption of hypersynchronous activity and hence arrest generation or transmission of pathological seizures from a target region in the brain. Because neurons in the epileptiform network within the brain may form synapses onto dendrites extending out from neurons within the construct, various embodiments may achieve focal, closed-loop self-attenuating circuits such that focal epileptiform activity would quench itself via this autoinhibitory loop mediated by the inhibitory living electrode. In embodiments directed toward multi-focal epilepsy, living electrodes could be implanted at two or more epileptigenic foci (e.g., identified by intracranial surface and depth recording). In various embodiments, sensors (e.g., intraosseous or subgaleal leads capturing ongoing local field potentials) could be used to pick up signatures of pre-seizure or seizure activity to trigger photostimulation of optogenetically modified surface externalized micro-TENNs to pre-emptively arrest seizure propagation in a manner impossible with conventional electrodes.

Parkinson's Disease

In a further aspect, the invention provides micro-TENN compositions and methods for the treatment of Parkinson's disease. In one aspect, the invention comprises a substantially cylindrical extracellular matrix core; one or more neurons implanted along or within the substantially cylindrical extracellular matrix core, wherein the neurons are dopaminergic neurons. In another aspect, the invention comprises a method of treating Parkinson's disease comprising implanting a dopaminergic micro-TENN into the SNpc of a patient.

Current treatments for Parkinson's disease, including the use of dopamine replacement strategies and deep brain stimulation, are aimed at alleviating motor disabilities rather than correcting the underlying cause of the motor symptoms. Furthermore, while dopaminergic neuron and/or fetal graft implants into the striatum may provide a local source of dopamine, these approaches do not recreate the nigrostriatal circuit. To address these gaps, a tissue-engineered solution that could be precisely delivered to physically restore lost dopaminergic neurons in the SNpc and their axonal projections to the striatum is sought. To achieve this objective, in one aspect the invention comprises micro-TENNs utilizing primary dopaminergic neurons. It was found that micro-TENNs plated with neuronal aggregates grew more than 6 mm in length when fabricated with the optimal inner core ECM. Furthermore, the dopaminergic micro-TENNs exhibit evoked dopamine release and are capable of synapsing with a population of striatal cells in vitro, and show survival and maintenance of cytoarchitecture upon transplant in vivo.

Dopaminergic micro-TENNs may be fabricated using a population of ventral mesencephalic neurons that, may be enriched in dopaminergic neurons, some embodiments are not a pure dopaminergic population. Other embodiments comprise a pure dopaminergic population. In various embodiments a higher purity of dopaminergic neurons may be used for functional efficacy, in other embodiments a later developmental time point for midbrain isolation cell sorting, and/or differentiation from stem cell sources may be used, all of which have been shown to further enrich dopaminergic populations.

In another aspect, the invention comprises a method to plate micro-TENNs with dopaminergic "aggregates" that may alleviate the lack of separation between the neuronal somata and neurites that was observed in some cases when micro-TENNs were plated with dissociated cells. It was particularly important to ensure that the micro-TENNs demonstrated the desired cytoarchitecture of a discrete cell body region projecting axons through the length of the inner core since separate somatic and axonal regions is a key feature of the nigrostriatal pathway.

Without wishing to be limited by theory, it is believed that better approximation of the cytoarchitecture of the nigrostriatal pathway leads to improved functional outcomes following micro-TENN implantation to reconstruct the degenerated dopaminergic neurons in the SNpc and their projections to the striatum. In particular, the dopaminergic neurons in the SNpc synapse directly onto striatal neurons without exerting their effects through intermediate synapses and/or neurons. Therefore, in order for the connectivity and timing of micro-TENNs to be correct upon integration with the host, the micro-TENNs will likely need to achieve modulation of striatal neurons by propagating signals from the SNpc through a mono-synaptic pathway. Dopaminergic micro-TENNs that approximate the architecture of the nigrostriatal pathway are disclosed herein, and these possess an increased the likelihood that functional integration in vivo will emulate the native mono-synaptic pathway.

In some embodiments, the dopaminergic cell aggregates produced neurite outgrowth that was approximately 10× longer than projections from individual cells. Again, without wishing to be limited by theory, this may be influenced by the fact that the cellular density within the neuronal aggregates is more representative of the density within the brain. This higher cell density may give the aggregated neurons better control over their 3D microenvironment than dissociated cells, which, in turn, promoted better cell viability and health and therefore enhanced axonal extension. Moreover, the gene expression of cells in the aggregates may also be more representative of cells in the brain and allows the cells to tap into developmental programs to initiate axonal outgrowth. Furthermore, many neuronal subtypes are programmed for either short or long distance communication. In dissociated micro-TENNs, "long distance" axons likely meet synaptic partners at intermediate distances along the length of the micro-column. In contrast, for the aggregate micro-TENNs, the absence of any intermediate neighbors may have prompted the "long distance" neurons to up-regulate proteins for long distance outgrowth and thus project the length of the micro-columns. Lastly, the aggregates give rise to grouped and fasciculated axonal projections, which may produce a sustained drive for axonal extension due to concentrated and persistent progrowth signaling, and/or physical/structural advantages. The rates and lengths of dopaminergic axonal extension from the neuronal aggregates were unprecedented, although clearly further studies are required to elucidate the mechanisms of ultra-long axonal projections from the aggregates.

In some embodiments, the aggregate micro-TENNS comprise collagen I and a collagen I and laminin cocktail in the inner core. Without wishing to be bound by theory, it is believed that this configuration benefits axonal outgrowth because, unlike the laminin coating and empty cores, the collagen I and collagen I and laminin cocktail both provide a continuous, 3D scaffold that supports axonal outgrowth. While crosslinked collagen also provides a continuous scaffold, it is much stiffer and likely more resistive to enzymatic degradation upon growth cone extension, however embodiments comprising cross-linked collagen may possess desirable structural properties that may be suitable for various applications.

In various embodiments, the dopaminergic micro-TENNs release dopamine both within the neuronal aggregate and at the axon terminals.

At one week and one month following injection of GFP+ micro-TENNs to span the nigrostriatal pathway, evidence of micro-TENN survival and maintenance of cytoarchitecture was found. Specifically, surviving GFP+ and TH+ neurons were located within the lumen along the injection trajectory. Out to one month post-implant, histological sections orthogonal to the implant trajectory revealed dense GFP+ neurons/axons and TH+ axons in cross-section. The circuitry of the nigrostriatal pathway is complex, and while the trajectory of implantation may be refined in future studies, these findings are sufficient to demonstrate proof-of-concept for implant and survival in vivo.

Figure 20A:
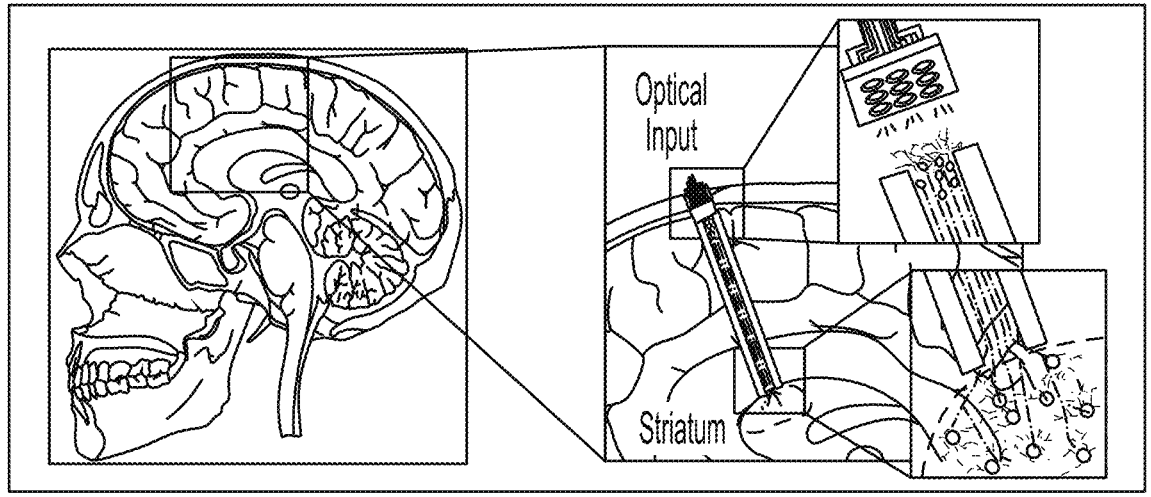
FIG. 20A-FIG. 20C depict potential applications of axon-based living electrodes: custom engineered living electrodes consisting of a phenotypically-controlled population of neurons extending long axonal tracts through a biocompatible micro-column may be stereotactically transplanted to span various regions to treat particular disease processes.
Figure 20B:
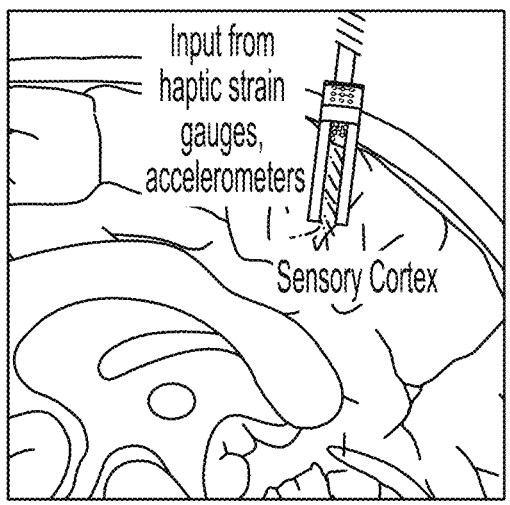
Figure 20C:
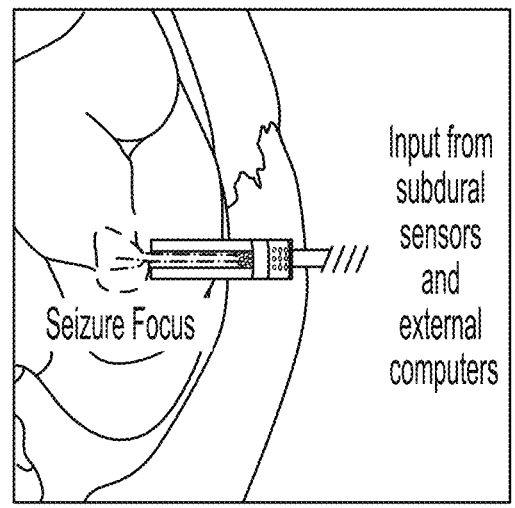

In various embodiments, dopaminergic output of the micro-TENN may be continuously modulated by striatal feedback and SNpc input to alleviate potential runaway dopamine excess and dystonia, a potential side effect from mesencephalic dopaminergic cell transplants into the striatum. Micro-TENNs are an auxiliary pathway. This engineered circuit is unique in that it is mimicking the function of dopaminergic axons projecting from the SNpc to the striatum and seeks to provide dopaminergic inputs that can be tuned and controlled. In addition to direct circuit reconstruction, in various embodiments optogenetically active micro-TENNs may also be deployed as dopaminergic living electrodes to provide controlled neuromodulatory input via engineered axonal tracts (see FIG. 20A). In FIG. 20A-FIG. 20C the neuronal somata population is left quasi-externalized on the brain surface to allow for controlled interface with a sub cranial micro-LED array. The interface beyond the nigrostriatal tract would provide a mechanism whereby information from other brain areas (e.g., beta oscillations recorded from primary motor cortex, external sensors (e.g., gyroscopes and accelerometers both within the battery case in the chest wall or streamed from implanted or externally worn sensors in the hands or feet), and external computers (e.g., processing 3D motion capture and force sensors embedded in the shoes, treadmill and gait analyzer surfaces), could modulate the basal ganglionic circuitry into a healthier activity pattern.

EXAMPLES

The following Examples may be useful to a person of skill in the art in understanding the disclosure but should in no way be construed as limiting the invention.

Various materials and methods employed in certain of the following examples are here presented. All procedures were approved by the IACUCs at the University of Pennsylvania and The Michael J. Crescenz Veterans Affairs Medical Center and were carried out in accordance with Public Health Service Policy on Humane Care and Use of Laboratory Animals (2015).

Three-Dimensional Micro-TENN Fabrication

All supplies were from Invitrogen, BD Biosciences, or Sigma-Aldrich unless otherwise noted. Micro-TENNs included an agarose ECM hydrogel molded into a cylinder through which axons could grow. The outer hydrogel structure consisted of 1% agarose in Dulbecco's phosphate-buffered saline (DPBS). The agarose cylinder, with an outer diameter of 398 μm, was generated by drawing the agarose solution into a capillary tube (Drummond Scientific) via capillary action. An acupuncture needle (diameter: 160 μm) (Seirin) was inserted into the center of the agarose-filled capillary tube in order to produce an inner column. Cured micro-columns were pushed out of the capillary tubes and placed in DPBS where they were cut to 6-12 mm in length and sterilized under UV light (1 hour). 5 μL of the appropriate ECM cocktail was added to each micro-column. ECM cocktails included: rat tail type 1 collagen, 1.0 mg/mL; rat tail type I collagen, 1.0 mg/ml mixed with mouse laminin, 1.0 mg/ml; mouse laminin, 1.75 mg/ml; and rat tail type 1 collagen, 1.0 mg/mL in 11.70 mM N-(3-Dimethylaminopropyl)-N'-ethylcarboiimide hydrochloride, 4.3 mM N-Hydroxysuccinimide, and 35.6 mM sodium phosphate monobasic. These micro-columns were then incubated at 37° C. for 15-30 minutes, after which DPBS was added to the petri dish.

Neuronal Cell Culture

Female Sprague-Dawley rats (Charles River) were the source for primary ventral mesencephalic neurons, a midbrain region previously shown to be enriched in dopaminergic neurons (Weinert et al. 2015, Isolation, culture and long-term maintenance of primary mesencephalic dopaminergic neurons from embryonic rodent brains, Journal of visualized experiments: JoVE, (96)). Carbon dioxide was used to euthanize timed-pregnant rats (embryonic day 14), following which the uterus was extracted. The brains were removed in Hank's balanced salt solution (HBSS) and the ventral midbrain was isolated. The ventral midbrains were dissociated in accutase for 10 minutes at 37° C. The cells were centrifuged at a relative centrifugal force (RCF) of 200 for 5 minutes and resuspended at 1-2 million cells/mL in standard media consisting of NEUROBASAL® medium+ 2% B27+1% fetal bovine serum (Atlanta Biologicals)+2.0 mM Lglutamine+100 μM ascorbic acid+4 ng/mL mouse basic fibroblast growth factor (bFGF)+0.1% penicillin-streptomycin). High concentration growth media consisted of NEUROBASAL® medium+2% B27+1% fetal bovine serum (Atlanta Biologicals)+2.0 mM Lglutamine+100 μM ascorbic acid+0.1% penicillin-streptomycin+12 ng/mL mouse bFGF+10 ng/mL brain-derived neurotrophic factor (BDNF)+10 ng/mL glial cell-derived neurotropic factor (GDNF)+10 ng/mL ciliary neurotropic factor (CNTF)+10 ng/mL cardiotrophin. Dopaminergic neuron aggregates were created based on protocols adapted from Ungrin M D, Joshi C, Nica A, et al. 2008, Reproducible, ultra high-throughput formation of multicellular organization from single cell suspension-derived human embryonic stem cell aggregates, PloS one, 3 (2): e1565. Custom-built arrays of inverted pyramidal wells were fabricated using polydimethylsiloxane (PDMS) (SYLGARD® 184, Dow Corning) cast from a 3D printed mold and placed in a 12-well plate. 12 μL of the cell solution was transferred to each pyramidal well, and the 12-well plate was centrifuged at 1500 rpm for 5 minutes, after which 2 mL of standard media was placed on top of each array. The centrifugation resulted in forced aggregation of neurons (approximately 3,200 cells per aggregate). The wells were then incubated overnight. At the time of plating, the DPBS was removed from the dishes containing the micro-columns and replaced with media. Using forceps, the aggregates were inserted into one (unidirectional) or both (bidirectional) ends of the micro-columns, and the cultures were placed in an incubator (total micro-TENNs created with dopaminergic neurons: n=300).

For micro-TENNs containing dissociated cells with no ECM core, dopaminergic cells were suspended in standard media at 10 million cells/mL and 5 µL of this cell suspension was added to each micro-column. The micro-TENNs were incubated for 60 minutes, after which media was added. For micro-TENNs containing dissociated cells with an ECM core, dopaminergic cells were suspended in rat tail type 1 collagen, 1.0 mg/mL (10,000,000 cells/mL) at the time of plating and 5 µL of this mixture was added to each micro-column. The micro-TENNs were incubated for 15 minutes, after which media was added.

Pre-warmed media was used to replace the culture media every 3-4 days in vitro (DIV). In some instances, micro-TENNs were transduced with an adeno-associated virus (AAV) vector (AAV2/1.hSynapsin.EGFP.WPRE.bGH, UPenn Vector Core) to express green fluorescent protein (GFP) in the neurons. Here, at 3 DIV the micro-TENNs were incubated overnight in media containing the vector (3.2×$10^{10}$ genome copies/mL) and the cultures were rinsed with media the following day.

Female Sprague-Dawley rats (Charles River, Wilmington, Mass.) were the source for primary striatal neurons. Carbon dioxide was used to euthanize timed-pregnant rats (embryonic day 18), after which the uterus was extracted. To isolate striatal neurons, the brains were removed in HBSS and striata were isolated. The striata were dissociated in trypsin (0.25%)+ethylenediaminetetraacetic acid (EDTA) (1 mM) for 12 minutes at 37° C. The trypsin-EDTA was then removed and the tissue was triturated in HBSS containing DNase I (0.15 mg/mL). The cells were centrifuged at 1000 rpm for 3 minutes and resuspended at 1-2 million cells/mL in NEUROBASAL® medium+2% B27+0.4 mM Lglutamine. Striatal aggregates were created and inserted into micro-TENNs as previously described. When testing if dopaminergic aggregates would form synapses with striatal aggregates, striatal aggregates were inserted into the vacant ends of dopaminergic micro-TENNs at 10 DIV. When testing if striatal aggregates would increase the growth rate of dopaminergic micro-TENNs, they were inserted at 3 DIV.

Immunocytochemistry

Micro-TENNs were fixed in 4% formaldehyde for 35 min and permeabilized using 0.3% Triton X100 plus 4% horse serum for 60 minutes. Primary antibodies were added (in phosphate-buffered saline (PBS)+4% serum) at 4° C. for 12 hours. The primary antibodies were the following markers: (1) β-tubulin III (1:500, Sigma-Aldrich, cat #T8578), a microtubule element expressed primarily in neurons; (2) tyrosine hydroxylase (TH; 1:500, Abcam, cat #AB113), an enzyme involved in the production of dopamine; (3) microtubule-associated protein 2 (MAP-2) (1:500, Millipore, cat #AB5622), a microtubule-associated protein found in dendrites; (4) dopamine-and-cAMP-regulated neuronal phosphoprotein (DARPP-32) (1:250, Abcam, cat #AB40801) a protein found in striatal medium-sized spiny neurons; and (5) Synapsin 1 (1:1000, Synaptic Systems, cat #106001), a protein expressed in synaptic vesicles of the central nervous system. Appropriate fluorescent secondary antibodies (Alexa-488, -594 and/or -649 at 1:500 in PBS+30 nM Hoechst+4% serum) were added at 18-24° C. for 2 hours.

Transplantation of Micro-TENNs

Male Sprague-Dawley rats (325-350 g) were anesthetized with isoflurane and mounted in a stereotactic frame. The scalp was cleaned with betadine, bupivacaine was injected along the incision line, and a midline incision was made to expose the Bregma landmark. A 5 mm craniectomy was centered at the following coordinates in relation to Bregma: +4.8 mm (AP), 2.3 mm (ML). The micro-TENN was loaded into a needle (OD: 534 µm, ID: 420 µm; Vita Needle, Needham, Mass.) attached to a Hamilton syringe mounted on a stereotactic arm. The stereotactic arm was positioned at 34° relative to the horizontal plane, the dura was opened, and the needle lowered into the brain to a depth of 11.2 mm. The needle was kept in place for 10 seconds, at which time a stationary arm was positioned to contact the plunger of the Hamilton syringe. The needle containing the micro-TENN was then withdrawn from the brain. The scalp was sutured closed and buprenorphine was provided for postoperative analgesia. Animals receiving micro-TENNs were survived for either 1 week (n=5) or 1 month (n=5). At the time of sacrifice, animals were anesthetized and underwent trans-cardial perfusion with heparinized saline followed by 10% formalin.

Immunohistochemistry

After 24 hour post-fix in 4% paraformaldehyde, brains were prepared for either paraffin processing or cryosectioning. Brains were blocked sagittally and processed through paraffin or put into 30% sucrose until saturated and frozen. Sections were cut at 8 µm (paraffin) or 35 µm (cryosections), mounted on slides, and processed for immunohistochemistry.

Paraffin sections were deparaffinized and then rehydrated Endogenous peroxidase was quenched using 3% hydrogen peroxide in water (Fisher, cat #S25359) followed by heat-induced epitope retrieval in TRIS-EDTA. Sections were blocked with horse serum (ABC Universal Kit, Vector Labs, cat #PK-6200) for 30 min. Rabbit anti-TH (1:750; Abcam, cat #ab112) was applied in Optimax buffer overnight at 4° C. The antigen of interest was visualized using DAB (Vector Labs, cat #SK-4100). Frozen sections were blocked with 5% normal horse serum in 0.1% Triton-x/PBS for 30-45 minutes. Primary antibodies (Rabbit anti-TH, 1:750, Abcam AB112; Mouse anti-Tuj1, 1:1000, Sigma T8578) were applied to the sections in 2% horse serum/Optimax® buffer for two hours at room temperature. Secondary antibodies (1:1000) were applied in 2% horse serum/PBS for one hour at room temperature. Sections were counterstained with Hoechst.

Microscopy and Data Acquisition

For in vitro analyses, micro-TENNs were imaged using phase-contrast and fluorescence on a NIKON® ECLIPSE® Ti-S microscope with image acquisition using a QICLICK® camera interfaced with NIKON® ELEMENTS™ software. In order to determine the length of neurite penetration, the longest observable neurite in each micro-TENN was measured from the proximal end of the neuronal aggregate after fixation. For in vitro immunocytochemistry analyses, cultures and micro-TENNs were fluorescently imaged using a NIKON® A1RSI Laser Scanning Confocal microscope. All micro-TENN confocal reconstructions were from full thickness z-stacks. For analysis of micro-TENNs post-transplant into the brain, micro-TENNs were fluorescently imaged using a NIKON® A1RSI Laser Scanning Confocal microscope. Each section was analyzed to assess the presence, architecture, and outgrowth/integration of micro-TENN neurons/neurites.

Statistical Analyses

No method was used to pre-determine the sample sizes of groups. Due to obvious visual differences between experimental groups, in most cases investigators were not blinded to treatment group during experiments or data assessment. For in vivo transplant studies, rats were randomly assigned for use in this experiment. The normality of all data was examined, and adjustments were made for non-normal data. An unpaired, parametric two-sided t-test was performed to determine if there were statistically significant differences in axonal outgrowth between uni-directional versus bi-directional micro-TENNs containing a dopaminergic end target. Unpaired, non-parametric, two sided Mann-Whitney tests were performed to determine if there were statistically significant differences in axonal outgrowth between the following treatment pairs: dissociated versus aggregated cells, high versus regular growth factor concentration, and uni-directional versus bi-directional micro-TENNs containing a striatal end target. An unpaired, nonparametric, two-sided Mann-Whitney test was performed to determine if there were statistically significant differences between the lengths of TH+ axons as a percentage of total axonal length with collagen I versus collagen I-laminin cocktail inner cores. ANOVA was performed for the extracellular matrix studies. When differences existed between groups, post-hoc Tukey's pair-wise comparisons were performed. For all statistical tests, $p<0.05$ was required for significance. Data are presented as mean±standard deviation.

Cortical Neuron Isolation and Culture

Neural cell isolation and culture protocols are similar to that of published work. Briefly, timed-pregnant rats were euthanized, and the uterus removed. Embryonic day 18 fetuses were transferred from the uterus to cold HBSS, wherein the brains were extracted and the cerebral cortical hemispheres isolated under a stereoscope via microdissection. Cortical tissue was dissociated in 0.25% trypsin+1 mM EDTA at 37° C., after which the trypsin/EDTA was removed and replaced with 0.15 mg/ml DNase in HBSS. Dissociated tissue+DNase was centrifuged for 3 min at 3000 RPM before the DNase was removed and the cells re-suspended in neuronal culture media, composed of NEUROBASAL®+B27®+Glutamax™ (ThermoFisher) and 1% penicillin-streptomycin.

Micro-TENN/Living Electrode Fabrication

Figure 29D:
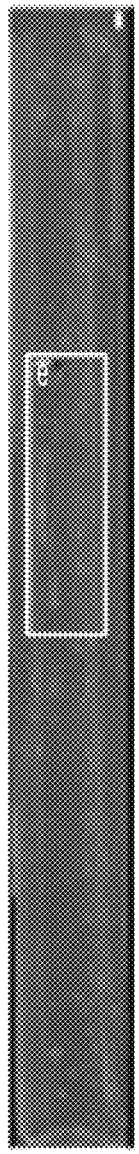
Figure 29E:
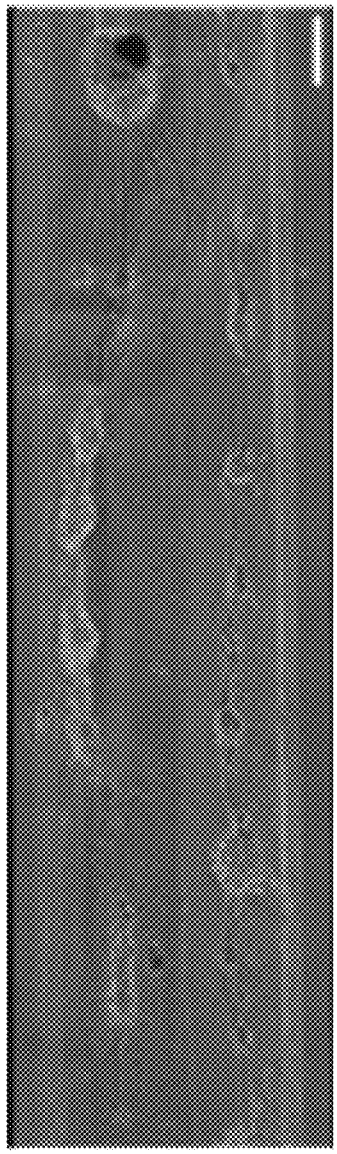

Micro-TENNs were constructed in a three-phase process (FIG. 29A-FIG. 29H). First, agarose micro-columns of a specified geometry (outer diameter (OD), inner diameter (ID), and length) were formed in a custom designed acrylic mold (FIG. 29A). The mold is an array of cylindrical channels that allow for the insertion of acupuncture needles (Seirin, Weymouth, Mass.) such that the needles are concentrically aligned within the channels. Molten agarose in Dulbecco's phosphate buffered saline (DPBS) was poured into the mold-needle assembly and allowed to cool (agarose: 3% weight/volume). Once the agarose solidified, the needles were removed and the mold disassembled, yielding hollow agarose micro-columns with a specific outer diameter equal to the size of the channels and inner diameter equal to the outer diameter of the needles. Micro-columns were sterilized via UV light for 30 min and stored in DPBS to prevent dehydration until needed. For these studies, the mold channels were 398 μm in diameter and the acupuncture needles were 180 resulting in micro-columns with a 398 μm OD and a 180 μm ID. Micro-columns were cut to either two or five millimeters in length. Next, primary cortical neurons were forced into cell aggregates (FIG. 29B). These aggregates provide the necessary architecture for the growth of long axonal fascicles spanning the length of the microcolumn. Cells were transferred to an array of inverted pyramidal wells made in PDMS (SYLGARD® 184, Dow Corning) cast from a custom-designed, 3D printed mold (FIG. 29B). Dissociated cortical neurons were suspended at a density of 1.0-2.0 million cells/ml and centrifuged in the wells at 200 g for 5 min. This centrifugation resulted in forced aggregation of neurons (or any other cell type) with precise control of the number of neurons per aggregate/sphere (12 μL cell suspension per well). Pyramidal wells and forced aggregation protocols were adapted from Ungrin et al. Finally, micro-columns were removed from DPBS and excess DPBS removed from the micro-column interior via micropipette. Micro-columns were then filled with extracellular matrix (ECM) comprised of 1.0 mg/ml rat tail collagen+1.0 mg/ml mouse laminin (Reagent Proteins, San Diego, Calif.) (FIG. 29C). Unidirectional or bidirectional micro-TENNs were seeded by carefully placing an aggregate at one or both ends of the micro-columns, respectively, using fine forceps under a stereoscope and were allowed to adhere for 45 min at 37° C., 5% CO2. To create dissociated micro-TENNs, dissociated cortical neurons were transferred via micropipette into the ECM-filled micro-column as detailed in prior work. Micro-TENNs were then allowed to grow in neuronal culture media with fresh media replacements every 2 days in vitro (DIV).

Growth Characterization

Phase-contrast microscopy images of micro-TENNs in culture were taken at 1, 3, 5, 8, and 10 DIV at 10× magnification using a NIKON® Eclipse Ti-S microscope, paired with a QIClick® camera and NIS Elements BR 4.13.00. Micro-TENNs were fabricated and classified into one of four groups: dissociated/2 mm long ($LE_{DISS,2mm}$) (n=7), unidirectional aggregate/2 mm long ($LE_{UNI,2mm}$) (n=6), bidirectional aggregate/2 mm long ($LE_{BI,2mm}$) (n=9), or bidirectional aggregate/5 mm long ($LE_{BI,5mm}$) (n=7). Growth rates for each group at specific timepoints were quantified as the change in the length of the longest identifiable neurite divided by the number of days between the current and preceding timepoint. The longest neurites were manually identified within each phase image using functions from the Image Processing Toolbox in MATLAB (MathWorks, MA), and length was measured from the source aggregate to the neurite tip. The same starting micro-TENNs and starting points were used across timepoints for more accurate analysis. Mean growth rates were found for each group at the specified timepoints and compared with two-way analysis of variance (ANOVA), with post-hoc analysis performed where necessary with the Bonferroni procedure ($p<0.05$ required for significance). All data presented as mean±s.e.m. To identify aggregate-specific growth across the micro-columns, cortical neuronal aggregates were labeled with either green fluorescent protein (GFP) or the red fluorescent protein mCherry via adenoassociated virus 1 (AAV1) transduction (Penn Vector Core, Philadelphia, Pa.). Briefly, after centrifuging aggregates in the pyramid wells, 1 μL of AAV1 packaged with the human Synapsin-1 promoter was added to the aggregate wells (final concentration: ~3×109 viral copies per aggregate). Aggregates were incubated at 37° C., 5% CO2 overnight before the media was replaced twice, after which transduced aggregates were plated in micro-columns as described above, each with one GFP+ and one mCherry+ aggregate (n=4 total). Over multiple DIV, images of the micro-TENNs were taken on a NIKON® A1RSI Laser Scanning confocal microscope paired with NIS-Elements® AR 4.50.00 software. Sequential slices of 10-20 μm in the z-plane were acquired for each fluorescent channel. All confocal images presented are maximum intensity projections of the confocal z-slices.

Viability Assessment

To assess neuronal viability, 5-mm long unidirectional ($LE_{UNI}$) and bidirectional ($LE_{BI}$) constructs and age-matched planar cultures plated on polystyrene were stained with a calcein-AM/ethidium homodimer-1 (EthD-1) assay (ThermoFisher) at 10 and 28 DIV. Metabolically active cells convert the membrane-permeable calcein AM to calcein, which fluoresces green ($\lambda_{exc}$~495 nm; $\lambda_{em}$~515 nm), while EthD-1 enters membrane-compromised cells and fluoresces red upon binding to nucleic acids ($\lambda_{exc}$~495 nm; $\lambda_{em}$~635 nm). Briefly, cultures were gently rinsed in DPBS. A solution of calcein-AM (1:2000 dilution; final concentration ~2 µM) and ethidium homodimer-1 (1:500; ~4 µM) in DPBS was added to each culture, followed by incubation at 37° C., 5% $CO_2$ for 30 min. Following incubation, cultures were rinsed twice in fresh DPBS and imaged at 10× magnification on a Nikon® A1RSI Laser Scanning confocal microscope paired with NIS-Elements® AR 4.50.00 software. Viability was quantified as the ratio of the total area of calcein-AM-positive cells to the total area of both calcein-AM-positive and ethidium homodimer-positive cells using ImageJ (National Institutes of Health, MD). Sample sizes for each group were as follows: $LE_{UNI,5mm}$ (n=4, 4); $LE_{BI,5mm}$ (n=7, 4); planar cultures (n=9, 5) for 10 and 28 DIV, respectively. All data presented as mean±s.e.m.

Live Calcium Imaging

As proof-of-concept for investigating micro-TENN aggregate connectivity, aggregates were transduced with the genetically encoded calcium reporters GCaMP6f or RCaMP1b (Penn Vector Core, Philadelphia, Pa.). After centrifuging aggregates in the pyramid wells, 1 µL of AAV1 packaged with the human Synapsin-1 promoter was added to the aggregate wells (final concentration: ~3×10⁹ viral copies per aggregate). Aggregates were incubated at 37° C., 5% $CO_2$ overnight before the media was replaced twice, after which transduced aggregates were plated in micro-columns as described above. Micro-TENNs were imaged after 7-10 DIV using a NIKON® Eclipse Ti® microscope paired with an ANDOR Neo/Zyla Camera® and Nikon® Elements AR 4.50.00, after which calcium transients from the recordings were identified in NIKON® Instruments® Elements AR 4.50.00. The intensities of selected regions of interest (ROIs) of the micro-TENNs were plotted over time relative to background (defined as ROIs without cell bodies or axons).

Functional Analysis

Fluorescent calcium recordings were collected as described above to generate .tiff stacks of micro-TENN activity. Each .tiff stack was composed of 120 seconds of activity recorded at 20 frames per second (2400 total frames). Functional analyses were performed using three MATLAB® software toolboxes—FluoroSNNAP, MATLAB® software Statistics Toolbox, and SIFT for EEGLAB. FluoroSNNAP is an interactive software package designed by Meaney et al. to perform calcium imaging-based network analysis of neurons in vitro. Briefly, a time-averaged image was generated from the .tiff stack, after which ROIs measuring approximately 20 µm in diameter were manually selected. Using FluoroSNNAP, intensities of the ROIs were extracted and normalized to assess functional connectivity patterns within bidirectional micro-TENNs; specifically, normalized Pearson cross-correlation and normalized phase synchronization matrices were created from the calcium transient patterns of the ROIs. Additionally, to assess information flow across the micro-TENN, the SIFT toolbox was used to fit a multivariate autoregressive (MVAR) model, which in turn was used to generate normalized Direct Transfer Function (nDTF) connectivity matrices. The nDTF has been used in literature to determine direction and frequency content of EEG activity 19, 20. Here, it was applied to detect information flow from one aggregate to the other in bidirectional micro-TENNs. The nDTF estimates were obtained using a numerically stable, 10th order MVAR model with an 80-second sliding window and a 40-second time step. nDTF coefficients were obtained over 1-9 Hz due to the Nyquist limit.

Immunocytochemistry

Micro-TENNs were fixed in 4% formaldehyde for 35 min at 4, 10, and 28 DIV. Micro-TENNs were then rinsed in 1×PBS and permeabilized with 0.3% Triton X100+4% horse serum in PBS for 60 min before being incubated with primary antibodies overnight at 4° C. Primary antibodies were Tuj-1/beta-III tubulin (T8578, 1:500, Sigma-Aldrich) to label axons and synapsin-1 (A6448, 1:500, Invitrogen) to label presynaptic specializations. Following primary antibody incubation, micro-TENNs were rinsed in PBS and incubated with fluorescently-labeled secondary antibodies (1:500; sourced from Life Technologies, Invitrogen, and Jackson ImmunoResearch) for 2 h at 18°-24° C. Finally, Hoechst (33342, 1:10,000, ThermoFisher) was added for 10 min at 18°-24° C. before rinsing in PBS. Micro-TENNs were imaged on a NIKON® A1RSI Laser Scanning confocal microscope paired with NIS Elements AR 4.50.00. Sequential slices of 10-20 µm in the z-plane were acquired for each fluorescent channel. All confocal images presented are maximum intensity projections of the confocal z-slices.

Cerebral Cortical and Corticothalamic Implantation

As proof-of-concept for micro-TENN behavior in vivo, preformed micro-TENNs with GFP+ neurons/axons were delivered into the brain via stereotaxic microinjection similar to descriptions in prior work 12, 13. Male Sprague-Dawley rats weighing 325-350 grams were anesthetized with isoflurane at 1.0-2.0 liters per minute (induction: 5.0%, maintenance: 1-5-2.0%) and mounted in a stereotactic frame. Meloxicam (2.0 mg/kg) and bupivacaine (2.0 mg/kg) were given subcutaneously at the base of the neck and along the incision line, respectively. The area was shaved and cleaned with betadine solution, after which a small craniotomy over the sensory cortex was made (coordinates: +4.8 mm AP, ±2.3 mm ML). Bidirectional micro-TENNs (5 mm in length) were loaded into a needle coupled to a Hamilton syringe, mounted onto a stereotactic arm for precise placement. To deliver the construct into the brain without forcible expulsion, the needle was slowly inserted into the cortex to a depth of 6 mm. The plunger of the Hamilton syringe was then immobilized, while the needle containing the micro-TENN was manually raised 5 mm at approximately 1.5 mm/minute. This process allows for the low-force delivery of micro-TENNs to connect the whisker barrel cortex with the ventral posteromedial nucleus (VPM), a deeper thalamic structure.

Tissue Harvest and Histology

At 7 and 28 days post-implant, rats were euthanized and perfused with cold heparinized saline and 10% formalin. After post-fixation of the head overnight, the brain was harvested to assess micro-TENN survival and host/micro-TENN synaptic integration. Briefly, brains were sagittally blocked and cut in 40 µm slices for cryosectioning. For frozen sections, slices were air-dried for 30 minutes, twice-treated with ethanol for three minutes, and rehydrated in PBS twice for three minutes. Sections were blocked with 5% normal horse serum (ABC Universal Kit, Vector Labs, cat #PK-6200) in 0.1% Triton-x/PBS for 30-45 minutes. Primary antibodies were applied to the sections in 2% normal horse serum/Optimax buffer for two hours at room temperature. Primary antibodies were goat anti-GFAP (1:1000), rabbit anti-IBA1 (1:1000), chicken anti-MAP2 (1:1000), and mouse anti-Tuj1 (1:1000). Sections were rinsed with PBS three times for five minutes, after which secondary antibodies (1:1000) were applied in 2% normal horse serum/PBS for one hour at room temperature. Sections were counterstained with DNA-specific fluorescent Hoechst 33342 for ten minutes and then rinsed with PBS. After immunostaining, slides were mounted on glass coverslips with Fluoromount-G mounting media.

Micro-TENN In Vitro Development

Figure 4A:
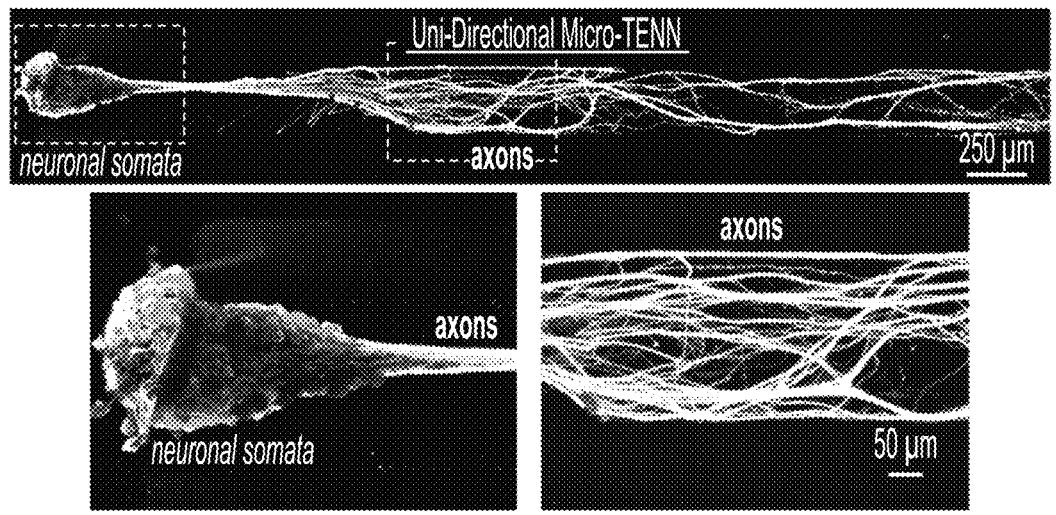
FIGS. 4A-4C illustrate micro-TENN structure and functional analysis. Micro-TENNs consist of tight clusters of neuronal somata with dense axonal tracts extending across in the central column.
Figure 4B:
Figure 4C:
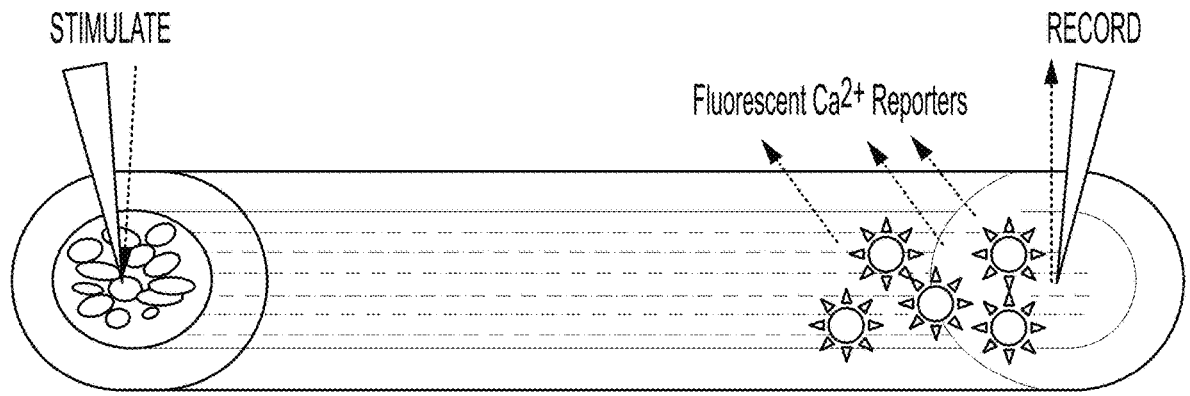

Hydrogel micro-columns were optimized in vitro to support neuronal survival and directed axon growth. Micro-columns were 5-30 mm in length, and consisted of hollow agarose tubes (350-500 µm outer diameter) to direct axonal outgrowth through a central extracellular matrix (ECM; 150-400 µm inner diameter). Dissociated neurons were delivered into the proteinaceous matrix at one or both ends of the micro-columns, and cultured for 7-42 days in vitro (DIV) based on the desired length of axonal outgrowth (FIG. 4A-FIG. 4C). Using electrical stimulation and $Ca^{2+}$-sensitive dyes in bidirectional micro-TENNs, the ability to stimulate one population of neurons and have the resulting action potentials travel across the axonal region to the other population was demonstrated. Micro-TENNs have been generated using multiple neuronal subtypes, including primary cerebral cortical neurons, dopaminergic neurons, and dorsal root ganglion neurons (FIG. 5A-FIG. 5E).

Figure 6:
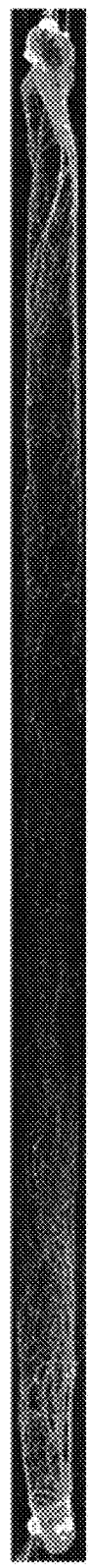
FIG. 6 illustrates an extra-long micro-TENN. In vitro immunohistochemistry of a bidirectional micro-TENN demonstrated robust axonal outgrowth across the neuron populations. Neuronal cell body and axonal staining show axon outgrowth up to 2 cm.
Figure 7A:
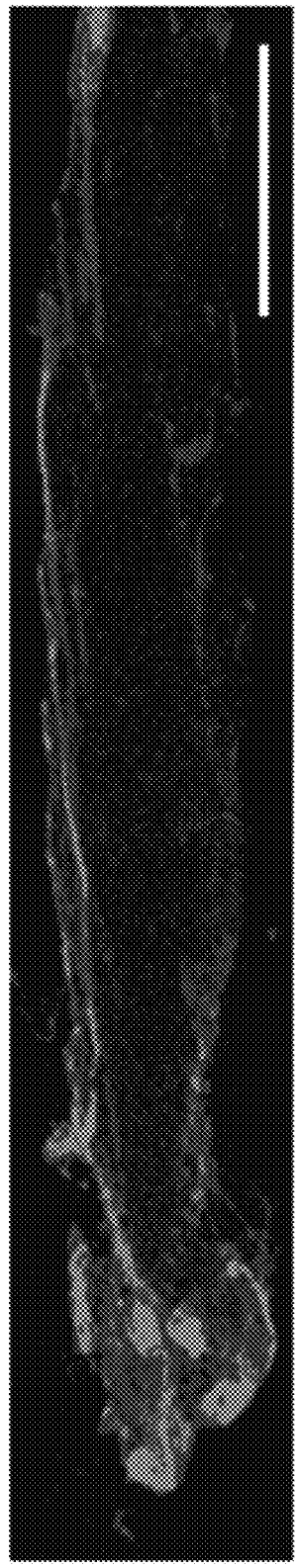
FIGS. 7A-7D illustrate micro-TENN survival, ingrowth and integration in vivo.
Figure 7B:
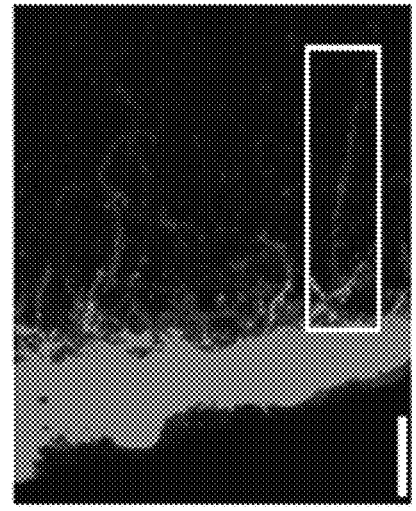
Figure 7C:
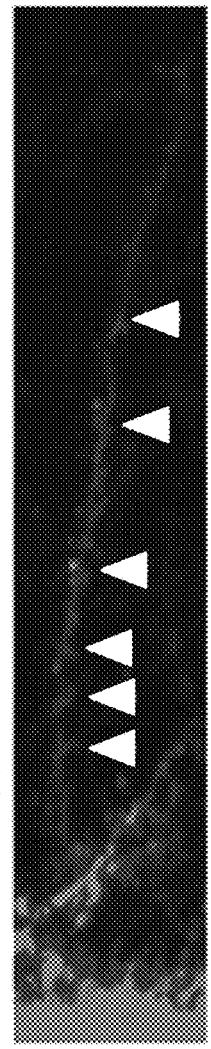
Figure 7D:
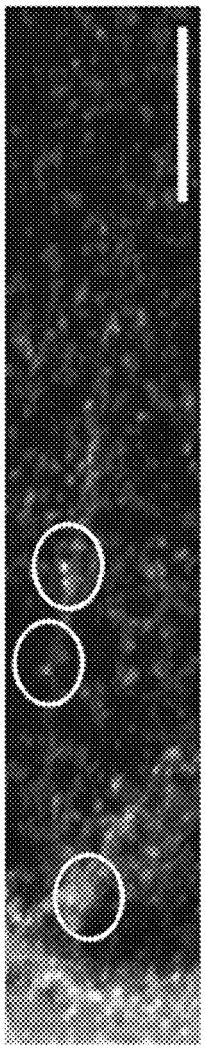

Long micro-TENNs with axon fascicles (~1 cm by 14 DIV and over 2 cm by 28 DIV) were also created as depicted in FIG. 6. Additionally, smaller micro-TENNs spanning on the order of hundreds of microns to millimeters were created as depicted in FIG. 5A-FIG. 5E. These were more appropriately scaled for one of the current application of living electrodes to penetrate Layer IV or V in the rat cortex.

FIG. 17A-FIG. 17D provide views of immunolabeled long-projecting unidirectional axonal-based living electrodes. These axon-based living electrode constructs are on the order of several hundred microns in diameters—similar to the diameter of a human hair—yet may extend at least on the order of centimeters to reach deep layers/nuclei in the brain with a relatively small microinjection footprint.

Micro-TENN In Vivo Delivery and Survival

Micro-TENNs were delivered into the brain via stereotaxic microinjection to provide a bridge of living axons to reconnect discrete anatomical regions. For in vivo delivery, the hydrogel casing provided structural support to protect the micro-tissue during transportation and transplantation. Moreover, the small size permits minimally invasive implantation into delicate regions of the nervous system. Micro-TENNs at the desired length were drawn into a needle, slowly inserted into the cortex, and expelled using a plunger. Micro-TENNs were stereotaxically injected to connect thalamic structures with the barrel fields of the cortex to assess construct survival and integration.

At 3, 7, and 28 days post-implant, immunohistochemistry and fluorescent microscopy revealed surviving neurons in the micro-TENN interior, which maintained a tight cluster with axonal fascicles extending parallel to the cortical-thalamic axis (FIG. 6). This demonstrated that micro-TENN neurons survived and maintained their axonal architecture. Additionally, micro-TENN neurons showed cortical integration as dendrites from the implanted neurons penetrated the cortex with structural evidence of synapse formation between micro-TENN neurons and hist neurons (FIG. 7A-FIG. 7D).

Recording/Stimulation Arrays

Living electrodes are used as a biological conduit to relay information to/from neurons deep within the brain to the surface of the brain. At the surface, arrays of devices are used to either record or stimulate the superficial end of the micro-TENN. These arrays could include electrical, optical, magnetic, chemical, acoustic, or other modality to create a specific and broad array that is capable of interfacing with the superficial end of the micro-TENN in a precise, temporal and spatial, manner. These arrays can be placed at the surface of the brain (subdural), above the dura (epidural), within the skull defect (intraosseous or periosseous), outside the skull under the gallea aponeurotica (subgaleal), or outside the skin (non-invasive on the scalp). These arrays can be linked to or integrated into microelectronics. They can include a battery for power, a radiofrequency and/or infrared induction coil, a light source, multiplex/demultiplex circuitry, a heat sink leveraging cerebrospinal flow or vascular beds, and/or embedded waveguides.

Method of Operation

Figure 8:
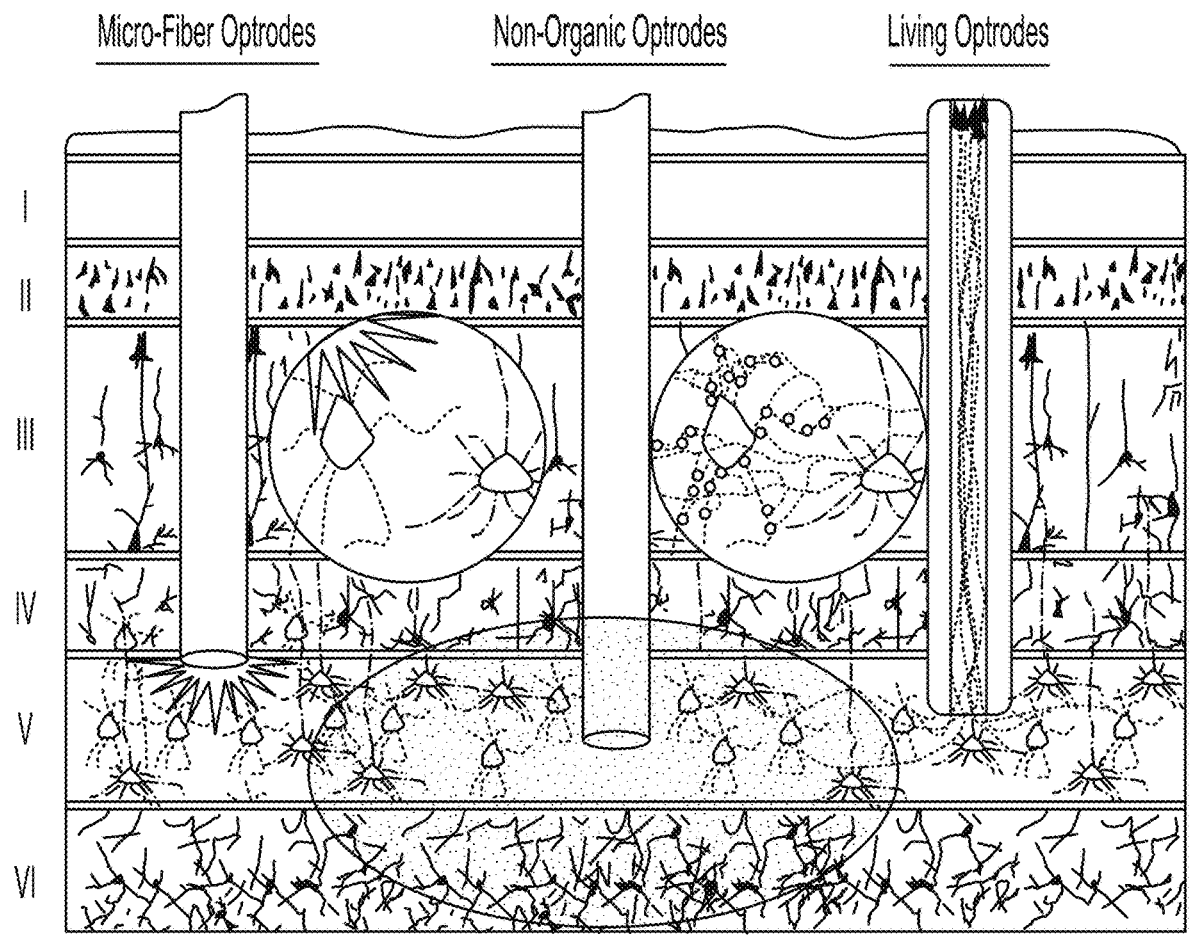
FIG. 8 describes theoretical advantages of axon-based "living electrodes" for neuromodulation: mechanisms and specificity of neuronal stimulation for "living electrodes" (left) versus conventional electrodes (center) and optrodes (right). Living electrodes provide engineered axonal tracts with a controlled cytoarchitecture and fully differentiated neurons that if pretransfected in vitro, constrain the spatial extent of transfected cells while the 3D attrition issues from delivery of cell suspensions, both advantages for clinical deployment. Living electrodes could offer high specificity, as the constructs can be designed to synapse with specific neuronal subtypes in a given anatomical region (as shown by living electrode axons synapsing with neurons of a certain color) as opposed to conventional electrodes that inherently stimulate or record from a relatively large 3D volume around the electrode (as shown by large aura of stimulation affecting many layers and neurons). While micro-fiber optrodes can achieve a high level of specificity, the in vivo delivery of opsins generally relies on injection of virus that may diffuse and affect non-target regions (spread of optogenetic transduction is illustrated by lightly shaded neurons straying from layer V into layer VI). Also, optical methods may have a limited benefit due to tissue absorption of light. Finally, living electrodes provide a soft pathway to route signals to/from deep brain structures compared to rigid materials used in electrodes/optrodes, thus minimizing signal issues due to mechanical mismatch/micromotion and glial scarring.

FIG. 8 describes advantages of living electrodes versus conventional electrodes and optrodes, highlighting the enhanced specificity due to synaptic integration of the living electrodes.

Preformed 3-D living electrodes provide at least two clinical deployment advantages: (1) spatial constraint of transfection agents and cells/axons via transduction in vitro and (2) avoidance of maturation/attrition issues from cell suspension.

The living electrode provides a soft pathway to route signals to/from deep brain structures versus rigid materials used in electrodes/optrodes, thus mitigating a chronic foreign body response, mechanical separation issues, and glial scarring.

Figure 9:
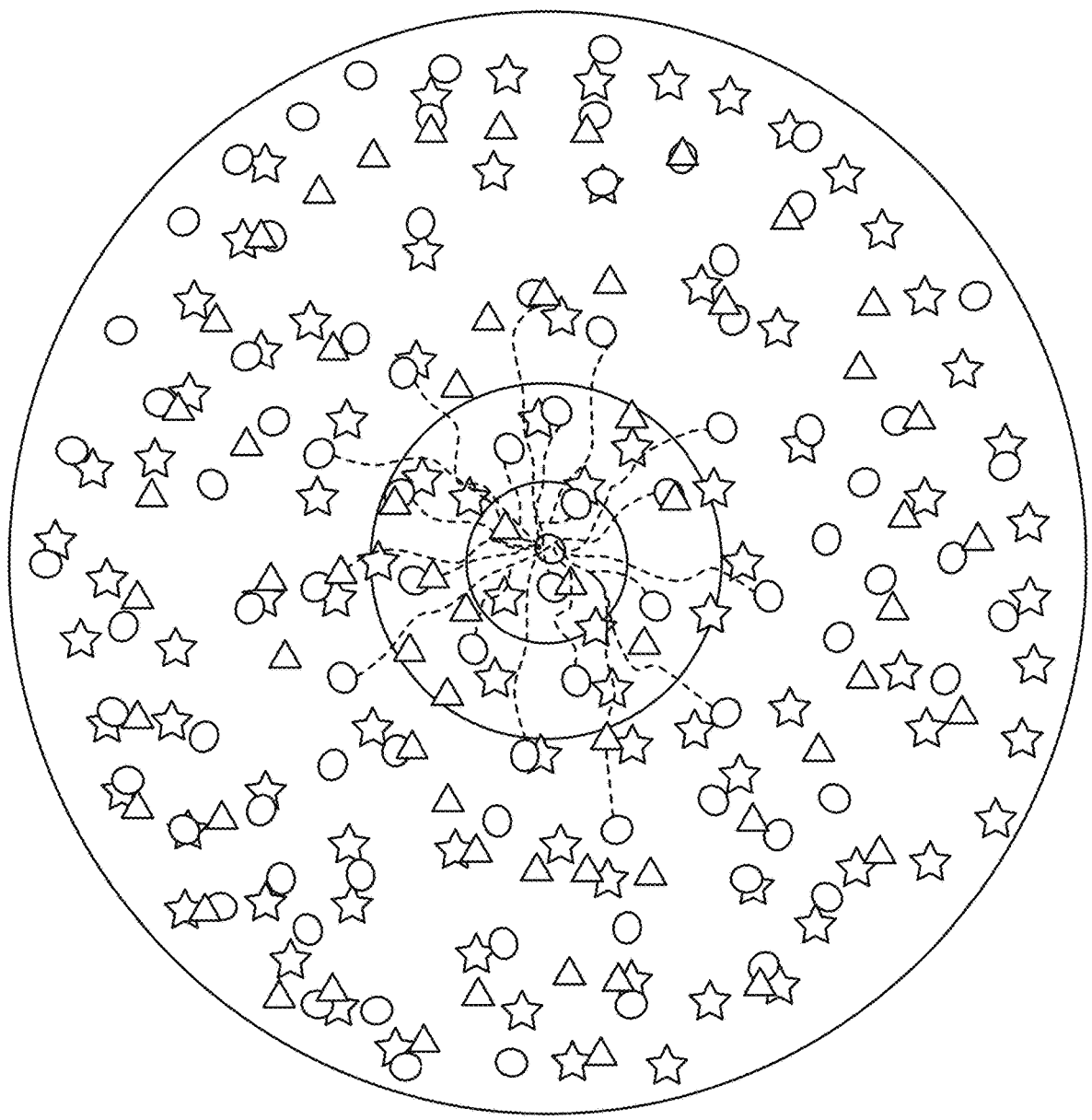
FIG. 9 describes the concepts of living electrode target specificity and synaptic integration. Living electrodes offer high specificity, as the constructs can be designed to synapse with specific neuronal subtypes, as demonstrated by micro-TENN axons synapsing with only circle neurons, not star neurons in the conceptual rendition.

While optrodes can achieve a high level of specificity, optical methods may have a limited extent due to tissue absorption. Electrodes inherently stimulate or record from a fixed volume around the electrode (red zone in FIG. 8). Spread of optogenetic transduction is illustrated by yellow neurons in multiple layers in FIG. 8). In contrast, living electrodes offer high specificity, as the constructs can be designed to synapse with specific neuronal subtypes, and thus may form many synapses with surrounding neurons (FIGS. 8 and 9).

Figure 10A:
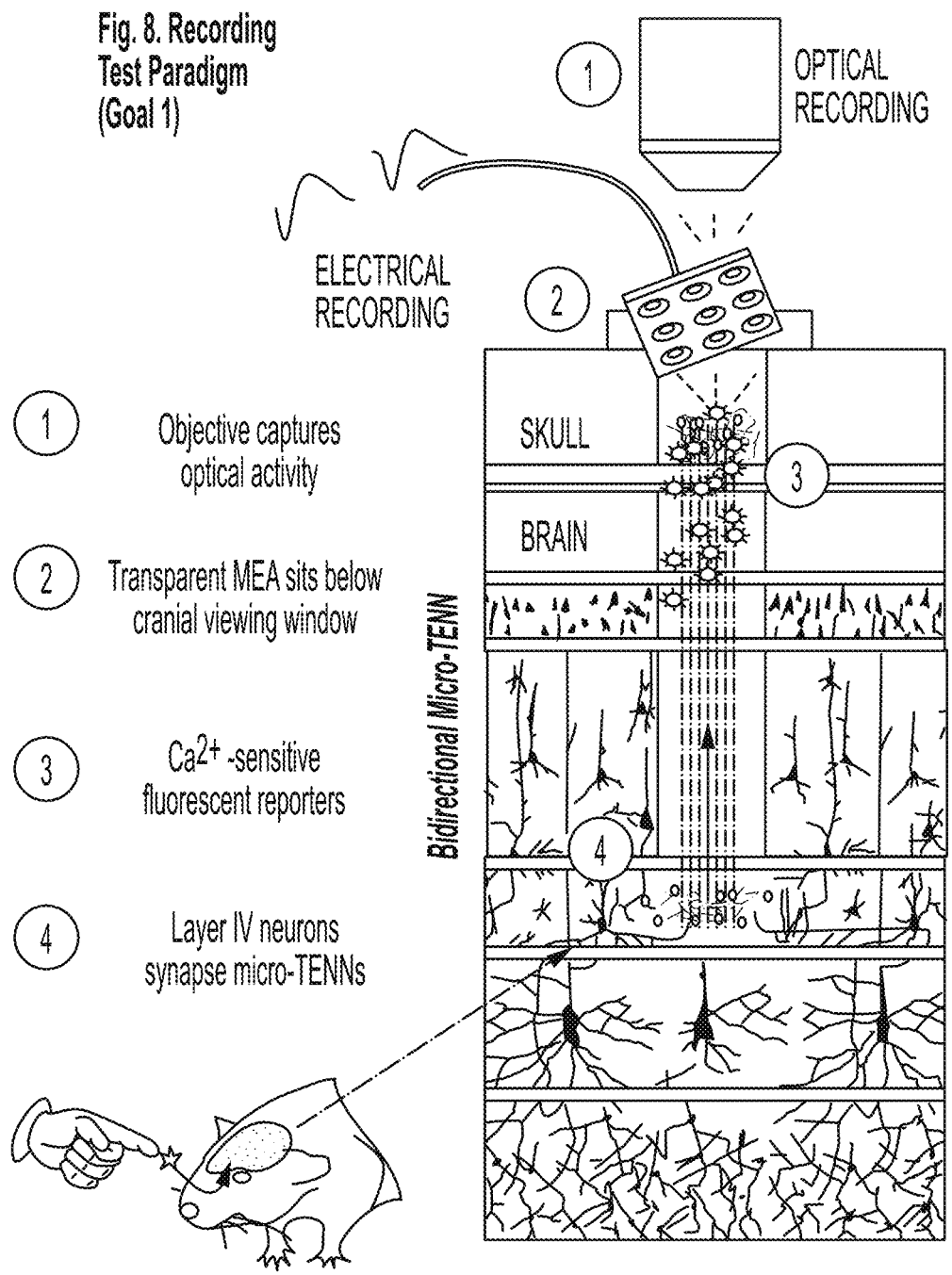
FIG. 10A-FIG. 10B illustrate recording and stimulation test paradigms for the use of living electrodes in the cerebral cortex.
Figure 10B:
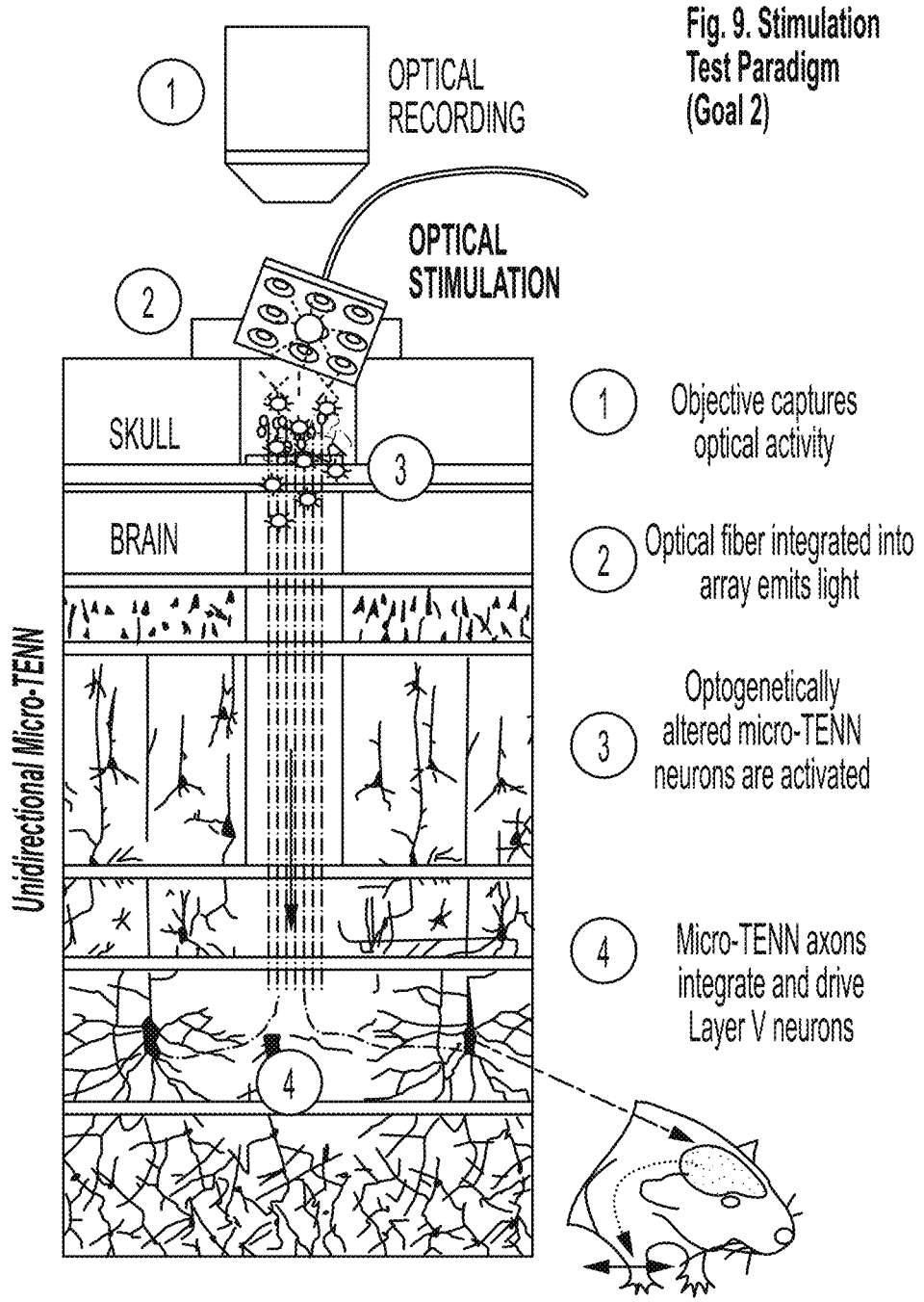
Figure 11:
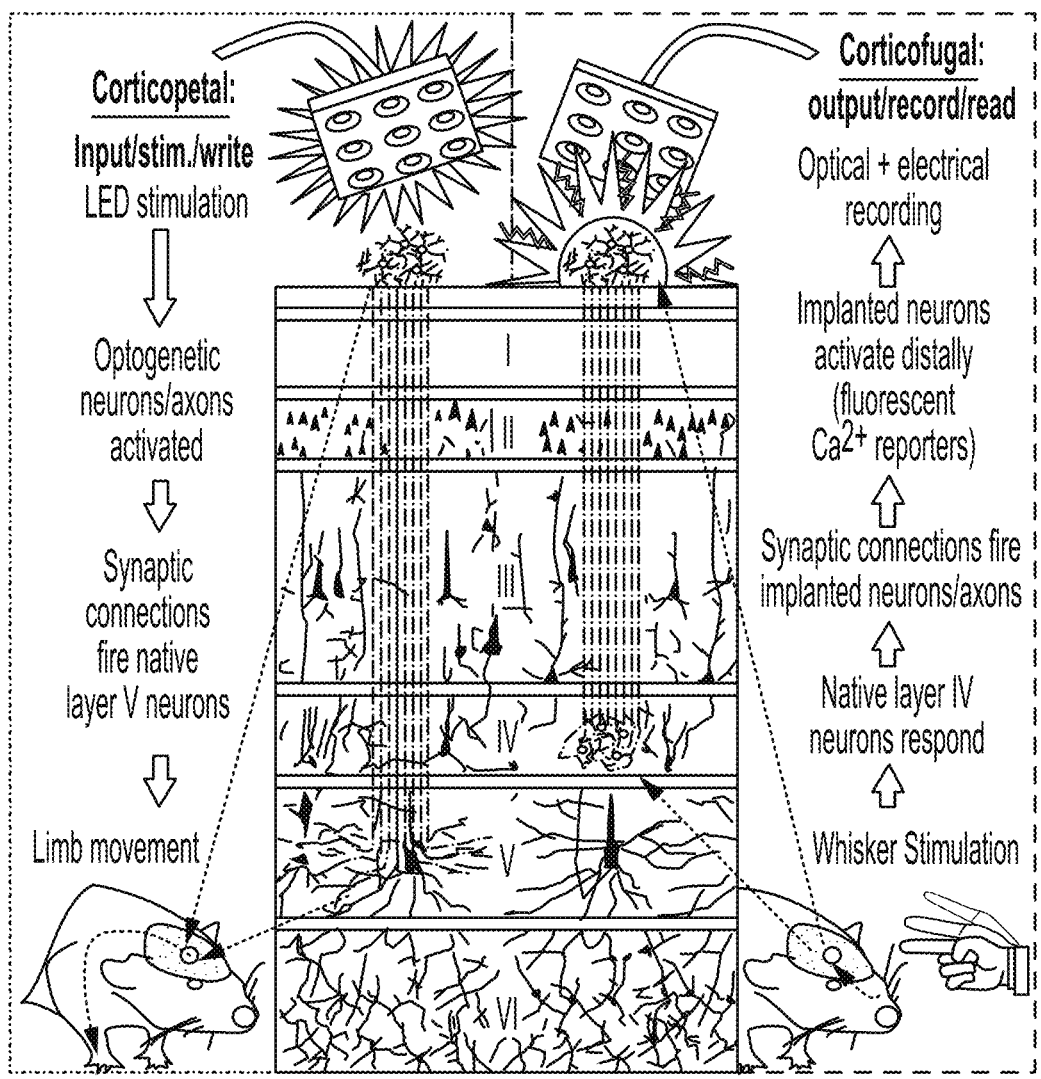
FIG. 11 illustrates the living electrode concept. Micro-TENNs are used for corticofugal recording (right panel) or corticopetal stimulation (left panel) interface with neural circuits. Micro-TENNs act as a living electrode by penetrating the brain to a prescribed location with the other end at the brain surface. Deep micro-TENN neurons/axons within the brain are then able to synaptically integrate with local host neurons while axonal projections spanning the construct serve as a functional relay to and from the cortical surface, where information is exchanged using optical and/or electrical interfaces. The output (corticofugal) paradigm enables projection of a facsimile of deep activity to the cortical surface via local synaptic integration. The input (corticopetal) paradigm permits controlled excitation or inhibition of specific neural circuitry.

FIGS. 10A, 10B, and 11 illustrate examples of the living electrode to be used for recording or stimulation paradigms in the rat cortex. The operation of the living electrode is not relegated to just the cortex, but can be employed anywhere in the brain where nonsuperficial signals need to be recorded or stimulated. Additionally, the input/stimulation version of the micro-TENN can be designed to interface with a specific type of neuron in order to selectively activate excitatory or inhibitory neurons. Although a rat is pictured here, the technology could be ultimately used in non-human primates and humans. A further iteration of the living electrode could include the usage of multiple neural types to achieve interaction with multiple neural subtypes. For example, one might want a living electrode that excites one neural population while inhibiting another population of neural cells (FIG. 1). As previously mentioned, the living electrode could also be developed to be a true bidirectional interface modality to enable closed loop interaction with the brain. This living electrode would be able to record, process, and then stimulate the brain, in controlled closed loop manner to provide refined and well-controlled stimulation of the nervous system to treat disease with a delicate hand instead of the brute force method using constant application of electrical stimulation currently.

Tissue Engineered Constructs for Neurosurgical Implantation

Figure 12:
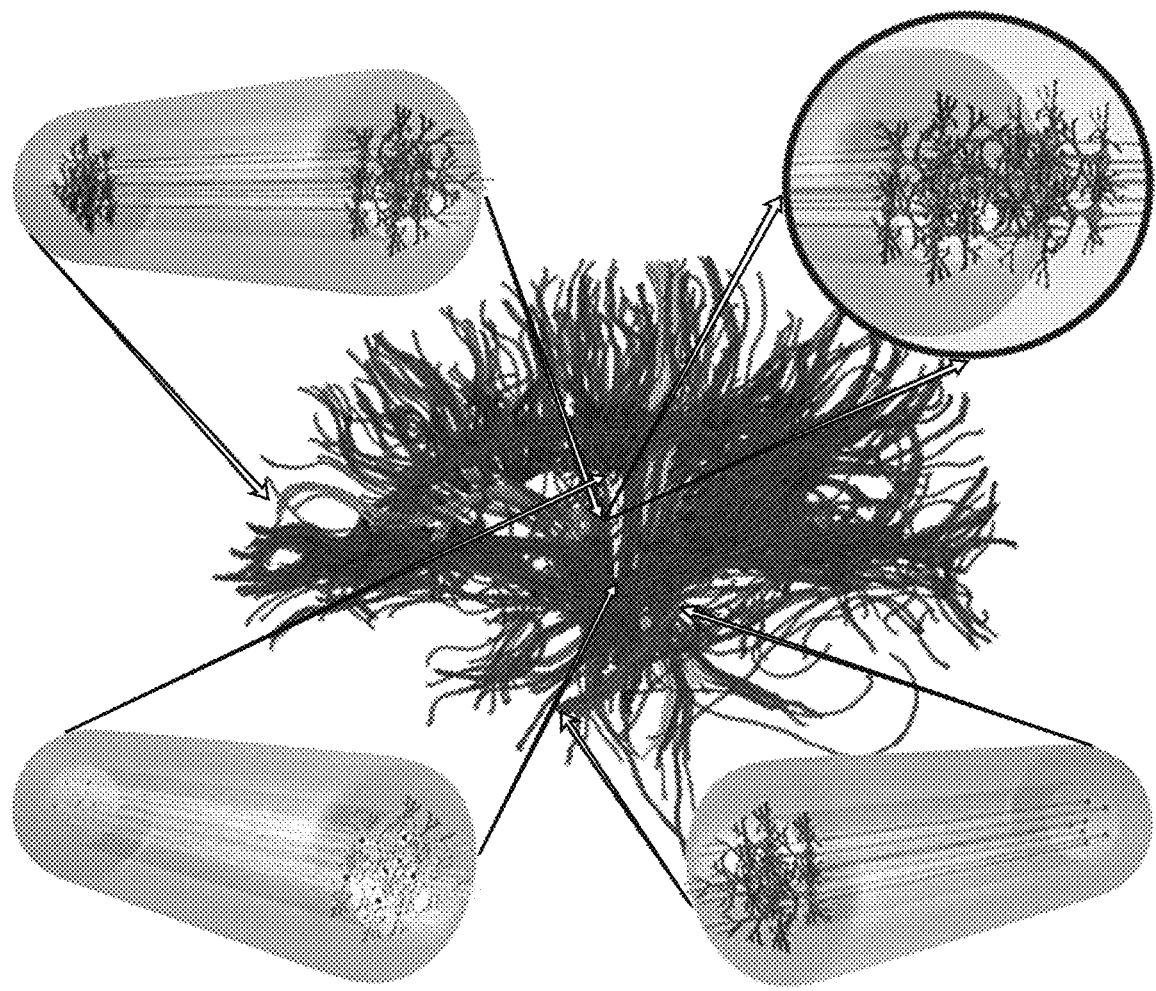
FIG. 12 depicts examples of living electrode structure and applications in the brain (purple: tractography of general axonal tracts in the brain). Micro-tissue engineered neural networks (TENNs), initially developed to physically reconstruct lost long-distance axonal connections in the brain, are miniature preformed constructs grown in vitro that consist of discrete neuronal population(s) spanned by long axonal tracts. Micro-TENNs may consist of uni- or bidirectional axonal tracts. Cortical-thalamic micro-TENNs can be applied as living electrodes to record or modulate sensory-motor information in the cortex or thalamus, vulnerable in brain trauma and stroke. Dopaminergic (DA) micro-TENNs can be used to provide/restore dopaminergic inputs to the striatum, important to mitigate motor symptom in Parkinson's disease. Cortical-hippocampal micro-TENNs can be used to modulate or encode information exchange between the cortex and hippocampus, which is crucial for learning and memory formation.
Figure 13:
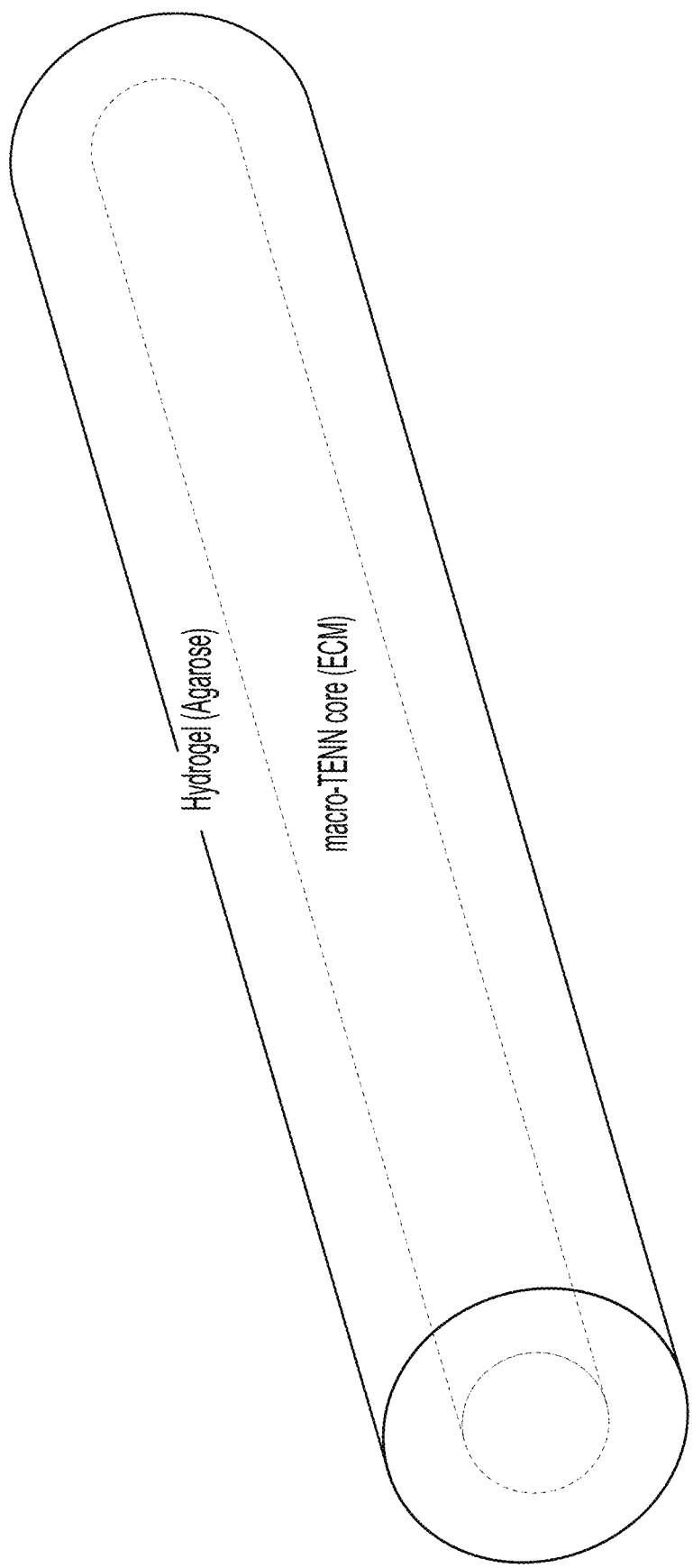
FIG. 13 provides a perspective view of a macro-TENN electrode according to an embodiment of the invention.

As shown in FIG. 12, living electrodes can be implanted and interface with the brain to record or stimulate neurons for the treatment or as a diagnostic of a particular function or dysfunction of the nervous system (i.e., Parkinson's disease, obesity, inflammation, migraine, diabetes, epilepsy, etc.). For example, in a patient with Parkinson's disease dopaminergic living electrodes restore dopamine inputs to deep brain structures (e.g. striatum) with brain surface control of activation. For patients with epilepsy GABAergic living electrodes could be used to inhibit seizure foci, with activation upon detection of early epileptiform activity (e.g., inhibitory living electrodes can precisely deliver copious GABA directly to foci at the earliest sign of pre-seizure neural activity).

Implanted living electrodes can also record or stimulate neurons for the precise and selective interface between biological and non-biological entities for the restoration or augmentation of function in persons with or without locked-in syndrome to affect action via thought or for input of sensory information. For example, motor control (reading activity of neurons in the motor cortex or motor output hub in the brain or spinal cord) for device (e.g., robotic hand/arm) actuation can be monitored. Sensory feedback (inputting information to the sensory cortex or a sensory processing hub in the brain) for feel and/or proprioception of external device (e.g., robotic hand/arm) can also be recorded.

Living electrodes can also be implanted and interface with the brain to use the activation as a method to enhance regrowth or improvement of function. For example, implantable living electrodes can control local neural activity to facilitate/elicit endogenous regeneration. In another example, living electrodes can control local neural activity to enhance healthy network function and/or attenuate/block deleterious network function (e.g. rectify issues with circuit timing).

Confocal Reconstruction of Macro-TENN In Vitro: Proof of Concept

Figure 14A:
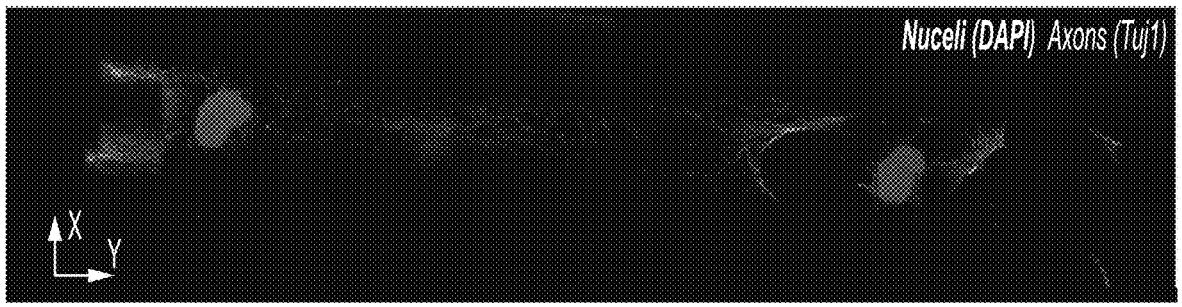
FIG. 14A-FIG. 14E depict neural growth within a macro-TENN structure according to embodiments of the invention. Cell nuclei are stained blue with DAPI. Axons are stained green with beta-tubulin-III (Tuj1).
Figure 14B:
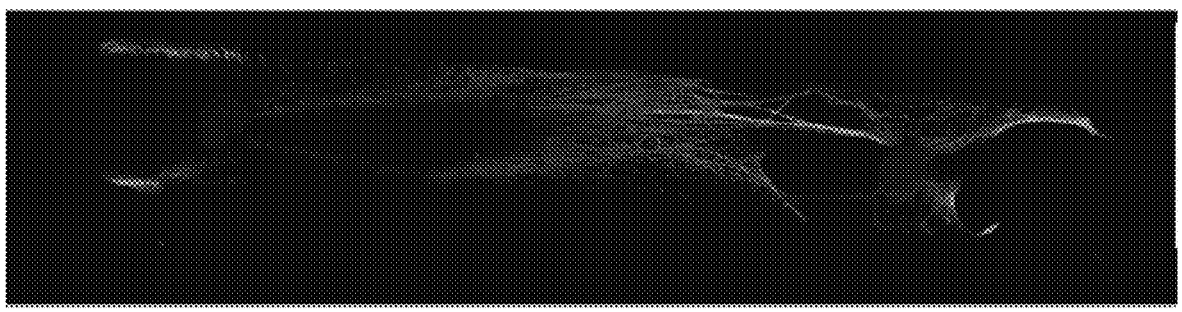
Figure 14C:
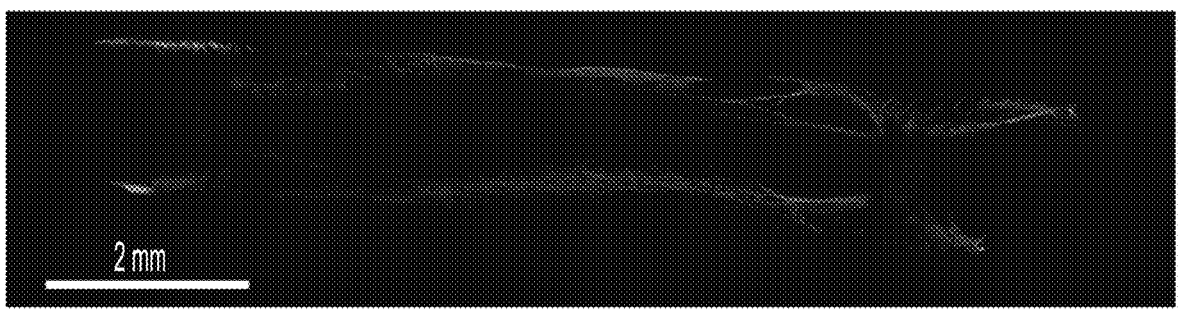
Figure 14D:
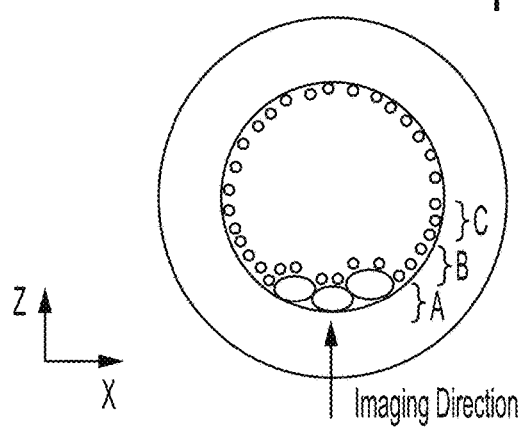
Figure 14E:
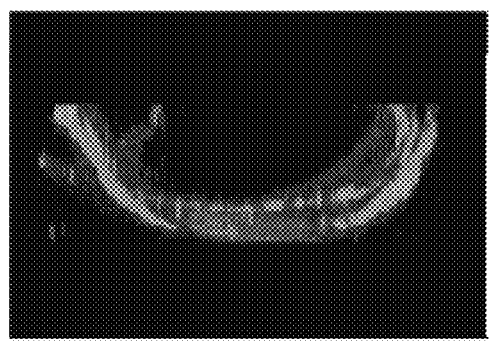

Applicant grew primary dorsal root ganglia neurons in macro-TENN constructs over 7 days in vitro (DIV). Following this period, the cells were fixed and immunolabelled with markers for cell nuclei (DAPI) and their axons (beta-tubulin-III/Tuj-1). The constructs were then imaged on a confocal microscope. The images were reconstructed and stitched to provide a detailed overview of the construct in all planes (FIG. 14A-FIG. 14E). What the images showed are best represented by the cartoon in FIG. 14D, which represents the reconstruction pictured in FIG. 14E looking in they direction of the construct (i.e., looking down the length of the construct). FIG. 14D and FIG. 14E depict that the axons are only growing along the inner surface of the tube and not in the extracellular matrix that fills the core of the construct. In smaller constructs, the axons grow through the entire cross-section of the construct, not just the interface as seen here. Looking from above the construct, FIG. 14A-FIG. 14C show sequential slices of the confocal image, starting from bottommost (FIG. 14A) to topmost (FIG. 14C). In FIG. 14C, the axons are only growing along the sidewalls, while in FIG. 14B at the bottom of the construct, the axons are spread out along the entire surface of the bottom.

Proposed Device in PNS

Based on the findings showing axonal regrowth only at the interior face of the macro-TENN, Applicant proposes to create a regenerative electrode as depicted in FIGS. 15A-15C. The deployment of this device would allow for the growth of axons through an unimpeded channel (contrary to sieve electrodes). The channel could be the same size of the nerve or larger to provide further spreading and defasciculization of a particular nerve and its fascicles. Electrodes could be placed along the periphery and along the length of the construct to allow for selective stimulation and recording (FIGS. 15A and 15B). If the construct were to be sized larger than the nerve, the construct could taper at the proximal and distal ends to enable suturing and attachment to the nerve of choice (FIG. 15C). A larger cross sectional area advantageously allows the axons/fascicles to spread out further, thereby providing more selectivity. Embodiments of the invention provide superior conformation to the interior of the side wall of the tube. Without being bound by theory, Applicant believes that the conformation is superior because of a greater surface area due to use of the interior of the tube versus midplane technology. Again, without being bound by theory, Applicant believes that the greater surface area would allow for greater separation of axons/fascicles and therefore greater selectivity.

Further Micro-TENN Fabrication Techniques

Further embodiments of the invention provide novel micro-tissue engineering methodology to more consistently create micro-TENNs of the desired architecture consisting of discrete neuronal population(s) spanned by pure axonal tracts. In particular, embodiments of the invention utilize "forced cell aggregation" within custom-build pyramidal micro-wells to create "aggregates" or "spheres" of neurons with precise control of the number of neurons—and hence diameter—per aggregate/sphere as depicted in FIG. 16C-FIG. 16E. To accomplish this, dissociated neurons were transferred to a chamber containing an array of inverted pyramid micro-wells made in PDMS (SYLGUARD® 184, Dow Corning) cast from a custom-designed 3D-printed mold. The wells were then centrifuged at 200 g for 5 min. This centrifugation resulted in forced aggregation of neurons (or any other cell type if desired) with precise control of the number of neurons per aggregate/sphere based on the density of neurons used and the volume added to each well. 12 μL of neuronal suspension per well at a density of 1-2 million cells/mL was suitable to create aggregate/spheres of appropriate diameter to fit within micro-columns. The aggregates/spheres were then carefully placed within one or both ends of the micro-columns and allowed to adhere for 45 min at 37° C., 5% $CO_2$. Seeded micro-columns were then allowed to grow in neuronal growth media consisting of NEUROBASAL® Media, GLUTAMAX™ media, and B-27® media (ThermoFisher™) over at least several days in vitro to form micro-TENNs (as described in Laura A. Struzyna et al., "Rebuilding Brain Circuitry with Living Micro-Tissue Engineered Neural Networks", 21(21-22): 2744-2756 *Tissue Engineering Part A* (2015) and J. P. Harris et al., "Advanced biomaterial strategies to transplant preformed micro-tissue engineered neural networks into the brain," 13(1) *J. Neural Eng.* 016019 (2016). This methodology resulted in the formation of uni- or bi-directional micro-TENNs with defined neuronal somatic regions and axonal extension of several millimeters over a few days in vitro (FIG. 17A-FIG. 17D). Notably, this methodology consistently produces the ideal micro-TENN cytoarchitecture consisting of a defined zone with neuronal somata as aggregates at one or both ends of the micro-column and a defined zone with axonal projections running longitudinally to span the central portion of the micro-column (FIG. 17A-FIG. 17D). This ideal distribution was further verified by immunocytochemistry and confocal microscopy to label these aggregate micro-TENNs using antibodies recognizing all axons (beta-tubulin III) and all cell nuclei (Hoechst), and the hydrogel comprising the micro-column is non-specifically labeled. Also, this micro-TENN was labeled for a synaptic marker (synapsin), suggesting functional maturation and electrochemical activity in the micro-TENNs.

Figure 18:
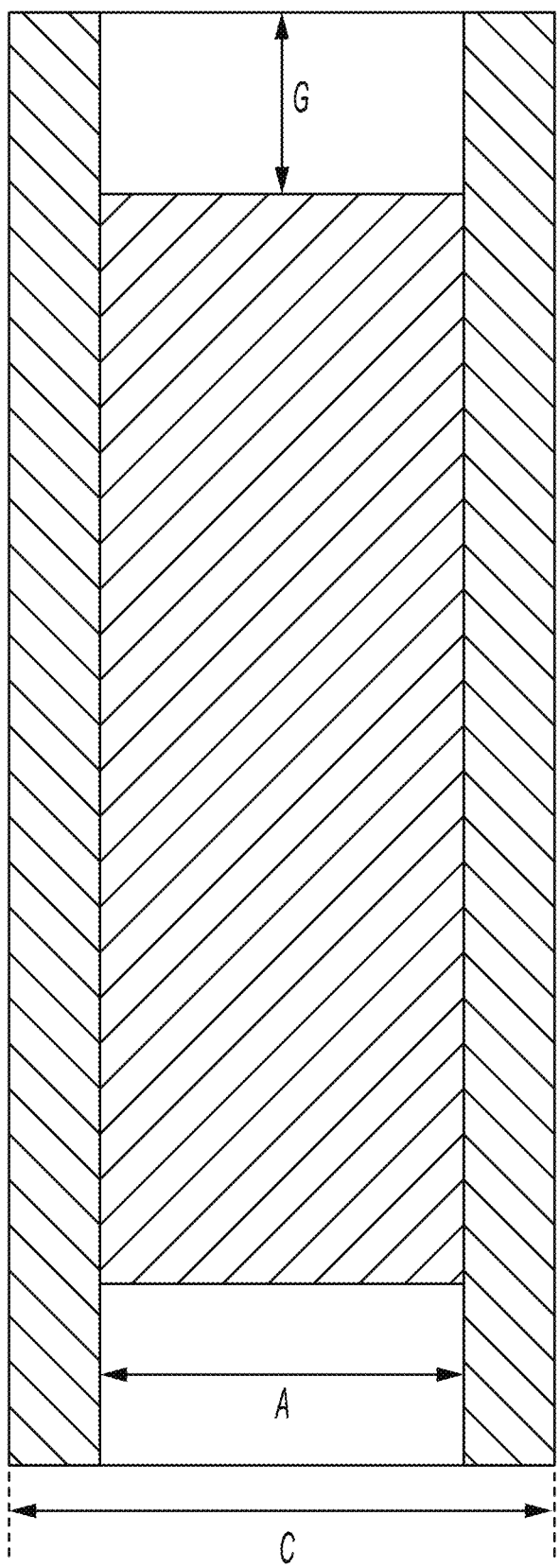
FIG. 18 depicts a longitudinal cross-section of a living electrode according to an embodiment of the invention.

Applicant advanced micro-tissue engineering methodology to improve the consistency of the biomaterial construction of the micro-columns. Here, a commercially available BIOBOTS™ 3D printer designed for tissue engineering applications was used to print the micro-columns from hyaluronic acid or a similar hydrogel. Micro-columns were printed at outer diameter C of 200 µm and inner diameter A of 100-150 µm inner diameter while concurrently being filled with a bioactive extracellular matrix (generally 1 mg/mL collagen and/or 1 mg/mL laminin), leaving a gap having a depth G of 100 µm on one or both ends of the micro-column free for cell aggregate delivery as depicted in FIG. 18. The micro-TENN can be printed with a central radial axis oriented horizontally or vertically. Horizontal printing may be preferred for speed and/or so that any ridges, grooves, or other artifacts from printing run parallel to the central radial axis and can act as a guide for neural growth.

Use as Biological Interface

Embodiments of the invention can be utilized as interfaces between hosts and various electronic devices. Although embodiments of the invention have been described in the context of optical or magnetic sensors, embodiments of the invention can also support interfacing via electrical impulses applied to neurons within the living electrodes.

As discussed herein, tissue engineered "living electrodes" will allow a stable long-term interface to probe and modulate the nervous system. "Living electrodes" increase target specificity while mitigating foreign body response inherent in non-organic electrodes.

Without being bound by theory, Applicant believes that the invention described herein operates via one or more of the following mechanisms of action. First, embodiments of the invention provide target specificity by integrating with specific neuronal subtype(s) while mitigating chronic foreign body response. Second, embodiments of the invention provide synaptic integration that offers permanence not possible with prior approaches. Third, biological multiplexing is possible through the robust effects elicited by relatively few axons. Integration of tailored "living electrodes" is synaptic-mediated with specific cells/regions in the brain. Synaptic integration via engineered axonal tracts offers a permanence and target specificity not possible with conventional approaches.

Synaptic-based interfaces using engineered neurons and/or axonal tracts can form a biological link between host and electronics, ultimately enabling prosthetic control, sensory/proprioceptive feedback, and/or neuromodulation.

A robust effect, i.e., the recruitment of numerous host neurons, can be elicited by relatively few axons via a novel mechanism referred to as "biological multiplexing". For instance, one micro-TENN axon can (in theory) synapse with hundreds or even thousands of neurons, creating a significant amplification effect. Applicant currently builds micro-TENNs with ~50,000 neurons within a column approximating the diameter of a human hair—thus presenting the potential to affect millions of host neurons with a single construct.

In various embodiments, neuron phenotypes can be selected to release/secrete certain specific neurotransmitters to restore levels relevant to particular disease processes. In various embodiments, constructs can be tailored to specific lengths to achieve connectivity at specific anatomical targets and synapse with specific neuronal subtypes within those regions. In various embodiments, the proteinacious matrix and co-delivered factors can be altered to haptotactically and chemotactically attract specific host neuron-types to be targeted by the modulation. In various embodiments, the construct neurons can target specific neurons without any extraneous, artifactual activation (provided that synaptic specificity is achieved). In various embodiments the constructs can be seeded with one or more populations of neurons, these living neural networks can perform multiplexing operations both within themselves and by achieving high information targeted output to parenchyma.

Micro-TENNs Plated with Dissociated Neuronal Suspensions

Dopaminergic neurons were isolated from the ventral mesencephalon of embryonic rats. In planar culture, these neurons demonstrated a healthy neuronal morphology, the presence of dopaminergic neurons (based on TH expression), significant neurite outgrowth (based on (β-tubulin III expression), and network formation out to 28 DIV. To create dopaminergic micro-TENNs, initially seeded micro-columns using dissociated neuronal suspensions were used. These dissociated cells infiltrated the length of the inner lumen and generally did not produce the desired cytoarchitecture of a discrete cell body region projecting axons across the length of the inner core.

However, the dissociated neurons within the micro-tissue constructs presented a healthy morphology, and occasionally self-organized into the desired cytoarchitecture by chance. In these cases, unidirectional axonal projections achieved lengths of several millimeters, and, importantly, the health of these constructs was also maintained out to 28 DIV. In order to see if the inclusion of additional ECM in the inner core increased the consistency with which the correct architecture was generated, dissociated cells were suspended into collagen, and injected the mixture to gel inside the micro-columns.

Unfortunately, the presence of the collagen did not aid in producing the desired cytoarchitecture, and the dissociated cells continued to spread throughout the length of the inner core (FIG. 23A1, FIG. 32A2, and FIG. 23A3). While these results demonstrated the ability to culture dopaminergic neurons that formed extensive neurite networks within hydrogel micro-columns, these techniques were not sufficient to consistently generate the desired cytoarchitecture.

Forced Neuronal Aggregation Method

As previous micro-TENN fabrication methods did not reliably generate the desired cytoarchitecture, a method to mechanically group neurons into aggregates was adapted (Ungrin M D, Joshi C, Nica A, et al. 2008, Reproducible, ultra high-throughput formation of multicellular organization from single cell suspension-derived human embryonic stem cell aggregates, PloS one, 3 (2): e1565.). After dissociating embryonic tissue into a single cell suspension, this solution was centrifuged in inverted pyramidal wells in order to pellet the cells at the bottom of the wells. The wells were left in the incubator overnight, during which the pelleted cells became aggregated spheres of neurons. Once formed, the aggregates were inserted into the ends of the agarose micro-columns. This method consistently produced micro-TENNs with distinct cell body and axonal regions. Furthermore, it was found that based upon the depth and placement of the aggregate within the micro-column, it was possible to create micro-TENNs that exhibited either an externalized or internalized cell body region (FIG. 23B-D). Moreover, this technique produced long-projecting unidirectional axonal tracts, as demonstrated based on TH and β-tubulin III immunoreactivity (FIG. 23E-F). Indeed, as measured by the length of the longest neurite in each micro-TENN, it was determined that the axons projecting from the aggregates grew approximately 10× longer than analogous axons extending within microcolumns seeded with dissociated neurons (FIG. 23G).

Optimization of Micro-TENN Length

The nigrostriatal pathway measures approximately 6 mm in the rat, therefore micro-TENNs at least 6 mm in length are desirable. The effects of the ECM constituents in the inner lumen, presence of growth factors, and the micro-TENN directionality on outgrowth were tested in order to optimize growing conditions for length. It was found that collagen I and collagen I and laminin resulted in the longest axonal outgrowth, as measured by the length of the longest neurite in each micro-TENN (FIG. 24A1-FIG. 24F). The average axonal outgrowth for the collagen I and collagen I and laminin cores was 4892±703 µm and 4686±921 µm respectively. In contrast, it was found that crosslinked collagen (1227±481 µm), laminin-coated (205±615 µm), and empty cores (~0 µm) resulted in significantly reduced neurite outgrowth. For the two highest performing groups (lumen comprised of collagen or collagen and laminin), it was determined that TH+ dopaminergic axonal projections attained at least 60% of the maximal axonal length (FIG. 24F). The effect of the media growth factor concentration on axonal outgrowth within the micro-columns was also tested. A media containing a relatively low concentration of bFGF (4 ng/mL) was compared to media containing high concentrations of growth factors previously shown to increase dopaminergic neuron outgrowth and survival. At 14 DIV, it was found that the high growth factor concentration media did not result in denser or longer axonal outgrowth compared to the low concentration media (n=14 micro-TENNs in each group). Lastly, it was investigated whether the use of a target population of dopaminergic cells would increase axonal outgrowth. Bidirectional dopaminergic micro-TENNs were plated by inserting dopaminergic aggregates into both ends of the micro-columns. While the two dopaminergic neuron populations were separated by 1.2 cm, in order to determine if chemotactic signaling between the populations would increase outgrowth. At 14 DIV, it was determined that the axonal outgrowth in bidirectional micro-TENNs was not greater than axonal outgrowth in unidirectional micro-TENNs (n=14 micro-TENNs in each group). Thus, the use of engineered neuronal aggregates and specific ECM constituents were critical factors in axonal extension, while high growth factor media and the presence of a target neuron population did not affect axonal outgrowth. Of note, the mean neuronal aggregate length at 14 DIV was 1165±212 µm; therefore, the total micro-TENN length (neuronal aggregate+axon length) attained using dopaminergic aggregates in collagen was >6 mm by 14 DIV—suitable to span the nigrostriatal pathway in rats. Following optimization studies, dopaminergic micro-TENNs with an inner core of collagen I were fabricated and allowed to grow over 28 DIV to ascertain if axonal extension progressed further within the micro-columns. Continued axonal extension out to 28 DIV was found, with lengths of 6046±670 µm for dopaminergic axons, 7697±1085 µm for all axons, and 8914±1187 µm for total aggregate+axon lengths. In some cases, maximum total micro-TENN lengths at this time point were over 10 mm, well beyond what would be required to span the nigrostriatal pathway in rats (FIG. 25A-FIG. 25G).

Formation of Synapses with Striatal Population

As the dopaminergic axons comprising the nigrostriatal pathway synapse with striatal neurons in the brain, the ability of tissue engineered nigrostriatal pathways to synapse with a population of striatal neurons in vitro was probed. Dopaminergic micro-TENNs were generated and, after 10 DIV, embryonic rat striatal aggregates were inserted into the vacant ends of the micro-columns. After 4 more DIV, immunocytochemistry was performed in order to assess potential synaptic integration between the two populations. This analysis confirmed the presence of the appropriate neuronal sub-types in the two aggregate populations, specifically TH+ dopaminergic neurons and DARPP-32+ medium spiny striatal neurons (FIG. 26A-FIG. 26H). Moreover, confocal microscopy revealed extensive axonaldendritic integration and putative synapse formation involving the dopaminergic axons and striatal neurons (FIG. 26D, FIG. 26E, FIG. 26G, FIG. 26H). Also, immunocytochemistry confirmed that the majority of the striatal (DARPP-32+) neurites were also MAP-2+, suggesting that these were dendrites (data not shown). In order to determine if chemotactic cues generated by the striatal population influenced axonal outgrowth from the dopaminergic neuron aggregates, the length of axonal outgrowth was quantified with and without the striatal end target. It was found that the axonal outgrowth in dopaminergic micro-TENNs containing a target population of striatal neurons was not statistically greater than axonal outgrowth in unidirectional dopaminergic micro-TENNs (n=9 micro-TENNs in each group; FIG. 26F).

Transplant and Survival of Preformed Dopaminergic Micro-TENNs In Vivo

In order to demonstrate the ability to precisely deliver preformed dopaminergic micro-TENNs into the brain as well as their survival and architecture at various time points post-implant, dopaminergic aggregate micro-TENNs with an inner lumen containing collagen I were transduced to express GFP and grown for 14 DIV, after which time they were drawn into a custom needle and stereotaxically microinjected to approximate the nigrostriatal pathway in adult male Sprague-Dawley rats. Animals were sacrificed at 1 week and 1 month time points (n=5 each), revealing surviving GFP+ neurons and axons within the micro-TENN lumen, which was easily identified spanning the nigrostriatal pathway since the agarose micro-column had only partially degraded at these time point (FIG. 27A-FIG. 27D). Histological sections were co-labeled for the axonal marker β-tubulin III and the dopaminergic marker TH, revealing the preservation of a robust neuronal and dopaminergic axonal population. In particular, longitudinally projecting TH+ axons were present, which confirmed that the micro-TENNs were able to maintain their cytoarchitecture following transplantation into the brain (FIG. 27A-FIG. 27D).

Quantification of Living Electrode Growth In Vitro

Figure 29F:
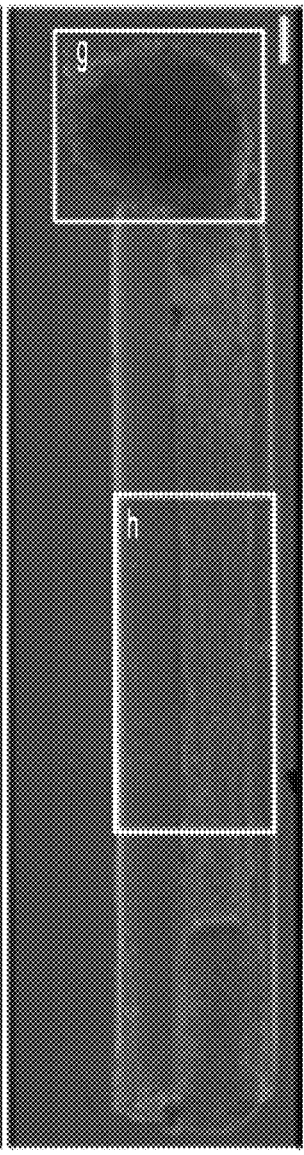
Figure 29G:
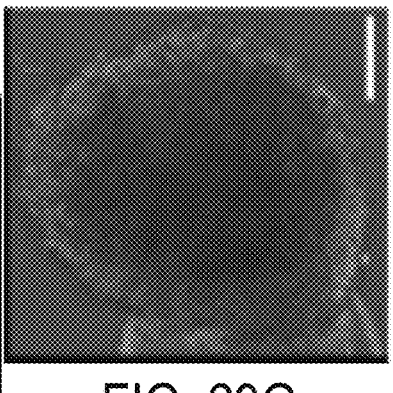
Figure 29H:
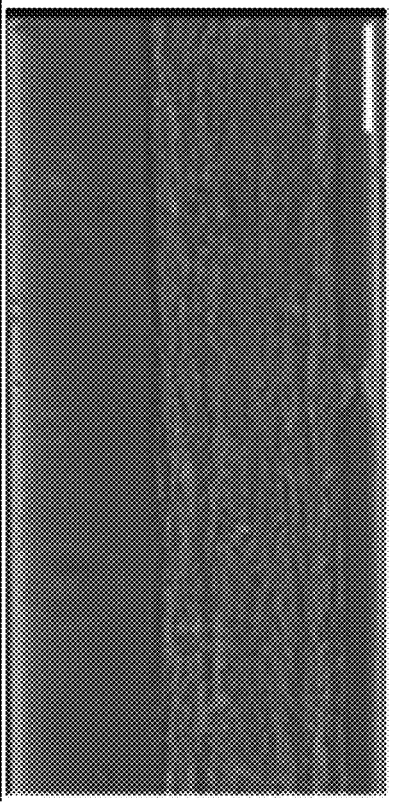
Figure 30A:
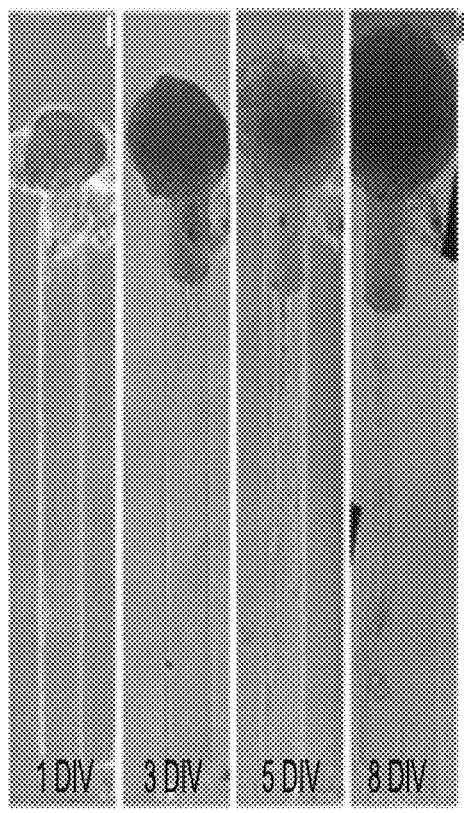
FIG. 30A-FIG. 30D depict axonal growth in aggregate micro-TENNs over time. Both unidirectional (FIG. 30A) and bidirectional (FIG. 30B) micro-TENNs displayed robust axonal outgrowth along the ECM core over the first few DIV. Unidirectional micro-TENNs, lacking a distal target, exhibited axonal retraction after about 7-8 DIV. Conversely, bidirectional micro-TENN axons crossed the length of the microcolumn (2-2.5 mm), synapsing with the opposing aggregate by 5 DIV. Representative micro-TENNs shown at 1, 3, 5, and 8 DIV.
Figure 30B:
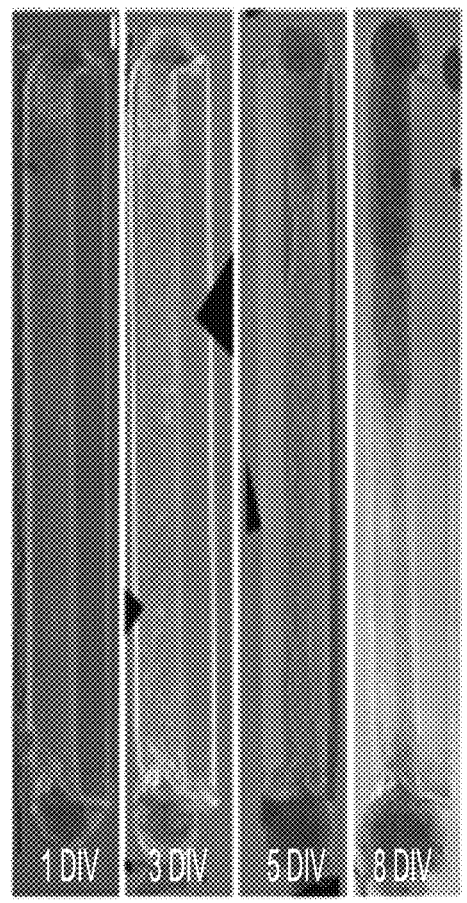
Figure 30C:
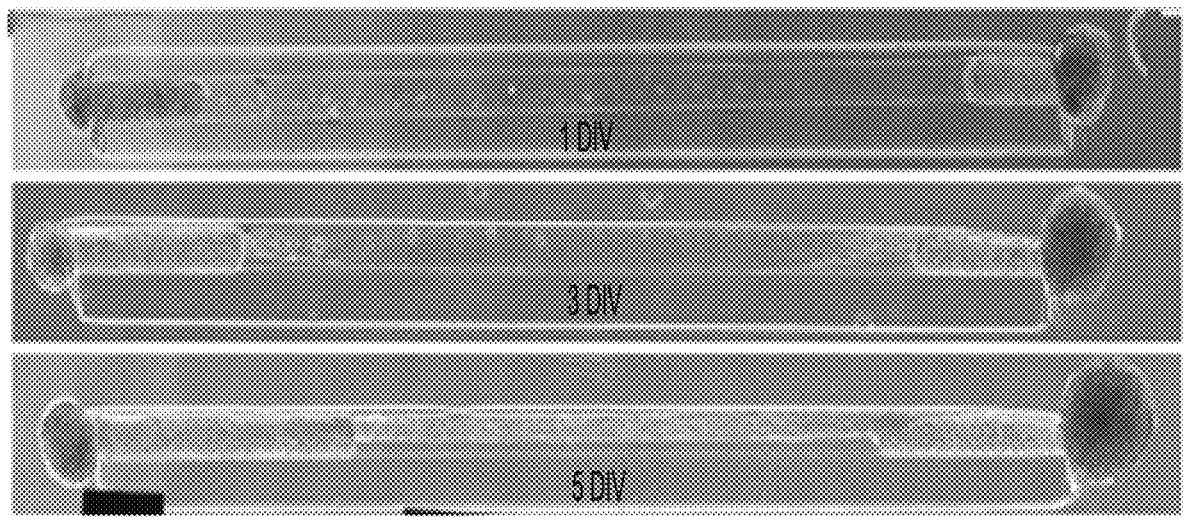
Figure 30D:
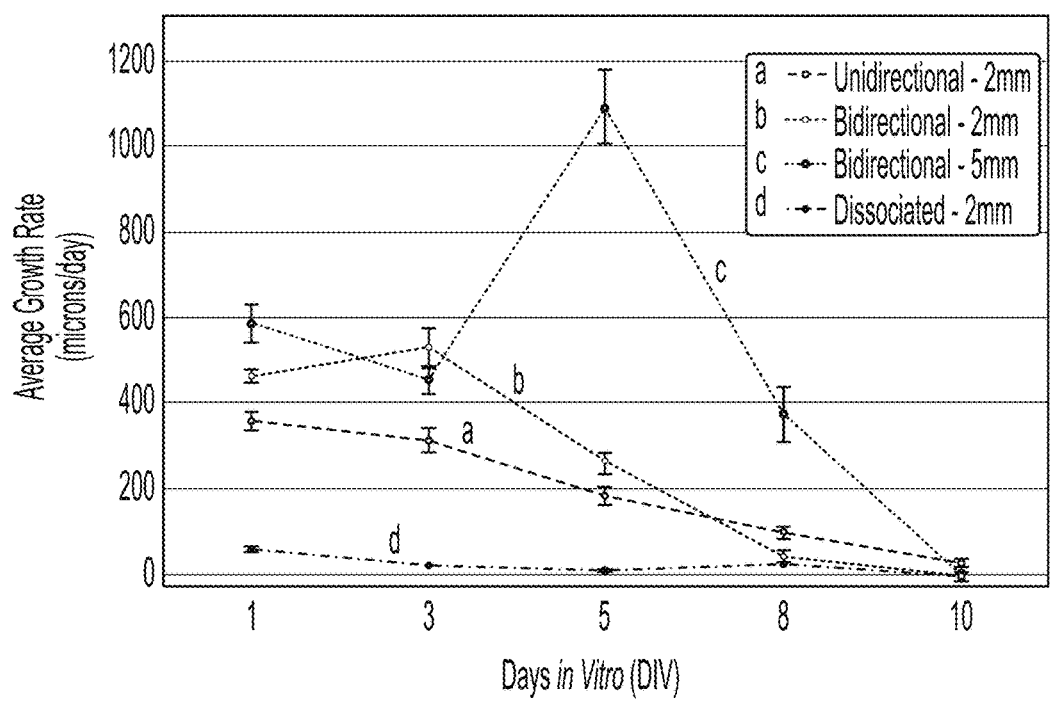

In earlier work, micro-TENNs were seeded with single cell suspensions of primary cortical neurons, which in many cases formed clusters at random sites throughout the micro-TENN interior (FIG. 29C, FIG. 29D). Current-generation micro-TENNs were formed with cortical aggregates that have been preformed prior to plating in the micro-columns, allowing for greater control and reproducibility of the desired cytoarchitecture of discrete somatic and axonal zones (FIG. 29F-FIG. 29H). This reproducibility lends itself to robust analysis of micro-TENNs in vitro, a necessary step in applying them as living electrodes. Aggregate micro-TENNs were plated with approximately 8,000-10,000 neurons per aggregate, with micro-column lengths of 2 mm and 5 mm. Both unidirectional (with one aggregate) and bidirectional (with two aggregates) 2 mm-long micro-TENNs were plated ($LE_{UNI,2mm}$ and $LE_{BI,2mm}$), while all 5 mm-long LEs ($LE_{BI,5mm}$) were plated as bidirectional constructs. Growth characteristics of prior dissociated micro-TENNs were compared to current aggregate-based constructs by plating 2 mm-long dissociated micro-TENNs ($LE_{DISS,2mm}$) (Table 1, FIG. 30A-FIG. 30D). Healthy axonal outgrowth was found across all aggregate LEs along the ECM core within the first few days in vitro through analysis of phase microscopy images (FIG. 30A-FIG. 30D). Aggregate LE neurons within the $LE_{BI,5mm}$ group displayed rapid axonal growth rates peaking at 1087.7±84.3 microns/day across all measured DIV. Neurons within the $LE_{UNI,2mm}$ group exhibited an initial peak axonal growth rate of 358±19.8 microns/day on day 1 that declined steadily over time. Within the $LE_{BI,2mm}$ group, neuronal processes had crossed the length of the micro-column and synapsed with the opposing population by 5 DIV (FIG. 30A), with a concomitant decrease in growth rate (FIG. 30D). Although neurons from the $LE_{BI,5mm}$ group grew at a similar rate to $LE_{BI,2mm}$ neurons for the first three DIV, they exhibited a significant increase in growth rate by 5 DIV and subsequent slowing of axonal growth as the synapses were formed across aggregates (FIG. 30C-FIG. 30D). Growth rates in all aggregate micro-TENN groups surpassed those of dissociated micro-TENNs, which reached a maximum growth rate of 61.7±5 microns/day at 1 DIV (Table 1).

Two-way ANOVA revealed significant main effects from the DIV (F-statistic=15.97) and LE group (Fstatistic=27.4), as well as their interaction (F-statistic=5.92), all at $p<0.0001$. As such, Bonferroni analysis was used for subsequent pairwise comparisons, revealing several statistical differences both within and between LE groups at different DIV. In general, the growth rates for bidirectional micro-TENNs were greater at earlier timepoints than later timepoints, while the growth rates for dissociated and unidirectional micro-TENNs did not vary significantly over time. Notably, the growth rate of $LE_{BI,5mm}$ at 5 DIV was greater than all growth rates for $LE_{DISS,2mm}$ ($p<0.0001$), $LE_{UNI,2mm}$ ($p<0.0001$), and $LE_{BI,2mm}$ ($p<0.001$). Moreover, within the $LE_{BI,5mm}$ group itself, the growth rate at 5 DIV was statistically greater than that of all other DIV ($p<0.01$). The growth rate of $LE_{BI,2mm}$ at 3 DIV was also greater than all growth rates for $LE_{DISS,2mm}$ ($p<0.01$). The growth rate at 1 DIV was greater than that at 10 DIV for both $LE_{BI,5mm}$ ($p<0.001$) and $LE_{BI,2mm}$ ($p<0.01$).

Bidirectional micro-TENNs labeled with GFP and mCherry were imaged over time to observe interactions between axonal projections from each aggregate (FIG. 31A-31F). Confocal images revealed that upon making contact with opposing axons, projections continued to grow along each other towards the opposing aggregate, confirming physical interaction between the two neuronal populations (FIG. 31A-31F).

Acute and Chronic Viability of Living Electrodes

Figure 32A:
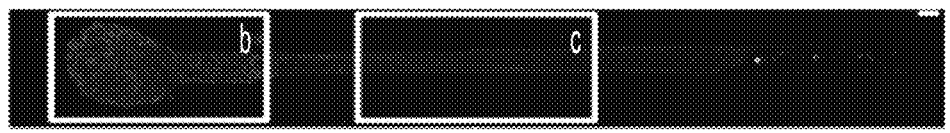
FIG. 32A-FIG. 32H illustrate micro-TENN viability. Viability for unidirectional and bidirectional micro-TENNs and age-matched two-dimensional controls was quantified via live-dead (calcein-AM/ethidium homodimer) staining at 10 and 28 DIV.
Figures 32B, 32C:
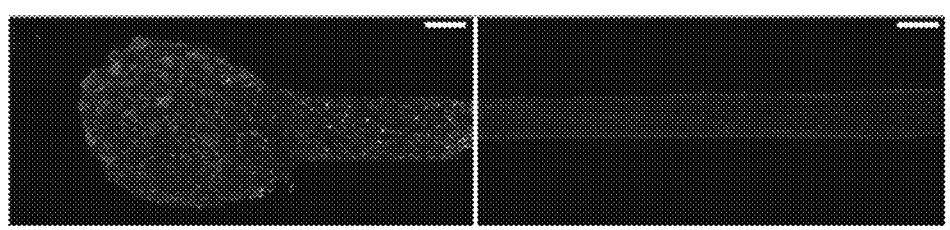
Figure 32D:
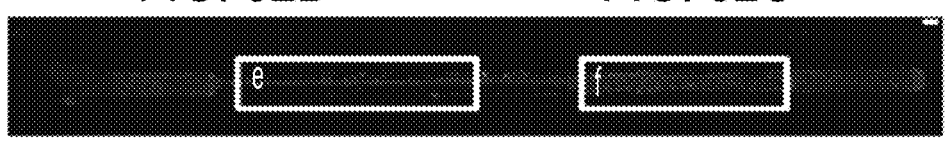
Figures 32E, 32F:
Figure 32G:
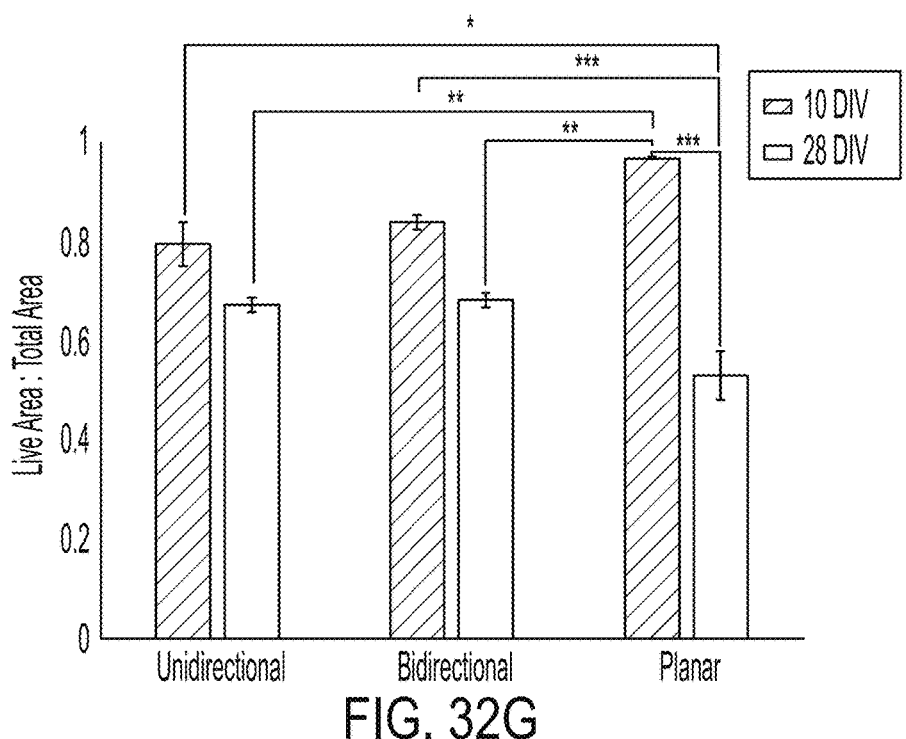
Figure 32H:
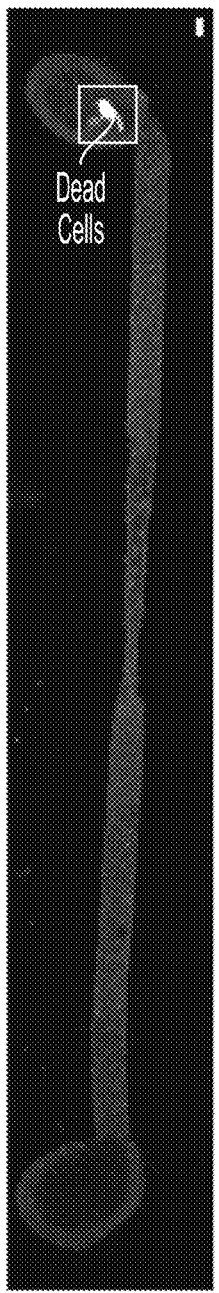
Figure 33C:
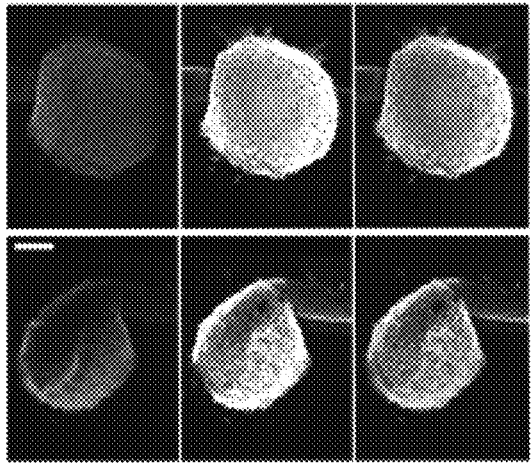
FIG. 33A-FIG. 33F depict micro-TENN architecture and synaptogenesis. Confocal reconstructions of representative bidirectional micro-TENNs at 4 DIV (FIG. 33A), 10 DIV FIG. 33B, and 28 DIV FIG. 33D; immunolabeled for cell nuclei (Hoechst), axons (Tuj-1), and synapses (synapsin). Insets in FIG. 33B and FIG. 33D refer to callout boxes (c) and (e) showing zoom-ins of synapses, axonal networks, and the overlay of the two.
Figure 33F:
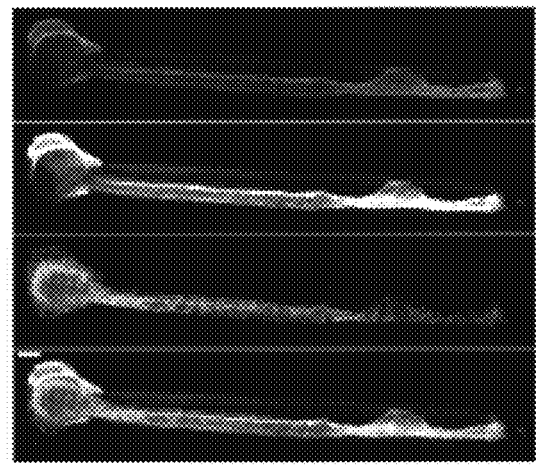
Figure 33B:
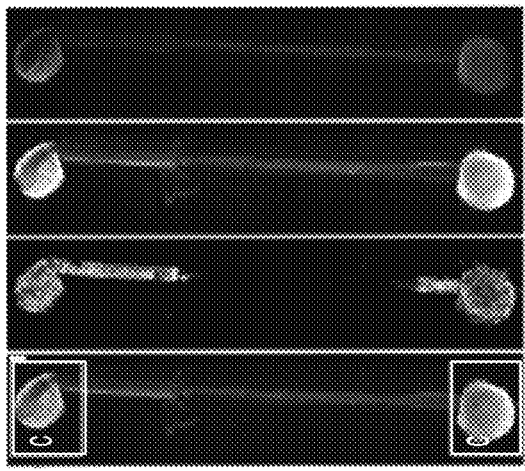
Figure 33E:
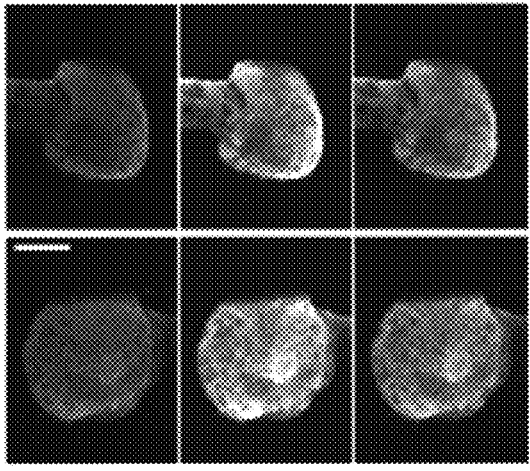
Figure 33A:
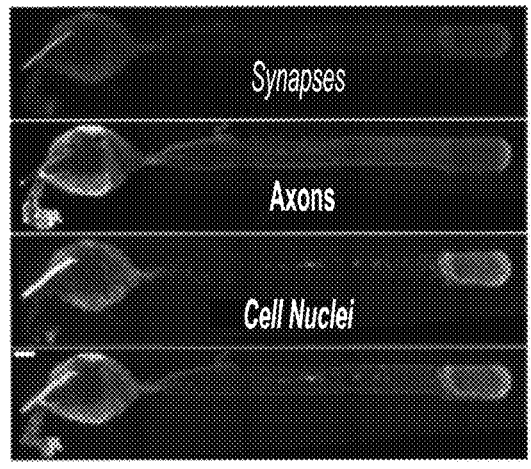
Figure 33D:
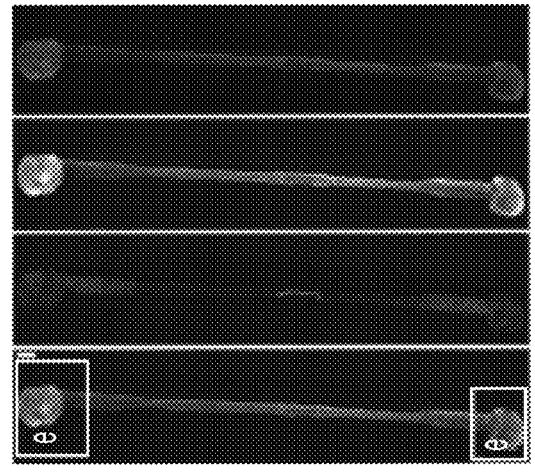

Survival was quantified via live/dead staining and confocal microscopy for short unidirectional and short bidirectional LEs at 10 and 28 DIV (FIG. 32A-FIG. 32H). Age-matched planar cultures served as controls. Viability was defined as the ratio of the summed area of calcein-AM-positive cells to that of all stained cells (i.e. both calcein-AM+ and ethidium homodimer+ cells). Neuronal survival in living electrodes was observed to persist up to at least 28 DIV, with evidence of survival out to 40 DIV (FIG. 32A-FIG 32H). ANOVA showed that although the DIV was a significant main effect (F-statistic=32.21, $p<0.0001$), the LE/culture group was not ($p>0.84$). The interaction effect was also found significant ($p<0.01$), so Bonferroni analysis was used to compare groups at each time point (FIG. 32C). Survival of planar cultures at 28 DIV was found statistically lower than that of $LE_{UNI}$ ($p<0.05$), $LE_{BI}$ ($p<0.001$), and planar cultures ($p<0.0001$) at 10 DIV. Moreover, planar culture viability at 10 DIV surpassed those of both $LE_{UNI}$ and $LE_{BI}$ at 28 DIV ($p<0.01$).

Architecture and Synaptogenesis in Living Electrodes Over Time

To characterize LE architecture over time, bidirectional LEs were fixed at 4, 10, and 28 DIV and immunolabeled to identify cell nuclei, axons, and synapses (FIG. 33A-FIG. 33F). Neuronal somata were localized almost exclusively to the aggregates, which were spanned by long axons, as indicated with Tuj-1 (FIG. 33A-FIG. 33F); axons and dendrites were also found within the aggregates from intra-aggregate connections, presumably formed upon or shortly after plating. Synapse presence was qualitatively assessed using the sum area of synapsin 1-positive puncta across the specified timepoints. A modest distribution of synapsin within micro-TENN aggregates was observed, as well as an increase in synapsin expression within the lumen of the micro-columns, suggesting that neurons within bidirectional micro-TENNs may have the capacity to communicate across aggregates.

Corticothalamic Implantation

Preformed micro-TENNs—fabricated as described above to consist of aligned axonal tracts projecting from a neuronal aggregate encased in a tubular hydrogel micro-column—were implanted to replicate corticothalamic pathways by connecting the whisker barrel cortex with the VPM. One month-post injection in the rodent brain, GFP+ micro-TENNs were found to have survived and maintained the preformed architecture of somatic-axonal distribution (FIG. 34A-FIG. 34E). Large, dense clusters of GFP+ cell bodies (aggregates) were found at the dorsal and ventral regions of

TABLE 1

Micro-TENN Growth Rates. Data presented as mean ± s.e.m. in units of microns/day.

| | $LE_{UNI, 2\ mm}$ | $LE_{BI, 2\ mm}$ | $LE_{BI, 5\ mm}$ | $LE_{DISS, 2\ mm}$ |
|---|---|---|---|---|
| 1 DIV | 358.548 ± 19.839 | 462.720 ± 14.118 | 585.328 ± 43.337 | 61.724 ± 5.009 |
| 3 DIV | 312.800 ± 27.483 | 532.548 ± 39.930 | 453.618 ± 30.928 | 23.244 ± 3.406 |
| 6 DIV | 185.425 ± 19.793 | 262.589 ± 23.375 | 1087.715 ± 84.269 | 9.480 ± 1.491 |
| 8 DIV | 97.423 ± 14.406 | 40.819 ± 13.606 | 373.588 ± 64.096 | 29.757 ± 4.348 |
| 10 DIV | 29.376 ± 7.595 | 0 | 0 | −5.377 ± 7.501 | implantation, with axons and dendrites within the lumen spanning the two locations (FIG. 34A-FIG. 34E).

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A method of manufacturing an implantable living electrode comprising:
    (a) providing an extracellular matrix core of a micro-column;
    (b) centrifuging a solution of neurons within one or more micro-wells to produce, via forced aggregation, one or more preformed neuronal aggregates, each comprising a plurality of neurons aggregated together; and
    (c) contacting at least one end of the extracellular matrix core with the one or more preformed neuronal aggregates.

2. The method according to claim 1, further comprising maintaining the implantable living electrode under conditions that promote axon growth within or along the extracellular matrix core.

3. The method of claim 1, wherein each of the one or more preformed neuronal aggregates is a spheroidal aggregate.

4. The method of claim 1, wherein the one or more micro wells comprise inverted pyramidal micro-wells.

5. The method of claim 1, wherein a density of neurons in the solution of neurons is at least 1 million cells/mL.

6. The method of claim 1, further comprising:
    (d) culturing the micro-column and extracellular matrix core with the one or more preformed neuronal aggregates therein for one or more days in vitro to promote growth of axonal projections from neurons within the one or more preformed neuronal aggregates into the cylindrical extracellular matrix core, such that aggregated neuronal soma occupy a zone at one or both ends of the micro-column and axonal projections of the neurons run longitudinally along at least a portion of the micro-column, directed from ends and towards a center of the micro-column.

7. The method of claim 1, wherein the one or more preformed neuronal aggregates comprise dopaminergic neurons.

8. The method of claim 7, wherein the dopaminergic neurons comprise dopaminergic A9 neurons.

9. The method of claim 1, wherein step (a) comprises 3D printing the micro-column.

10. A method of manufacturing an implantable living electrode comprising:
    (a) providing an extracellular matrix core of a micro-column; and
    (b) contacting at least one end of the extracellular matrix core with one or more spheroidal aggregates, each (i) comprising a plurality of aggregated neurons and (ii) implanted at an end of, or within, the extracellular matrix core.

11. The method of claim 10, comprising, prior to step (b), forming, via forced aggregation, the one or more spheroidal aggregates from a solution of neurons.

12. The method of claim 11, wherein forming the one or more spheroidal aggregates comprises:
    transferring, into each of one or more micro-wells, a dissociated neuron suspension comprising a plurality of dissociated neurons; and
    centrifuging the one or more micro-wells with the dissociated neuron suspension therein to produce the one or more spheroidal aggregates.

13. The method of claim 12, wherein a density of neurons in the dissociated neuron suspension is at least 1 million cells/mL.

14. The method according to claim 10, further comprising maintaining the implantable living electrode under conditions that promote axon growth within or along the extracellular matrix core.

15. The method of claim 10, further comprising:
    (c) culturing the micro-column and extracellular matrix core with the one or more spheroidal aggregates therein for one or more days in vitro to promote growth of axonal projections from neurons within the one or more spheroidal aggregates into the cylindrical extracellular matrix core, such that aggregated neuronal soma occupy a zone at one or both ends of the micro-column and axonal projections of the neurons run longitudinally along at least a portion of the micro-column, directed from ends and towards a center of the micro-column.

16. The method of claim 10, wherein the one or more spheroidal aggregates comprise dopaminergic neurons.

17. The method of claim 16, wherein the dopaminergic neurons comprise dopaminergic A9 neurons.

18. The method of claim 10, wherein step (a) comprises 3D printing the micro-column.

* * * * *